US008506930B2

(12) United States Patent
Tanifuji et al.

(10) Patent No.: US 8,506,930 B2
(45) Date of Patent: Aug. 13, 2013

(54) COMPOUNDS HAVING AFFINITY FOR AMYLOID

(75) Inventors: Shigeyuki Tanifuji, Sodegaura (JP);
Daisaku Nakamura, Sodegaura (JP);
Shinya Takasaki, Sodegaura (JP); Yuki Okumura, Sodegaura (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 0 days.

(21) Appl. No.: 13/537,422

(22) Filed: Jun. 29, 2012

(65) Prior Publication Data

US 2012/0271053 A1 Oct. 25, 2012

Related U.S. Application Data

(60) Division of application No. 12/227,487, filed on Nov. 19, 2008, now Pat. No. 8,303,935, and a continuation of application No. PCT/JP2007/059922, filed on May 15, 2007.

(30) Foreign Application Priority Data

May 19, 2006 (JP) ................................. 2006-140044
Nov. 30, 2006 (JP) ................................. 2006-324701

(51) Int. Cl.
*A61K 51/00* (2006.01)
*A61M 36/14* (2006.01)

(52) U.S. Cl.
USPC ............. 424/1.89; 546/4; 546/121; 424/1.65; 424/1.85

(58) Field of Classification Search
None
See application file for complete search history.

(56) References Cited

U.S. PATENT DOCUMENTS

| | | | |
|---|---|---|---|
| 4,727,145 | A | 2/1988 | Press |
| 6,489,337 | B1 | 12/2002 | Breitenbucher et al. |
| 7,759,349 | B2 | 7/2010 | Wizenberg et al. |
| 2005/0182059 | A1 | 8/2005 | Wizenberg et al. |
| 2009/0252679 | A1 | 10/2009 | Tanifuji et al. |

FOREIGN PATENT DOCUMENTS

| | | |
|---|---|---|
| EP | 0261912 A2 | 3/1988 |
| EP | 2 042 501 A1 | 4/2009 |
| TW | 200808795 A | 2/2008 |
| WO | 01/74813 A2 | 10/2001 |
| WO | 02/085903 A2 | 10/2002 |
| WO | 02/092086 A1 | 11/2002 |
| WO | WO 2004035522 A1 * | 4/2004 |
| WO | 2005/066177 A1 | 7/2005 |

OTHER PUBLICATIONS

Windhorst et al. Nucl. Med. Biol. 1999, 26, 651-659.*
Supplementary European Search Report dated Apr. 1, 2010 corresponding with EP Application 07743357.1.
Zhi-Ping Zhuang et al., "Structure-activity Relationship of Imidazo[1,2-a]pyridines as Ligands for Detecting beta-Amyloid Plaques in the Brain", Journal of Medicinal Chemistry, American Chemical Society,vol. 46, No. 1, Jan. 2003, pp. 237-243, XP002446716.
Office Action issued Oct. 9, 2012 in Japanese application 2008-546895.
Office Action dated Nov. 28, 2012 issued in TW Patent Application No. 96130388.
Office Action dated Dec. 7, 2012, issued in TW Patent Application No. 96130388.

* cited by examiner

*Primary Examiner* — Michael G Hartley
*Assistant Examiner* — Sean R Donohue
(74) *Attorney, Agent, or Firm* — Fitch, Even, Tabin & Flannery, LLP

(57) ABSTRACT

The present invention provides a compound which has affinity with amyloid, shows sufficiently rapid clearance from normal tissues and is suppressed in toxicity such as mutagencity. Provided is a compound represented by the following formula (1) or a salt thereof:

$$R^1 \underset{A_3 \underset{A_4}{\overset{A_2}{\bigg|}}}{\overset{A_1}{\bigg|}} N \underset{N}{\overset{}{\bigg|}} \underset{}{\overset{}{\bigcirc}} O \underset{}{\overset{}{\bigg(\bigg)_m}} R^2 \quad (1)$$

wherein $A_1$, $A_2$, $A_3$ and $A_4$ independently represents a carbon or nitrogen; $R^1$ is a halogen substituent; $R^2$ is a halogen substituent; and m is an integer of 0 to 2, provided that at least one of $R^1$ and $R^2$ is a radioactive halogen substituent, at least one of $A_1$, $A_2$, $A_3$ and $A_4$ represents a carbon, and $R^1$ binds to a carbon represented by $A_1$, $A_2$, $A_3$ or $A_4$ as well as a low-toxic diagnostic agent comprising a compound represented by the preceding formula or a salt thereof.

5 Claims, 10 Drawing Sheets

Step 1

US 8,506,930 B2

COMPOUNDS HAVING AFFINITY FOR AMYLOID

CROSS-REFERENCE TO RELATED APPLICATIONS

This application is a Divisional Patent Application of U.S. application Ser. No. 12/227,487, filed Nov. 19, 2008, which is the U.S. National Stage (371) application of PCT International Application No. PCT/JP2007/059922, filed May 15, 2007, and claims the benefit of foreign priority under 35 U.S.C. §119 based on Japanese Applications JP 2006-140044, filed May 19, 2006, and JP 2006-324701, filed Nov. 30, 2006, the entire disclosures of which applications are hereby incorporated herein by reference.

TECHNICAL FIELD

The present invention relates to a compound for use in diagnosis of cerebral degenerative disease. More specifically, the invention relates to a compound useful for amyloid detection at lesion sites in diagnosis of Alzheimer's disease and other diseases with amyloid accumulation.

BACKGROUND ART

Diseases with the onset of deposition of a fibrous protein called amyloid in various organs or tissues in bodies are generally referred to as amyloidosis. A feature common to amyloidosis is that the fibrous protein called amyloid which is enriched with the β-sheet structure is deposited at various organs systemically or at sites topically so that functional abnormalities are triggered in the organs or tissues.

Alzheimer's disease (hereinafter referred to as AD), which is a typical amyloidosis disease, is known as a disease causing dementia. This disease is lethal with progressive deposition of amyloid in brain, and thus is said to be a disease that causes concern in society compared with other amyloidosis diseases. In recent years, the number of AD patients is rapidly increasing in developed countries with aging societies, thereby causing a social problem.

From the pathohistological viewpoint, AD is characterized by three pathological findings in brain, namely development of senile plaques, formation of neurofibrillary tangles, and extensive neuronal loss. The senile plaque has a structure mainly composed of amyloid, and is said to appear at the earliest stage of AD onset and thus is pathologically found in brain about 10 or more years before appearance of clinical symptoms.

AD is diagnosed by carrying out various evaluations of cognitive functions (for example, Hasegawa scale, ADAS-JCog and MMSE) in auxiliary combination with imaging diagnosis such as CT and MRI. However, the method based on such evaluations of cognitive functions is low in diagnostic sensitivity at the early stage of the onset, and is furthermore problematic in that diagnostic results are susceptible to inborn cognitive functions of individuals. At present, it is practically impossible to establish a definite diagnosis of AD while an AD patient is still alive, because the definite diagnosis requires a biopsy of a lesion (Non-Patent Document 1).

Meanwhile, a report tells that amyloid constituting senile plaques is an aggregate of amyloid β protein (hereinafter referred to as Aβ). Also, numerous reports tell that the Aβ aggregate forms a β-sheet structure that causes nerve cell toxicity. Based on these findings, the so-called "Amyloid Cascade Hypothesis" is proposed, which suggests that cerebral deposition of Aβ triggers the downstream phenomena, namely, formation of neurofibrillary tangles and neuronal loss (Non-Patent Document 2).

Based on these facts, attempts have recently been made to detect AD in vivo using a compound having high affinity with amyloid as a marker.

Many of such probes for imaging diagnoses of cerebral amyloid are hydrophobic low-molecular compounds that are high in affinity with amyloid and high in cerebral transferability and are labeled with various radioactive species such as $^{11}C$, $^{18}F$ and $^{123}I$. For example, reports tell $^{11}C$ or radioactive halogen labeled forms of compounds including various thioflavin derivatives such as 6-iodo-2-[4'-(N,N-dimethylamino)phenyl]benzothiazole (hereinafter referred to as TZDM) and 6-hydroxy-2-[4'-(N-methylamino)phenyl]benzothiazole (hereinafter referred to as 6-OH-BTA-1) (Patent Document 1, Non-Patent Document 3); stilbene compounds such as (E)-4-methylamino-4'-hydroxystilbene (hereinafter referred to as SB-13) and (E)-4-dimethylamino-4'-iodostilbene (hereinafter referred to as m-I-SB) (Patent Document 2, Non-Patent Document 4, Non-Patent Document 5); benzoxazole derivatives such as 6-iodo-2-[4'-(N,N-dimethylamino)phenyl]benzoxazole (hereinafter referred to as IBOX) and 6-[2-(fluoro)ethoxy]-2-[2-(2-dimethylaminothiazol-5-yl)ethenyl]benzoxazole (Non-Patent Document 6, Non-Patent Document 7), DDNP derivatives such as 2-(1-{6-[(2-fluoroethyl)(methyl)amino]-2-naphthyl}ethylidene)malononitrile (hereinafter referred to as FDDNP) (Patent Document 4, Non-Patent Document 8); and imidazopyridine derivatives such as 6-iodo-2-[4'-(N,N-dimethylamino)phenyl]imidazo[1,2-a]pyridine (hereinafter referred to as IMPY) (Patent Document 3, Non-Patent Document 9). Further, some of these probes for imaging diagnosis have been studied on human imaging and have been reported to show a significant accumulation in AD patient's brain compared with normal persons (Non-Patent Document 10, Non-Patent Document 11, Non-Patent Document 12, Non-Patent Document 13).

[Patent Document 1] JP-T-2004-506723
[Patent Document 2] JP-T-2005-504055
[Patent Document 3] JP-T-2005-512945
[Patent Document 4] JP-T-2002-523383
[Non-Patent Document 1] J. A. Hardy & G. A. Higgins, "Alzheimer's Disease: The Amyloid Cascade Hypothesis.", Science, 1992, 256, p. 184-185
[Non-Patent Document 2] G. McKhann et al., "Clinical diagnosis of Alzheimer's disease: Report of the NINCDS-ADRDA Work Group under the auspices of Department of Health and Human Services Task Force on Alzheimer's Disease.", Neurology, 1984, 34, p. 939-944
[Non-Patent Document 3] Z.-P. Zhuang et al., "Radioiodinated Styrylbenzenes and Thioflavins as Probes for Amyloid Aggregates.", J. Med. Chem., 2001, 44, p. 1905-1914
[Non-Patent Document 4] Masahiro Ono et al., "11C-labeled stilbene derivatives as Aβ-aggregate-specific PET imaging agents for Alzheimer's disease.", Nuclear Medicine and Biology, 2003, 30, p. 565-571
[Non-Patent Document 5] H. F. Kung et al., "Novel Stilbenes as Probes for amyloid plaques.", J. American Chemical Society, 2001, 123, p. 12740-12741
[Non-Patent Document 6] Zhi-Ping Zhuang et al., "IBOX(2-(4'-dimethylaminophenyl)-6-iodobensoxazole): a ligand for imaging amyloid plaques in the brain.", Nuclear Medicine and Biology, 2001, 28, p. 887-894
[Non-Patent Document 7] Furumoto Y et al., "[$^{11}C$]BF-227: A New $^{11}C$-Labeled 2-Ethenylbenzoxazole Derivative for Amyloid-β Plaques Imaging.", European Journal of Nuclear Medicine and Molecular Imaging, 2005, 32, Sup. 1, P759

[Non-Patent Document 8] Eric D. Agdeppa et al., "2-Dialkylamino-6-Acylmalononitrile Substituted Naphthalenes (DDNP Analogs): Novel Diagnostic and Therapeutic Tools in Alzheimer's Disease.", Molecular Imaging and Biology, 2003, 5, p. 404-417

[Non-Patent Document 9] Zhi-Ping Zhuang et al., "Structure-Activity Relationship of Imidazo[1,2-a]pyridines as Ligands for Detecting β-Amyloid Plaques in the Brain.", J. Med. Chem., 2003, 46, p. 237-243

[Non-Patent Document 10] W. E. Klunk et al., "Imaging brain amyloid in Alzheumer's disease with Pittsburgh Compound-B.", Ann. Neurol., 2004, 55, p. 306-319

[Non-Patent Document 11] Nicolaas P. L. G. Verhoeff et al., "In-Vivo Imaging of Alzheimer Disease β-Amyloid With [11C]SB-13 PET.", American Journal of Geriatric Psychiatry, 2004, 12, p. 584-595

[Non-Patent Document 12] Hiroyuki. Arai et al., "[11C]-BF-227 AND PET to Visualize Amyloid in Alzheimer's Disease Patients", Alzheimer's & Dementia: The Journal of the Alzheimer's Association, 2006, 2, Sup. 1, 5312

[Non-Patent Document 13] Christopher M. Clark et al., "Imaging Amyloid with I123 IMPY SPECT", Alzheimer's & Dementia: The Journal of the Alzheimer's Association, 2006, 2, Sup. 1, S342

DISCLOSURE OF THE INVENTION

Problems to be Solved by the Invention

As described above, various compounds are disclosed as probes for imaging diagnosis for amyloid, and researched for clinical application.

Experiments in normal mice show that $[^{125}I]$-labeled TZDM, IBOX and m-I-SB are all transferred into brain 2 minutes after administration. However, these compounds are insufficient in clearance from normal tissues, and tend to accumulate gradually in brain as time passes after administration (JP-T-2005-512945; Zhi-Ping Zhuang et al., Nuclear Medicine and Biology, 2001, 28, p. 887-894; H. F. Kung et al., J. Am. Chem. Soc., 2001, 123, p. 12740-12741). When the clearance from normal tissues is insufficient, a problem arises in that sufficient contrast cannot be obtained at amyloid accumulation sites. $[^{11}C]$-labeled SB-13 shows a clearance from normal tissues in experiments in rats, however, it cannot be said that the clearance is sufficiently fast (Masahiro Ono et al., Nuclear Medicine and Biology, 2003, 30, p. 565-571).

Meanwhile, it is revealed that compounds having an imidazopyridine skeleton such as IMPY have a property of transferring to brain and accumulating at amyloid after administration, and also have an excellent property of rapid clearance from normal tissues unlike the above-described compounds, as a result of experiments using $[^{125}I]$-labeled compounds. However, IMPY is a compound positive in reverse mutation test. In order to use this compound as a probe for imaging diagnosis, sufficient care must be taken about dosage and administration manner. (International Publication WO03/106439 pamphlet)

FDDNP is also reported to be positive in reverse mutation test. (International Publication WO03/106439 pamphlet)

A preferable probe targeting amyloid for imaging diagnosis would be a compound that is excellent in affinity with amyloid and sufficiently rapid in clearance from normal tissues like IMPY but is suppressed in toxicity such as mutagenicity. However, no compound with such properties has been disclosed.

Furthermore, in accordance with results of our studies (refers to Comparative Example II-6 described later), it has been confirmed that IMPY accumulates unspecifically on white matter or other sites where amyloid is not deposited. As an AD diagnostic agent, a compound must be used which is suppressed in unspecific accumulation on sites other than amyloid deposition, but such a compound has not been disclosed.

The present invention has been made under such circumstances where various compounds as probes targeting amyloid for imaging diagnosis have been disclosed but there has been no compound which is confirmed to have a clinically tolerable property, and aims at providing a compound that has affinity with amyloid, exhibits sufficiently rapid clearance from normal tissues and further is suppressed in toxicity such as mutagenicity.

Means for Solving the Problems

The inventors have found that a group of compounds satisfying the above-described requirements can be obtained from a compound with an imidazopyridine-phenyl skeleton or a skeleton similar thereto whose phenyl group has a carbon atom to which an oxygen atom is attached, and thus have completed the present invention.

Specifically, according to one aspect of the present invention, a compound represented by the following formula (1):

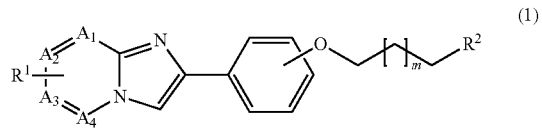

or a salt thereof, and a low-toxic diagnostic agent for Alzheimer's disease comprising a compound represented by the above formula (1) or a salt thereof are provided.

In the formula (1), $R^1$ and $R^2$ are halogen substituents, and at least either of them is a radioactive halogen substituent. Various elements can be used as the halogen, and fluorine, bromine or iodine can be preferably used. As the radioactive halogen, can be used various elements, preferably a halogen selected from $^{18}F$, $^{76}Br$, $^{123}I$, $^{124}I$, $^{125}I$, or $^{131}I$, and more preferably a halogen selected from $^{18}F$, $^{123}I$ or $^{125}I$.

$A_1$, $A_2$, $A_3$ and $A_4$ independently represent a carbon or nitrogen, and it is necessary that at least one of these represents a carbon. Preferably, 3 or more of $A_1$, $A_2$, $A_3$ and $A_4$ represent carbons, and more preferably, all of them represent carbons. In the formula (1), $R^1$ binds to a carbon represented by $A_1$, $A_2$, $A_3$ or $A_4$.

In addition, m is an integer of 0 to 2. A binding site for $R^1$ is preferably a carbon represented by $A_3$, that is, a carbon at 6-position.

According to another aspect of the present invention, a compound represented by the following formula (2):

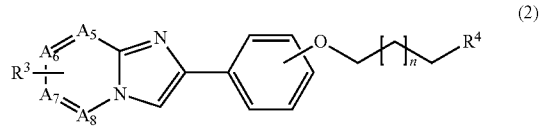

or a salt thereof is provided.

In the formula (2), $R^3$ is a group selected from the group consisting of a non-radioactive halogen substituent, nitro substituent, trialkylstannyl substituent having alkyl chains with 1 to 4 carbon atoms and triphenylstannyl substituent. As the trialkylstannyl substituent, various substituents can be used, and trimethylstannyl substituent and tributylstannyl substituent are preferably used.

$R^4$ is a group selected from the group consisting of a non-radioactive halogen substituent, methanesulfonyloxy substituent, trifluoromethanesulfonyloxy substituent and aromatic sulfonyloxy substituent. As an aromatic sulfonyloxy substituent, toluenesulfonic acid, nitrobenzenesulfonic acid and benzenesulfonic acid can be preferably used.

As a non-radioactive halogen substituent of $R^3$ and $R^4$, various halogens can be used, but preferably a halogen capable of being a target of nucleophilic substitution reactions using a radioactive fluorine or a halogen capable of being a target of isotope exchange reactions with a radioactive iodine can be used, and more preferably chlorine, iodine or bromine can be used. At least one of $R^3$ and $R^4$ is preferably the non-radioactive halogen substituent.

$A_5$, $A_6$, $A_7$ and $A_8$ independently represent a carbon or nitrogen, and it is necessary that at least one of these represents a carbon. Preferably, 3 or more of $A_5$, $A_6$, $A_7$ and $A_8$ represent carbons, and more preferably, all of them represent carbons. In the formula (2), $R^3$ binds to a carbon represented by $A_5$, $A_6$, $A_7$ or $A_8$.

In addition, n is an integer of 0 to 2.

Further, according to the present invention, there is provided a compound with an imidazopyridine-phenyl skeleton in which a carbon atom at 4'-position of the phenyl group is bonded via an oxygen atom to an alkyl chain which is substituted or non-substituted at the terminal thereof. A binding site for $R^3$ is preferably a carbon represented by $A_7$, that is, a carbon at 6-position.

Specifically, according to still another aspect of the present invention, there are provided a compound represented by the following formula (3):

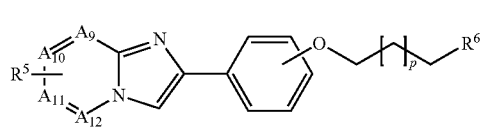

or a salt thereof, and a low-toxic diagnostic agent for Alzheimer's disease comprising a compound represented by the above formula (3) or a salt thereof. Specifically, a compound represented by the above formula (3) or a salt thereof provides a low-toxic and highly-specific diagnostic agent for Alzheimer's disease. A low-toxic and highly-specific diagnostic agent for Alzheimer's disease here refers to a diagnostic agent which has a property of accumulating at amyloid and hardly accumulating at other sites or rapidly clearing other sites even if it accumulates there, and thus shows high specificity of amyloid imaging in a certain period of time after administration.

In the formula (3), $R^5$ is a radioactive halogen substituent. As $R^5$, can be used various radioactive halogens, preferably a radioactive halogen selected from the group consisting of $^{18}F$, $^{76}Br$, $^{123}I$, $^{124}I$, $^{125}I$ and $^{131}I$, and more preferably $^{18}F$ or $^{123}I$.

$R^6$ is a group selected from the group consisting of hydrogen, hydroxyl group, methoxy group, carboxyl group, amino group, N-methylamino group, N,N-dimethylamino group and cyano group. $R^6$ is preferably hydrogen, hydroxyl group, carboxyl group or amino group, more preferably hydrogen or hydroxyl group, and particularly preferably hydroxyl group.

$A_9$, $A_{10}$, $A_{11}$ and $A_{12}$ independently represent a carbon or nitrogen, and it is necessary that at least one of these represents a carbon. Preferably, 3 or more of $A_9$, $A_{10}$, $A_{11}$ and $A_{12}$ represent carbons, and more preferably, all of them represent carbons. In the formula (3), $R^5$ binds to a carbon represented by $A_9$, $A_{10}$, $A_{11}$ or $A_{12}$. In addition, a binding site for $R^5$ is preferably a carbon represented by $A_{11}$, that is, a carbon at 6-position.

Further, p is an integer of 0 to 2.

According to further still another aspect of the present invention, a compound represented by the following formula (4):

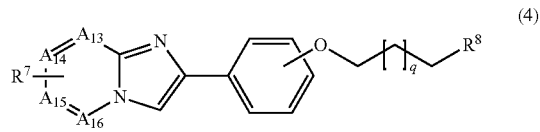

or a salt thereof is provided.

In the formula (4), $R^7$ is a group selected from the group consisting of a non-radioactive halogen substituent, nitro substituent, trialkylammonium group having alkyl chains with 1 to 4 carbon atoms, trialkylstannyl substituent having alkyl chains with 1 to 4 carbon atoms and triphenylstannyl group. As a non-radioactive halogen substituent, a halogen capable of being a target of nucleophilic substitution reactions using a radioactive fluorine or a halogen capable of being a target of isotope exchange reactions with a radioactive iodine can be used, and preferably chlorine, iodine or bromine can be used. As a trialkylstannyl substituent, various substituents can be used, and trimethylstannyl substituent and tributylstannyl substituent are preferably used.

$R^8$ is a group selected from the group consisting of hydrogen, hydroxyl group, methoxy group, carboxyl group, amino group, N-methylamino group, N,N-dimethylamino group and cyano group. $R^8$ is preferably hydrogen, hydroxyl group, carboxyl group or amino group, more preferably hydrogen or hydroxyl group, and particularly preferably hydroxyl group.

$A_{13}$, $A_{14}$, $A_{15}$ and $A_{16}$ independently represent a carbon or nitrogen, and it is necessary that at least one of these represents a carbon. Preferably, 3 or more of $A_{13}$, $A_{14}$, $A_{15}$ and $A_{16}$ represent carbons, and more preferably, all of them represent carbons. In the formula (4), $R^7$ binds to a carbon represented by $A_{13}$, $A_{14}$, $A_{15}$ or $A_{16}$. In addition, the binding site for $R^7$ is preferably a carbon represented by $A_{15}$, that is, a carbon at 6-position.

Further, q is an integer of 0 to 2.

Effects of the Invention

The present invention provides a compound that has affinity with amyloid and is sufficiently fast in clearance from normal tissues and suppressed in toxicity such as mutagenicity as well as a diagnostic agent for Alzheimer's disease with low toxicity, and further provides a compound that has high affinity with amyloid and is excellent in amyloid imaging in a living body as well as a diagnostic agent for Alzheimer's Disease high in specificity.

BEST MODE FOR CARRYING OUT THE INVENTION

I. A Method for Synthesis of a Compound of the above Formula (1) or (2)
(A Method for Synthesis of a Precursor Compound for a Radioactive Halogen-labeled Compound)

Hereinafter, a method for synthesis of a precursor compound for a radioactive halogen-labeled compound according to an embodiment of the present invention will be described, taking the case of 6-tributylstannyl-2-[4'-(3"-fluoropropoxy) phenyl]imidazo[1,2-a]pyridine.

First, 4'-hydroxyacetophenone is allowed to react with cupric bromide to prepare 2-bromo-4'-hydroxyacetophenone (FIG. 1-1, Step 1). In this instance, the reaction can be conducted in accordance with ordinary methods, for example, the method described in a literature, King, L. Carroll and Ostrum, G. Kenneth, Journal of Organic Chemistry, 1964, 29(12), p. 3459-3461.

Then, 2-bromo-4'-hydroxyacetophenone as prepared above is allowed to react with 2-amino-5-bromopyridine to prepare 6-bromo-2-(4'-hydroxyphenyl)imidazo[1,2-a]pyridine (FIG. 1-1, Step 2). This step can be done according to the following procedure.

First, 2-bromo-4'-hydroxyacetophenone and 2-amino-5-bromopyridine are dissolved in an inactive solvent such as acetonitrile, and are allowed to react with each other at a reflux temperature for 2 to 6 hours to produce 6-bromo-2-(4'-hydroxyphenyl)imidazo[1,2-a]pyridine hydrobromide salt as white precipitates. The solvent used in this instance may be acetonitrile or another solvent that is usually employed in a similar reaction, for example, methanol and acetone. The reaction temperature may be a temperature allowing refluxing, for example, 90° C. when the solvent is acetonitrile. The amount of the solvent to be used may be an amount sufficient to effect the reaction, however, it should be noted that if the solvent is too much, it will become difficult to obtain precipitates of reaction products. For example, when 2-bromo-4'-hydroxyacetophenone in an amount corresponding to 10 mmol is used for the reaction, the amount of a solvent to be used can be about 40 to 50 mL.

Next, the reaction solution is filtered to recover the precipitates. The white precipitates are suspended in a mixed solution of methanol/water (1:1). Then, an aqueous saturated solutions of sodium hydrogencarbonate is added thereto in a very excessive amount relative to the suspended precipitates to release 6-bromo-2-(4'-hydroxyphenyl)imidazo[1,2-a]pyridine as precipitates. The newly generated precipitates are filtered to recover 6-bromo-2-(4'-hydroxyphenyl)imidazo[1, 2-a]pyridine as the target compound in this step (FIG. 1-1, Step 2). The amount of the mixed solution of water/methanol is not specifically limited as long as it is sufficient to effect the reaction. However, it should be noted that if the amount of the mixed solution is too much, precipitation of products will be hindered. For example, when 2-bromo-4'-hydroxyacetophenone in an amount corresponding to 10 mmol is used, the mixed solution of water/methanol may be used in an amount of about 40 to 100 mL. The amount of sodium hydrogencarbonate is not specifically limited as long as it is very excessive relative to the above-described precipitates as reaction substrates. For example, when the reaction is effected under the above-described conditions, the amount of an aqueous saturated solution of sodium hydrogencarbonate to be added to the reaction solution can be about 25 mL.

Then, the 6-bromo-2-(4'-hydroxyphenyl)imidazo[1,2-a] pyridine prepared above is sufficiently dried, dissolved in N,N-dimethylformamide, and potassium carbonate and 3-bromo-1-fluoropropane were added thereto. The reaction solution is stirred at room temperature for overnight to obtain 6-bromo-2-[4'-(3"-fluoropropoxy)phenyl]imidazo[1,2-a]pyridine (FIG. 1-1, Step 3). The amount of potassium carbonate to be used may be an amount that can neutralize hydrobromic acid generated from 3-bromo-1-fluoropropane during the reaction, and is typically about double the other reactant 3-bromo-1-fluoropropane in molar ratio. The 3-bromo-1-fluoropropane can be used in an excessive amount relative to the reaction substrate, and is typically about 1.5 times the reaction substrate 6-bromo-2-(4'-hydroxyphenyl)imidazo[1, 2-a]pyridine in molar ratio.

The obtained 6-bromo-2-[4'-(3"-fluoropropoxy)phenyl] imidazo[1,2-a]pyridine was dissolved in dioxane, and after triethylamine is added, bis(tributyltin) and a catalytic amount of tetrakis-triphenylphosphine palladium are added. This reaction mixture is heated at about 90° C. and reacted for about 24 hours, and then a solvent is distilled off and a chromatographic purification is performed to obtain 6-tributylstannyl-2-[4'-(3"-fluoropropoxy)phenyl]imidazo[1,2-a] pyridine as the target compound (FIG. 1-1, Step 4). The amount of bis(tributyltin) to be used in this instance may be an amount satisfying a condition where it is excessive relative to the reaction substrate, specifically, it is about 1.5 times in molar ratio relative to the reaction substrate 6-bromo-2-[4'-(3"-fluoropropoxy)phenyl]imidazo[1,2-a]pyridine.

When a compound with a substituent at the 6-postion being a trialkylstannyl substituent other than tributylstannyl substituent is obtained, various bis(trialkyltin)s that fit purposes can be used instead of bis(tributyltin) in Step 4. For example, when a compound having a trimethylstannyl substituent as a substituent at the 6-position is synthesized, a reaction similar to the above can be performed in Step 4 using bis(trimethyltin).

A compound with an imidazopyridine ring in which the binding site for the functional group is a carbon atom other than the carbon at 6-position can be obtained by using a compound with a pyridine ring to which bromine is bonded at a different site instead of 2-amino-5-bromopyridine used in Step 2. For example, when a binding site for the functional group is the carbon at 8-position in the imidazopyridine ring, 2-amino-3-bromopyridine may be used instead of 2-amino-5-bromopyridine in Step 2.

Further, a precursor compound with a radioactive halogen labeled site being an alkoxyphenyl substituent attached to a carbon atom at 2-position of the imidazo pyridine ring can be obtained by using 3-bromo-1-propanol instead of 3-bromo-1-fluoropropane, and reacting a resulting compound with p-toluenesulfonylchloride or the like. For example, 6-bromo-2-[4'-(3"-p-toluenesulfonyloxypropoxy)phenyl]imidazo[1, 2-a]pyridine can be synthesized by the following procedure.

First, 6-bromo-2-(4"-hydroxyphenyl)imidazo[1,2-a]pyridine prepared above is dissolved in N,N-dimethylformamide, and the solution is supplemented with potassium carbonate and 3-bromo-1-propanol and stirred at room temperature for overnight to obtain 6-bromo-2-[4'-(3"-hydroxypropoxy)phenyl]imidazo[1,2-a]pyridine. This is dissolved in pyridine, supplemented with p-toluenesulfonylchloride under an ice bath and then reacted at room temperature to obtain 6-bromo-2-[4'-(3"-p-toluenesulfonyloxypropoxy)phenyl]imidazo[1, 2-a]pyridine as a target compound. The amount of the p-toluenesulfonylchloride to be used in this instance may be excessive relative to the reaction substrate, and is typically about double the reaction substrate 6-bromo-2-[4'-(3"-hydroxypropoxy)phenyl]imidazo[1,2-a]pyridine in molar ratio.

A compound in which the alkoxy substituent bound to the phenyl group that is bound to the 2-position of the imidazopyridine ring is bound to another position than the 4'-position, for example, 6-tributylstannyl-2-[3'-(3"-fluoropropoxy)phenyl]imidazo[1,2-a]pyridine which has a fluoropropoxy group at 3'-position, can be synthesized in accordance with the same reaction as above except using 3'-hydroxyacetophenone as a reactant instead of 4'-hydroxyacetophenone in Step 1.

(A Method for Synthesis of a Radioactive Halogen-labeled Compound)

Next, a method for production of a radioactive halogen-labeled compound according to another aspect of the present invention will be described, taking the case of 2-[4'-(3"-fluoropropoxy)phenyl]-6-[123I]iodoimidazo[1,2-a]pyridine.

For the production of 2-[4'-(3"-fluoropropoxy)phenyl]-6-[$^{123}$I]iodoimidazo[1,2-a]pyridine, a [$^{123}$I]sodium iodide solution to be served for labeling is first obtained. A [$^{123}$I] radioactive iodine can be obtained by, for example, a known method in which a xenon gas is used as a target and exposed to proton bombardment. This [$^{123}$I] radioactive iodine is made into [$^{123}$I] sodium iodide solution by using known methods, and used for the labeling.

Then, the labeling precursor 6-tributylstannyl-2-[4'-(3"-fluoropropoxy)phenyl]imidazo[1,2-a]pyridine dissolved in an inert organic solvent, and a solution of the [$^{123}$I] bulk dissolved in water, an acid and an oxidizing agent are added thereto and allowed to react to obtain 2-[4'-(3"-fluoropropoxy)phenyl]-6-[$^{123}$I]iodoimidazo[1,2-a]pyridine as a target compound. As the inert organic solvent dissolving the precursor compound, various solvents having no reactivity with the labeling precursor and [$^{123}$I]iodo bulk can be used, and preferably methanol can be used.

As the acid, may be used various ones, and preferably hydrochloric acid.

The oxidizing agent is not particularly limited as long as it can effect the oxidation of iodine in the reaction solution, and is preferably hydrogen peroxide or peracetic acid. The amount of the oxidizing agent to be added may be an amount sufficient to oxidize iodine in the reaction solution.

A compound labeled with a radioactive halogen other than iodine can be synthesized by labeling a labeling precursor that fits a purpose of synthesis with a radioactive halogen that fits the purpose. For example, in order to synthesize 2-[4'-(3"-[$^{18}$F]fluoropropoxy)phenyl]-6-bromoimidazo[1,2-a]pyridine, the labeling precursor 6-bromo-2-[4'-(3"-p-toluenesulfonyloxypropoxy)phenyl]imidazo[1,2-a]pyridine can be reacted with [$^{18}$F]fluoride ion in the presence of a phase transfer catalyst and potassium carbonate.

II. A Method for Synthesis of a Compound of the above Formula (3) or (4)
(A Method for Synthesis of a Precursor Compound for a Radioactive Halogen-labeled Compound)

Hereinafter, a method for synthesis of a precursor compound for a radioactive halogen-labeled compound according to an embodiment of the present invention will be described, taking the case of 6-tributylstannyl-2-[4'-(2"-hydroxyethoxy)phenyl]imidazo[1,2-a]pyridine.

For the production of 6-tributylstannyl-2-[4'-(2"-hydroxyethoxy)phenyl[imidazo[1,2-a]pyridine, first, 4'-hydroxyacetophenone is allowed to react with cupric bromide to prepare 2-bromo-4'-hydroxyacetophenone (FIG. 2-1, Step 1). In this instance, the reaction can be conducted in accordance with ordinary methods, for example, the method described in a literature, King, L. Carroll and Ostrum, G. Kenneth, Journal of Organic Chemistry, 1964, 29(12), p. 3459-3461.

Then, 2-bromo-4'-hydroxyacetophenone as prepared above is allowed to react with 2-amino-5-iodopyridine to prepare 2-(4'-hydroxyphenyl)-6-iodoimidazo[1,2-a]pyridine (FIG. 2-1, Step 2). This step can be done according to the following procedure.

First, 2-bromo-4'-hydroxyacetophenone and 2-amino-5-iodopyridine are dissolved in an inactive solvent such as acetonitrile, and are allowed to react with each other at a reflux temperature for 2 to 6 hours to produce 2-(4'-hydroxyphenyl)-6-iodoimidazo[1,2-a]pyridine hydrobromide salt as white precipitates. The solvent used in this instance may be acetonitrile or another solvent that is usually employed in a similar reaction, for example, methanol and acetone. The reaction temperature may be a temperature allowing refluxing, for example, 110° C. when the solvent is acetonitrile. The amount of the solvent to be used may be an amount sufficient to effect the reaction, however, it should be noted that if the solvent is too much, it will become difficult to obtain precipitates of reaction products. For example, when 2-bromo-4'-hydroxyacetophenone in an amount corresponding to 10 mmol is used for the reaction, the amount of a solvent to be used can be about 40 to 80 mL.

Next, the reaction solution is filtered to recover the precipitates. The white precipitates are suspended in a mixed solution of methanol/water (1:1). Then, an aqueous saturated solution of sodium hydrogencarbonate is added thereto in a very excessive amount relative to the suspended precipitates to release 2-(4'-hydroxyphenyl)-6-iodoimidazo[1,2-a]pyridine as precipitates. The newly generated precipitates are filtered to recover 2-(4'-hydroxyphenyl)-6-iodoimidazo[1,2-a]pyridine as the target compound in this step (FIG. 2-1, Step 2). The amount of the mixed solution of methanol/water is not specifically limited as long as it is sufficient to effect the reaction. However, it should be noted that if the amount of the mixed solution is too much, precipitation of products will be hindered. For example, when 2-bromo-4'-hydroxyacetophenone in an amount corresponding to 10 mmol is used, the mixed solution of methanol/water may be used in an amount of about 40 to 100 mL. The amount of sodium hydrogencarbonate is not specifically limited as long as it is very excessive relative to the above-described precipitates as reaction substrates. For example, when the reaction is effected under the above-described conditions, the amount of an aqueous saturated solution of sodium hydrogencarbonate to be added to the reaction solution can be about 50 mL.

Here, 2-bromoethanol and t-butyldiphenylchlorosilane (TBDPSCl) are reacted with each other to prepare 1-bromo-2-(t-butyldiphenylsiloxy)ethane (FIG. 2-1, Step 3), separately. In this instance, the reaction can be carried out in accordance with ordinary methods, for example, the method described in a literature, Organic Syntheses, Coll. Vol. 10, p. 170 (2004); Vol. 79, p. 59 (2002)).

Then, the 2-(4'-hydroxyphenyl)-6-iodoimidazo[1,2-a]pyridine prepared above is sufficiently dried, dissolved in N,N-dimethylformamide, and potassium carbonate and 1-bromo-2-(t-butyldiphenylsiloxy)ethane were added thereto. After this mixture was stirred at about 90° C. for about 2 hours, a saturated sodium chloride solution was added, extracted with ethyl acetate, concentrated an ethyl acetate layer, and chromatogram purification is performed to obtain 2-[4'-(2"-t-butyldiphenylsiloxyethoxy)phenyl]-6-iodoimidazo[1,2-a]pyridine (FIG. 2-1, Step 4). The amount of potassium carbonate to be used may be an amount that can neutralize hydrobromic acid generated from 1-bromo-2-(t-butyldiphenylsiloxy) ethane during the reaction, and is typically double to triple the other reactant 1-bromo-2-(t-butyldiphenylsiloxy)ethane in molar ratio. Further, the 1-bromo-2-(t-butyldiphenylsiloxy) ethane can be used in an excessive amount relative to the reaction substrate, and is typically about 1.5 times the reaction substrate 2-(4'-hydroxyphenyl)-6-iodoimidazo[1,2-a] pyridine in molar ratio.

Then, t-butyldiphenylsilyl group of the obtained 2-[4'-(2"-t-butyldiphenylsiloxyethoxy)phenyl]-6-iodoimidazo[1,2-a] pyridine is deprotected using tetrabutylammonium fluoride to obtain 2-[4'-(2"-hydroxyethoxy)phenyl]-6-iodoimidazo[1,2-a]pyridine (FIG. 2-1, Step 5). In this instance, the reaction can be carried out in accordance with ordinary methods, for example, the method described in a literature, Organic Syntheses, Coll. Vol. 9, p. 417 (1998); Vol. 74, p. 248 (1997)).

The obtained 2-[4'-(2"-hydroxyethoxy)]phenyl]-6-iodoimidazo[1,2-a]pyridine was dissolved in dioxane, and triethylamine is added thereto. Then, bis(tributyltin) and a catalytic amount of tetrakis-triphenylphosphine palladium are added thereto. This reaction mixture is heated at about 90° C. and reacted for about 24 hours, and then a solvent is distilled off and chromatographic purification is performed to obtain 6-tributylstannyl-2-[4'-(2"-hydroxyethoxy)]phenyl]imidazo[1,2-a]pyridine as the target compound (FIG. 2-2, Step 1). The amount of bis(tributyltin) to be used in this instance may be an amount satisfying a condition where it is excessive relative to the reaction substrate, specifically, it is about 1.5 times in molar ratio relative to the reaction substrate 2-[4'-(2"-hydroxyethoxy)phenyl]-6-iodoimidazo[1,2-a]pyridine.

When a compound with a substituent at the 6-position in the imidazopyridine ring being a trialkylstannyl substituent other than the tributylstannyl substituent is obtained, various bis(trialkyltin)s that fit purposes can be used instead of bis(tributyltin) in FIG. 2-2, Step 1. For example, when a compound having a trimethylstannyl subtituent as a substituent at the 6-position is synthesized, a reaction similar to the above can be performed in FIG. 2-2, Step 1 using bis(trimethyltin).

A compound with an imidazopyridine ring in which the binding site for the functional group is a carbon atom other than the carbon at 6-position can be obtained by using a compound with a pyridine ring to which iodine is bonded at a different site instead of 2-amino-5-iodopyridine used in FIG. 2-1, Step 2. For example, when a binding site for the functional group is the carbon at 8-position in the imidazopyridine ring, 2-amino-3-iodopyridine may be used instead of 2-amino-5-iodopyridine in FIG. 2-1, Step 2.

(A Method for Synthesis of a Radioactive Halogen-labeled Compound)

Next, a method for production of a radioactive halogen-labeled compound according to another aspect of the present invention will be described, taking the case of radioactive iodine-labeled compounds.

The synthesis of radioactive iodine-labeled compounds can be performed by dissolving the labeling precursor compound prepared as above procedure in an inert organic solvent, adding a [$^{123}$I] sodium iodide solution obtained by known methods thereto, adding an acid and an oxidizing agent thereto to effect reaction. As an inert organic solvent dissolving the labeling precursor compound, various solvents having no reactivity with the labeling precursor, [$^{123}$I]sodium iodide and the like can be used, and preferably methanol can be used.

As the acid, may be used various ones, and preferably hydrochloric acid.

The oxidizing agent is not particularly limited as long as it can effect the oxidation of iodine in the reaction solution, and is preferably hydrogen peroxide or peracetic acid. The amount of the oxidizing agent to be added may be an amount sufficient to oxidize iodine in the reaction solution.

A compound labeled with a radioactive halogen other than iodine can be synthesized by labeling a labeling precursor that fits a purpose of synthesis with a radioactive halogen that fits the purpose. For example, in order to synthesize 6-[$^{18}$F]fluoro-2-[4'-(2"-hydroxyethoxy)phenyl]imidazo[1,2-a]pyridine, the labeling precursor 2-[4'-(2"-hydroxyethoxy)phenyl]-6-nitroimidazo[1,2-a]pyridine can be reacted with [$^{18}$F] fluoride ion in the presence of a phase transfer catalyst and potassium carbonate.

(Methods for Preparing and Using a Diagnostic Agent in Accordance with the Present Invention)

The diagnostic agent according to the present invention can be prepared as a solution which comprises the present radioactive halogen-labeled compound blended in water, a physiological saline solution or a Ringer's solution optionally adjusted to an appropriate pH, like other commonly-known radioactive diagnostic agents. In this instance, concentration of the present compound should be adjusted to not more than the concentration at which stability of the present compound is ensured. Dosage of the present compound is not specifically limited as long as it is sufficient to obtain an image of distribution of an administered agent. For example, in case of iodine-123($^{123}$I)-labeled compounds and fluorine-18($^{18}$F)-labeled compounds, about 50 to 600 MBq per adult body of 60 kg weight can be administered intravenously or locally. Distribution of administered agents can be imaged by known methods. For example, iodine-123($^{123}$I)-labeled compounds can be imaged by a SPECT apparatus while fluorine-18($^{18}$F)-labeled compounds can be imaged by a PET apparatus.

EXAMPLE

Hereinafter, the present invention is described below in more detail by way of Examples, Comparative Examples and Reference Examples. However, these Examples never limit the scope of the present invention.

Example I

In the following Examples, the names of the individual compounds used in the experiment are defined as shown in Table 1-1.

TABLE 1-1

| Compound name | Common name |
| --- | --- |
| Compound I-1 | 6-bromo-2-[4'-(3"-fluoropropoxy)phenyl]imidazo[1,2-a]pyridine |
| Compound I-2 | 2-[4'-(3"-fluoropropoxy)phenyl]-6-iodoimidazo[1,2-a]pyridine |
| Compound I-3 | 6-bromo-2-[4'-(2"-fluoroethoxy)phenyl]imidazo[1,2-a]pyridine |
| Compound I-4 | 2-[4'-(2"-fluoroethoxy)phenyl]-6-iodoimidazo[1,2-a]pyridine |
| Compound I-5 | 2-[4'-(3"-fluoropropoxy)phenyl]-6-iodoimidazo[1,2-a]pyrimidine |
| Compound I-6 | 2-[4'-(3"-fluoropropoxy)phenyl]-6-[$^{125}$I]iodoimidazo[1,2-a]pyridine |
| Compound I-7 | 2-[4'-(3"-fluoropropoxy)phenyl]-6-[$^{123}$I]iodoimidazo[1,2-a]pyridine |
| Compound I-8 | 6-bromo-2-[4'-(3"-[$^{18}$F]fluoropropoxy)phenyl]imidazo[1,2-a]pyridine |
| Compound I-9 | 2-[4'-(2"-fluoroethoxy)phenyl]-6-[$^{123}$I]iodoimidazo[1,2-a]pyridine |

Example I-1

Synthesis of 6-tributylstannyl-2-[4'-(3"-fluoropropoxy)phenyl]imidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated.

The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-1, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 1-1, Step 2).

290 mg (corresponding to 1.0 mmol) of 6-bromo-2-(4'-hydroxyphenyl)imidazo[1,2-a]pyridine that was sufficiently dried to remove moisture was dissolved in 10 mL of N,N-dimethylformamide, and 413 mg (corresponding to 3.0 mmol) of potassium carbonate was added thereto. The mixture was supplemented with 138 µL (corresponding to 1.5 mmol) of 1-bromo-3-fluoropropane, and then was stirred at room temperature for 20.5 hours. After the completion of the reaction, the reaction solution was poured into water and extracted three times with chloroform. The combined chloroform layer was washed with a saturated sodium chloride solution, dried over anhydrous sodium sulfate, filtered and concentrated. The resulting crude product was purified by recycle preparative HPLC(HPLC apparatus: LC-908 (under trade name; manufactured by Japan Analytical Industry Co., Ltd.); column: two JAIGEL 2H (under trade name; manufactured by Japan Analytical Industry Co., Ltd.) connected together; mobile phase: chloroform), to obtain 302 mg (corresponding to 0.866 mmol) of 6-bromo-2-[4'-(3"-fluoropropoxy)phenyl]imidazo[1,2-a]pyridine (FIG. 1-1, Step 3).

85 mg (corresponding to 0.24 mmol) of 6-bromo-2-[4'-(3"-fluoropropoxy)phenyl]imidazo[1,2-a]pyridine was dissolved in 10 mL of dioxane, and 2 mL of triethylamine was added thereto. Then, 185 µL (corresponding to 0.36 mmol) of bis(tributyltin) and 20 mg (at a catalytic amount) of tetrakistriphenylphosphine palladium were added thereto. After the reaction mixture was stirred at 90° C. for 24 hours, the solvent was distilled off under reduced pressure. The residue was purified by the preparative TLC (elution solvent: hexane/ethyl acetate=6/4). Further, the resulting crude product was purified by recycle preparative HPLC(HPLC apparatus: LC-908 (under trade name: manufactured by Japan Analytical Industry Co., Ltd.); column: two JAIGEL 2H (under trade name; manufactured by Japan Analytical Industry Co., Ltd.) connected together; mobile phase: chloroform), to obtain 42 mg (corresponding to 74.2 µmol) of 6-tributylstannyl-2-[4'-(3"-fluoropropoxy)phenyl]imidazo[1,2-a]pyridine (FIG. 1-1, Step 4).

The NMR measurement results of the resulting 6-tributylstannyl-2-[4'-(3"-fluoropropoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.01-7.93 (m, 1H), 7.91-7.87 (m, 2H), 7.75-7.74 (m, 1H), 7.63-7.58 (m, 1H), 7.20-7.11 (m, 1H), 7.00-6.95 (m, 2H), 4.67 (dt, $J_{HF}$=47.0 Hz, J=6.0 Hz, 2H), 4.15 (t, J=6.0 Hz, 2H), 2.20 (dquint, $J_{HF}$=26.1 Hz, J=6.0 Hz, 2H), 1.64-1.47 (m, 6H), 1.39-1.31 (m, 6H), 1.19-1.04 (m, 6H), 0.91 (t, J=7.2 Hz, 9H)

Example I-2

Synthesis of 2-[4'-(3"-fluoropropoxy)phenyl]-6-[$^{125}$I]iodoimidazo[1,2-a]pyridine To 53 µL of a solution of 6-tributylstannyl-2-[4'-(3"-fluoropropoxy)phenyl]imidazo[1,2-a]pyridine in methanol (concentration: 1 mg/mL), 100 µL of 1 mol/L hydrochloric acid, [$^{125}$I]sodium iodide of 11.1 MBq (20 µL in volume) and 10 µL of 100 (w/v) hydrogen peroxide were added. After the mixed solution was left to stand at room temperature for 10 minutes, the solution was subjected to HPLC under the following conditions, to obtain 2-[4'-(3"-fluoropropoxy)phenyl]-6-[$^{125}$I]iodoimidazo[1,2-a]pyridine fraction.

HPLC conditions:
Column: Phenomenex Luna C18 (trade name; manufactured by Phenomenex Co.; size: 4.6×150 mm)
Mobile phase: 0.1% trifluoroacetic acid/acetonitrile=20/80 to 0/100 (17 minutes, linear gradient)
Flow rate: 1.0 mL/min.
Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C18 Cartridges manufactured by Waters: the packed amount of the packing agent: 130 mg) so that the column adsorbs and collects 2-[4'-(3"-fluoropropoxy)phenyl]-6-[$^{125}$I]iodoimidazo[1,2-a]pyridine. The column was rinsed with 1 mL of water, and then 1 mL of ethanol was passed therethrough to elute 2-[4'-(3"-fluoropropoxy)phenyl]-6-[$^{125}$I]iodoimidazo[1,2-a]pyridine. The amount of radioactivity of the obtained compound was 5.5 MBq (at the end of synthesis). Further, the TLC analysis was conducted under the following conditions, and as a result, the radiochemical purity of the compound was 96.0%.

TLC analysis conditions:
TLC plate: RP-18F254 (trade name; manufactured by Merck & Co., Inc.)
Mobile phase: methanol/water=20/1
Detector: Bio-imaging Analyzer, BAS-2500 (type: BAS-2500 manufactured by FUJIFILM Corporation)

Example I-3

Synthesis of 2-[4'-(3"-fluoropropoxy)phenyl]-6-[$^{123}$I]iodoimidazo[1,2-a]pyridine To 70 µL of a solution of 6-tributylstannyl-2-[4'-(3"-fluoropropoxy)phenyl]imidazo[1,2-a]pyridine in methanol (concentration: 1 mg/mL), 100 µL of 1 mol/L hydrochloric acid, [$^{123}$I]sodium iodide of 260-330 MBq (30-60 µL in volume), 20 µL of 1 mmol/L sodium iodide solution and 20 µL of 10% (w/v) hydrogen peroxide were added. After the mixed solution was heated at 50° C. for 10 minutes, the solution was subjected to HPLC under the same conditions as in Example I-2, to obtain 2-[4'-(3"-fluoropropoxy)phenyl]-6-[$^{123}$I]iodoimidazo[1,2-a]pyridine as a fraction.

10 ml of water was added to the fraction. The resulting solution was passed through a reversed phase column (trade name: Sep-Pak (registered trademark) Light C18 Cartridges manufactured by Waters: the packed amount of the packing agent: 130 mg) so that the column adsorbs and collects 2-[4'-(3"-fluoropropoxy)phenyl]-6-[$^{123}$I]iodoimidazo[1,2-a]pyridine. The column was rinsed with 1 mL of water, and then 1 mL of ethanol was passed therethrough to elute 2-[4'-(3"-fluoropropoxy)phenyl]-6-[$^{123}$I]iodoimidazo[1,2-a]pyridine. The amount of radioactivity of the obtained compound was 112-153 MBq at the end of synthesis. Further, the TLC analysis was conducted under the same conditions as in Example I-2, and as a result, the radiochemical purity of the compound was 97.0%.

Example I-4

Synthesis of 6-bromo-2-[4'-(3"-p-toluenesulfonyloxypropoxy)phenyl]imidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-2, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 1-2, Step 2).

1.45 g (corresponding to 5.0 mmol) of 6-bromo-2-(4'-hydroxyphenyl)imidazo[1,2-a]pyridine that was sufficiently dried to remove moisture was dissolved in 50 mL of N,N-dimethylformamide, and 2.07 g (corresponding to 15.0 mol) of potassium carbonate was added thereto. The mixture was supplemented with 680 µL (corresponding to 7.5 mmol) of 3-bromo-1-propanol, and then the solution was stirred at room temperature for 17 hours. After the completion of the reaction, the reaction solution was poured into water and extracted three times with chloroform. The combined chloroform layer was washed with a saturated sodium chloride solution, dried over anhydrous sodium sulfate, filtered and concentrated. The resulting crude product was recrystallized from methanol to obtain 1.28 g (corresponding to 3.67 mmol) of 6-bromo-2-[4'-(3"-hydroxypropoxy)phenyl]imidazo[1,2-a]pyridine (FIG. 1-2, Step 3).

177 mg (corresponding to 0.5 mmol) of 6-bromo-2-[4'-(3"-hydroxypropoxy)phenyl]imidazo[1,2-a]pyridine was dissolved in 10 mL of pyridine, and 197 mg (corresponding to 1.0 mmol) of p-toluenesulfonylchloride was added under an ice bath. After the reaction solution was stirred at room temperature for 16 hours, it was poured into water and extracted three times with chloroform. The combined chloroform layer was washed with a saturated sodium chloride solution, dried over anhydrous sodium sulfate, filtered and concentrated. The resulting crude product was purified by recycle preparative HPLC(HPLC apparatus: LC-908 (under trade name: manufactured by Japan Analytical Industry Co., Ltd.); column: two JAIGEL 2H (under trade name; manufactured by Japan Analytical Industry Co., Ltd.) connected together; mobile phase: chloroform), to obtain 87 mg (corresponding to 0.17 mmol) of 6-bromo-2-[4'-(3"-p-toluenesulfonyloxypropoxy)phenyl]imidazo[1,2-a]pyridine (FIG. 1-2, Step 4).

The NMR measurement results of the resulting 6-bromo-2-[4'-(3"-p-toluenesulfonyloxypropoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.26-8.24 (m, 1H), 7.84-7.80 (m, 2H), 7.77-7.74 (m, 2H), 7.74 (s, 1H), 7.50 (d, J=9.7 Hz, 1H), 7.26-7.23 (m, 2H), 7.21 (dd, J=9.7, 2.0 Hz, 1H), 6.84-6.80 (m, 2H), 4.26 (t, J=6.0 Hz, 2H), 3.98 (t, J=6.0 Hz, 2H), 2.35 (s, 3H), 2.13 (quint., J=6.0 Hz, 2H).

$^{13}$C-NMR (solvent: chloroform-dl, resonance frequency: 125 MHz): δ 158.67, 146.53, 144.79, 144.08, 132.77, 129.80, 127.87, 127.81, 127.28, 126.20, 125.43, 117.87, 114.63, 107.40, 106.76, 66.97, 63.08, 28.85, 21.60.

Example I-5

Synthesis of 6-bromo-2-[4'-(3"-[$^{18}$F]fluoropropoxy)phenyl]imidazo[1,2-a]pyridine

[$^{18}$F] ion-containing H$_2^{18}$O (radioactivity: 4210 MBq, a value converted at the beginning of synthesis) was passed through a Sep-Pak Light QMA (under trade name; manufactured by Waters) to adsorb and collect [$^{18}$F]fluoride ions. Then, a potassium carbonate solution (66.7 mmol/L, 0.3 mL) and 1.5 mL of a solution of 20 mg (corresponding to 53.2 µmol) of Kryptofix 222 (under trade name; manufactured by Merck Co., Ltd.) in acetonitrile were passed through the column to elute the [$^{18}$F] fluoride ions.

The eluate was heated under helium gas stream to 100° C. to evaporate water, and supplemented with acetonitrile (0.3 mL×2) and azeotropically distilled to dryness. To this, 1.0 mL of a solution of 5' mg (corresponding to 10.0 µmol) of 6-bromo-2-[4'-(3"-p-toluenesulfonyloxypropoxy)phenyl] imidazo[1,2-a]pyridine synthesized above in Example I-4 in dimethylformamide was added thereto, and heated at 130° C. for 10 minutes. After the reaction solution was cooled down to 30° C., it was passed through a Sep-Pak Plus Silica (trade name; Waters) each time the reaction solution was supplemented with ether (3.5 mL×3). The ether solution that had been passed was heated to 60° C. under helium gas stream and concentrated. The concentrated solution was diluted with 2 mL of a mixed solution of methanol/water/triethylamine=800:200:1.

The resulting solution was purified by HPLC (column: Capcell Pak C18 MG (15 mm i.d.×250 mm, manufactured by Shiseido Co., Ltd.); elution solvent: methanol/water/triethylamine=700/300/1). An eluate fraction containing the target compound is diluted with 100 mL of water, and then passed through a Sep-Pak Plus C18 (trade name, manufactured by Waters) to adsorb and collect the target compound. Then, 20 mL of water was passed through the column to wash it. Then, 4 mL of ethanol was passed through the column to elute a solution of 6-bromo-2-[4'-(3"-[$^{18}$F]fluoropropoxy)phenyl]imidazo[1,2-a]pyridine in ethanol. The obtained radioactivity level was 769 MBq (107 min. after the beginning of synthesis). According to the TLC analysis on the following conditions, the radiochemical purity thereof was 95.9%.

TLC analysis conditions:
TLC plate: Silica Gel 60 $F_{254}$ (trade name; manufactured by Merck & Co., Inc.)
Mobile phase: Chloroform/methanol/triethylamine=500/10/0.5
Detector: Rita Star (trade name; manufactured by raytest)

Example I-6

Synthesis of 6-bromo-2-[4'-(2"-p-toluenesulfonyloxyethoxy)phenyl]imidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-3, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 1-3, Step 2).

621 mg (corresponding to 10.0 mmol) of ethylene glycol was dissolved in 100 mL of methylene chloride. To this solution under an ice bath, 3.49 g (corresponding to 15.0 mmol) of silver oxide, 350 mg (corresponding to 2.1 mmol) of potassium iodide and 2.10 g (corresponding to 11.0 mmol) of p-toluenesulfonylchloride were added. The resulting mixture was stirred at 0° C. for 2 hours. Insoluble matters were filtered out of the reaction mixture, and were washed with ethyl acetate. The washings were combined with the filtrate, and the mixture was concentrated. The resulting crude product was purified by flash silica gel column chromatography (elution solvent: hexane/ethyl acetate=1/1) to obtain 643 mg (corresponding to 2.97 mmol) of 2-hydroxyethyl-p-toluenesulfonate (FIG. 1-3, Step 3).

To 10 mL of a solution of 639 mg (corresponding to 2.95 mmol) of 2-hydroxyethyl-p-toluenesulfonate in tetrahydrofuran, 388 mg (corresponding to 1.34 mmol) of 6-bromo-2-(4'-hydroxyphenyl)imidazo[1,2-a]pyridine and 780 mg (corresponding to 2.97 mmol) of triphenylphosphine were added. Further, 6 mL of N,N-dimethylformamide was added thereto to completely dissolve the contents. To the reaction mixture, 0.58 mL (corresponding to 2.95 mmol) of diisopropylazodicarboxylate was added. After the reaction mixture was stirred at room temperature for 17 hours, the reaction solution was concentrated. The resulting crude product was purified by flash silica gel column chromatography (elution solvent: hexane/ethyl acetate=65/35). Insoluble matter in chloroform was filtered out of fractions containing a target compound. Further, the resulting crude product was purified by recycle preparative HPLC(HPLC apparatus: LC-908 (under trade name; manufactured by Japan Analytical Industry Co., Ltd.); column: two JAIGEL 2H (under trade name; manufactured by Japan Analytical Industry Co., Ltd.) connected together; mobile phase: chloroform), to obtain 79.7 mg (corresponding to 164 μmol) of 6-bromo-2-[4'-(2"-p-toluenesulfonyloxyethoxy)phenyl]imidazo[1,2-a]pyridine (FIG. 1-3, Step 4).

The NMR measurement results of the resulting 6-bromo-2-[4'-(2"-p-toluenesulfonyloxyethoxy)phenyl]imidazo[1,2-a]pyridine are shown below.

NMR apparatus employed: JNM-ECP-500 (manufactured by Japan Electron Optics Laboratory Co., Ltd. (JEOL))

$^{1}$H-NMR (solvent: dimethylformamide-d7, resonance frequency: 500 MHz): δ 8.73-8.71 (m, 1H), 8.19-8.17 (m, 1H), 7.81-7.77 (m, 2H), 7.73-7.70 (m, 2H), 7.41-7.38 (m, 1H), 7.39-7.36 (m, 2H), 7.20 (dd, J=9.5, 1.9 Hz), 6.85-6.81 (m, 2H), 4.34-4.31 (m, 2H), 4.19-4.15 (m, 2H).

$^{13}$C-NMR (solvent: dimethylformamide-d7, resonance frequency: 125 MHz): δ 158.32, 145.91, 145.24, 143.84, 133.15, 130.18, 127.83, 127.54, 127.19, 127.15, 126.90, 117.56, 114.86, 108.73, 105.80, 69.28, 65.88, 20.69.

Reference Example I-1

Synthesis of 6-bromo-2-[4'-(3"-fluoropropoxy)phenyl]imidazo[1,2-a]pyridine (Non-radioactive Fluorinated Form)

As a sample for evaluating affinity with amyloid, solubility in fat and mutagenicity of the present compound, a non-radioactive fluorinated form of 6-bromo-2-[4'-(3"-fluoropropoxy)phenyl]imidazo[1,2-a]pyridine was synthesized.

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-4, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 1-4, Step 2).

290 mg (corresponding to 1.0 mmol) of 6-bromo-2-(4'-hydroxyphenyl)imidazo[1,2-a]pyridine that was sufficiently dried to remove moisture was dissolved in 10 mL of N,N-dimethylformamide, and 413 mg (corresponding to 3.0 mmol) of potassium carbonate was added thereto. The mixture was supplemented with 138 μL (corresponding to 1.5 mmol) of 1-bromo-3-fluoropropane, and then was stirred at room temperature for 20.5 hours. After the completion of the reaction, the reaction solution was poured into water and extracted three times with chloroform. The combined chloroform layer was washed with a saturated sodium chloride solution, dried over anhydrous sodium sulfate, filtered and concentrated. The resulting crude product was purified by recycle preparative HPLC(HPLC apparatus: LC-908 (under trade name; manufactured by Japan Analytical Industry Co., Ltd.); column: two JAIGEL 2H (under trade name; manufactured by Japan Analytical Industry Co., Ltd.) connected together; mobile phase: chloroform), to obtain 302 mg (corresponding to 0.866 mmol) of 6-bromo-2-[4'-(3"-fluoropropoxy)phenyl]imidazo[1,2-a]pyridine (FIG. 1-4, Step 3).

The NMR measurement results of the resulting 6-bromo-2-[4'-(3"-fluoropropoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.23 (dd, J=1.9, 0.2 Hz, 1H), 7.88-7.83 (m, 2H), 7.51-7.48 (m, 1H), 8.21 (dd, J=9.5, 1.9 Hz, 1H), 6.99-6.95 (m, 2H), 4.67 (dt, $^2J_{HF}$=47.1 Hz, J=5.9 Hz, 2H), 4.15 (t, J=5.9 Hz, 2H), 2.19 (dquint, $^3J_{HF}$=25.9 Hz, J=5.9 Hz, 2H).

$^{13}$C-NMR (solvent: chloroform-dl, resonance frequency: 125 MHz): δ 159.01, 146.61, 144.07, 127.81, 127.38, 126.15, 125.41, 117.87, 114.78, 107.41, 106.71, 80.71 (d, $^1J_{CF}$=164.6 Hz), 63.59 (d, $^3J_{CF}$=5.3 Hz), 30.43 (d, $^2J_{CF}$=19.7 Hz).

$^{19}$F-NMR (solvent: chloroform-dl, resonance frequency: 470 MHz): δ −222.07 (dd, $^2J_{HF}$=47.1 Hz, $^3J_{HF}$=25.9 Hz).

Reference Example I-2

Synthesis of 2-[4'-(3"-fluoropropoxy)phenyl]-6-iodoimidazo[1,2-a]pyridine (Non-radioactive Fluorinated Form)

As a sample for evaluating affinity with amyloid, solubility in fat and mutagenicity of the present compounds, a non-radioactive fluorinated form of 2-[4'-(3"-fluoropropoxy)phenyl]-6-iodoimidazo[1,2-a]pyridine was synthesized.

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-5, Step 1).

441 mg (corresponding to 2.0 mmol) of 2-bromo-4'-hydroxyacetophenone and 449 mg (corresponding to 2.0 mmol) of 2-amino-5-iodopyridine were dissolved in 15 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 526 mg (corresponding to 1.56 mmol) of 2-(4'-hydroxyphenyl)-6-iodoimidazo[1,2-a]pyridine (FIG. 1-5, Step 2).

673 mg (corresponding to 2.0 mmol) of 2-(4'-hydroxyphenyl)-6-iodoimidazo[1,2-a]pyridine that was sufficiently dried to remove moisture was dissolved in 25 mL of N,N-dimethylformamide, and 831 mg (corresponding to 6.0 mmol) of potassium carbonate was added thereto. The mixture was supplemented with 275 μL (corresponding to 3.0 mmol) of 1-bromo-3-fluoropropane, and then stirred at room temperature for 24 hours. After the completion of the reaction, the reaction solution was poured into water and extracted three times with chloroform. The combined chloroform layer was washed with water and a saturated sodium chloride solution, dried over anhydrous sodium sulfate, filtered and concentrated. The resulting crude product was purified by flash silica gel column chromatography (elution solvent: chloroform), and further by recycle preparative HPLC(HPLC apparatus: LC-908 (under trade name; manufactured by Japan Analytical Industry Co., Ltd.); column: two JAIGEL 2H (under trade name; manufactured by Japan Analytical Industry Co., Ltd.) connected together; mobile phase: chloroform), to obtain 349 mg (corresponding to 0.881 mmol) of 2-[4'-(3"-fluoropropoxy)phenyl]-6-iodoimidazo[1,2-a]pyridine (FIG. 1-5, Step 3).

The NMR measurement results of the resulting 2-[4'-(3"-fluoropropoxy)phenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.37-8.35 (m, 1H), 7.88-7.84 (m, 2H), 7.72 (s, 1H), 7.42-7.39 (m, 1H), 7.32 (dd, J=9.4, 1.6 Hz, 1H), 6.99-

6.96 (m, 2H), 4.67 (dt, $^2J_{HF}$=47.0 Hz, J=6.0 Hz, 2H), 4.15 (t, J=6.0 Hz, 2H), 2.20 (dquint, $^3J_{HF}$=25.9 Hz, J=6.0 Hz, 2H).

$^{13}$C-NMR (solvent: chloroform-dl, resonance frequency: 125 MHz): δ 159.01, 146.23, 144.16, 132.36, 130.28, 127.42, 126.05, 118.31, 114.77, 106.90, 80.72 (d, $^1J_{CF}$=164.6 Hz), 74.80, 63.57 (d, $^3J_{CF}$=5.3 Hz), 30.42 (d, $^2J_{CF}$=20.2 Hz).

$^{19}$F-NMR (solvent: chloroform-dl, resonance frequency: 470 MHz): δ −222.09 (dd, $^2J_{HF}$=47.0 Hz, $^3J_{HF}$=25.9 Hz).

Reference Example I-3

Synthesis of 6-bromo-2-[4'-(2''-fluoroethoxy)phenyl]imidazo[1,2-a]pyridine (Non-radioactive Fluorinated Form)

As a sample for evaluating affinity with amyloid, solubility in fat and mutagenicity of the present compounds, a non-radioactive fluorinated form of 6-bromo-2-[4'-(2''-fluoroethoxy)phenyl]imidazo[1,2-a]pyridine was synthesized.

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-6, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 1-6, Step 2).

578 mg (corresponding to 2.0 mmol) of 6-bromo-2-(4'-hydroxyphenyl)imidazo[1,2-a]pyridine that was sufficiently dried to remove moisture was dissolved in 20 mL of N,N-dimethylformamide, and 830 mg (corresponding to 6.0 mmol) of potassium carbonate was added thereto. The mixture was supplemented with 510 μL (corresponding to 3.0 mmol) of 2-fluoroethyl-p-toluenesulfonate, and then the solution was stirred at room temperature for 44.5 hours. After the completion of the reaction, the reaction solution was poured into water and extracted three times with chloroform. The combined chloroform layer was washed with water and a saturated sodium chloride solution, dried over anhydrous sodium sulfate, filtered and concentrated. The resulting crude product was purified by flash silica gel column chromatography (elution solvent: chloroform/methanol=100/1), by recycle preparative HPLC (HPLC apparatus: LC-908 (under trade name; manufactured by Japan Analytical Industry Co., Ltd.); column: two JAIGEL 2H (under trade name; manufactured by Japan Analytical Industry Co., Ltd.) connected together; mobile phase: chloroform), and further by preparative TLC (elution solvent: chloroform/methanol=50:1) to obtain 446 mg (corresponding to 1.33 mmol) of 6-bromo-2-[4'-(2''-fluoroethoxy)phenyl]imidazo[1,2-a]pyridine (FIG. 1-6, Step 3).

The NMR measurement results of the resulting 6-bromo-2-[4'-(2''-fluoroethoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.23-8.21 (m, 1H), 7.87-7.84 (m, 1H), 7.72 (s, 1H), 7.51-7.47 (m, 1H), 7.20 (dd, J=9.5, 1.9 Hz, 1H), 7.01-6.97 (m, 2H), 4.84-4.71 (m, 2H), 4.30-4.21 (m, 2H).

$^{13}$C-NMR (solvent: chloroform-dl, resonance frequency: 125 MHz): δ 158.62, 146.46, 144.06, 127.85, 127.41, 126.58, 125.42, 117.87, 114.91, 107.49, 106.74, 81.86 (d, $^1J_{CF}$=170.8 Hz), 67.15 (d, $^2J_{CF}$=20.2 Hz).

$^{19}$F-NMR (solvent: chloroform-dl, resonance frequency: 470 MHz): δ −223.80 (dd, $^2J_{HF}$=47.4 Hz, $^3J_{HF}$=27.6 Hz).

Reference Example I-4

Synthesis of 2-[4'-(2''-fluoroethoxy)phenyl]-6-iodoimidazo[1,2-a]pyridine (Non-radioactive Fluorinated Form)

As a sample for evaluating affinity with amyloid, solubility in fat and mutagenicity of the present compounds, a non-radioactive fluorinated form of 2-[4'-(2''-fluoroethoxy)phenyl]-6-iodoimidazo[1,2-a]pyridine was synthesized.

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-7, Step 1).

441 mg (corresponding to 2.0 mmol) of 2-bromo-4'-hydroxyacetophenone and 449 mg (corresponding to 2.0 mmol) of 2-amino-5-iodopyridine were dissolved in 15 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 526 mg (corresponding to 1.56 mmol) of 2-(4'-hydroxyphenyl)-6-iodoimidazo[1,2-a]pyridine (FIG. 1-7, Step 2).

368 mg (corresponding to 1.1 mmol) of 2-(4'-hydroxyphenyl)-6-iodoimidazo[1,2-a]pyridine that was sufficiently dried to remove moisture was dissolved in 15 mL of N,N-dimethylformamide, and 453 mg (corresponding to 3.3 mmol) of potassium carbonate was added thereto. The mixture was supplemented with 280 µL (corresponding to 1.6 mmol) of 2-fluoroethyl-p-toluenesulfonate, and then the solution was stirred at room temperature for 22 hours. After the completion of the reaction, the reaction solution was poured into water and extracted three times with chloroform. The combined chloroform layer was washed with water and a saturated sodium chloride solution, dried over anhydrous sodium sulfate, filtered and concentrated. The resulting crude product was purified by flash silica gel column chromatography (elution solvent: hexane/ethyl acetate=1/1), and further by recycle preparative HPLC (HPLC apparatus: LC-908 (under trade name; manufactured by Japan Analytical Industry Co., Ltd.); column: two JAIGEL 2H (under trade name; manufactured by Japan Analytical Industry Co., Ltd.) connected together; mobile phase: chloroform), to obtain 222 mg (corresponding to 0.580 mmol) of 2-[4'-(2"-fluoroethoxy)phenyl]-6-iodoimidazo[1,2-a]pyridine (FIG. 1-7, Step 3).

The NMR measurement results of the resulting 2-[4'-(2"-fluoroethoxy)phenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl, resonance frequency: 500 MHz): δ 8.35-8.33 (m, 1H), 7.88-7.84 (m, 2H), 7.70 (s, 1H), 7.39 (d, J=9.4 Hz, 1H), 7.31 (dd, J=9.4, 1.8 Hz, 1H), 7.01-6.97 (m, 2H), 4.84-4.71 (m, 2H), 4.30-4.22 (m, 2H).

$^{13}$C-NMR (solvent: chloroform-dl, resonance frequency: 125 MHz): δ 158.62, 146.08, 144.16, 132.38, 130.30, 127.44, 126.52, 118.30, 114.91, 106.99, 81.86 (d, $^2J_{CF}$=170.8 Hz), 74.82, 67.15 (d, $^3J_{CF}$=20.6 Hz).

$^{19}$F-NMR (solvent: chloroform-dl, resonance frequency: 470 MHz): δ -223.74 (dd, $^2J_{HF}$=47.4 Hz, $^3J_{HF}$=27.7 Hz).

Reference Example I-5

Synthesis of 2-[4'-(3"-fluoropropoxy)phenyl]-6-iodoimidazo[1,2-a]pyridine (Non-radioactive Fluorinated Form)

As a sample for evaluating affinity with amyloid, solubility in fat and mutagenicity of the present compounds, a non-radioactive fluorinated form of 2-[4'-(3"-fluoropropoxy)phenyl]-6-iodoimidazo[1,2-a]pyridine was synthesized.

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-8, Step 1).

646 mg (corresponding to 3.0 mmol) of 2-bromo-4'-hydroxyacetophenone and 668 mg (corresponding to 3.0 mmol) of 2-amino-5-iodopyrimidine were dissolved in 20 mL of acetonitrile. The resulting solution was refluxed in an oil bath at 110° C. for 8 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 15 mL of a saturated sodium hydrogencarbonate solution was added thereto, and the mixture was sonicated for 3 minutes using an ultrasonic washing machine. Precipitates were filtered and recovered from the resulting mixture, sufficiently washed with water, and dried under reduced pressure, to obtain 737 mg (corresponding to 2.19 mmol) of 2-(4'-hydroxyphenyl)-6-iodoimidazo[1,2-a]pyrimidine (FIG. 1-8, Step 2).

339 mg (corresponding to 1.0 mmol) of 2-(4'-hydroxyphenyl)-6-iodoimidazo[1,2-a]pyrimidine that was sufficiently dried to remove moisture was dissolved in 20 mL of N,N-dimethylformamide, and 414 mg (corresponding to 3.0 mmol) of potassium carbonate was added thereto. The mixture was supplemented with 138 µL (corresponding to 1.5 mmol) of 1-bromo-3-fluoropropane, and then stirred at room temperature for 22 hours. After the completion of the reaction, the reaction solution was poured into water and extracted three times with chloroform. The combined chloroform layer was washed with a saturated sodium chloride solution, dried over anhydrous sodium sulfate, filtered and concentrated. The resulting crude product was recrystallized from N,N-dimethylformamide to obtain 236 mg (corresponding to 0.594 mmol) of 2-[4'-(3"-fluoropropoxy)phenyl]-6-iodoimidazo[1,2-a]pyrimidine (FIG. 1-8, Step 3).

The NMR measurement results of the resulting 2-[4'-(3"-fluoropropoxy)phenyl]-6-iodoimidazo[1,2-a]pyrimidine (internal standard: dimethylsulfoxide) are shown below.

NMR apparatus employed: JNM-ECP-500 (manufactured by Japan Electron Optics Laboratory Co., Ltd. (JEOL))

$^1$H-NMR (solvent: dimethylsulfoxide-d6, resonance frequency: 500 MHz): δ 9.27 (d, J=2.3 Hz, 1H), 8.55 (d, J=2.3 Hz, 1H), 8.15 (s, 1H), 7.94-7.90 (m, 2H), 7.06-7.02 (m, 2H), 4.62 (dt, $^2J_{HF}$=47.2 Hz, J=6.1, 2H), 4.14 (t, J=6.1 Hz, 2H), 2.13 (dquint, $^3J_{HF}$=25.5 Hz, J=6.1 Hz, 2H).

$^{13}$C-NMR (solvent: dimethylsulfoxide-d6, resonance frequency: 125 MHz): δ 159.16, 154.12, 146.54, 146.26, 139.00, 127.60, 126.06, 115.21, 106.52, 81.15 (d, $^1J_{CF}$=161.7 Hz), 74.43, 64.07 (d, $^3J_{CF}$=5.8 Hz), 30.13 (d, $^2J_{CF}$=19.7 Hz).

$^{19}$F-NMR (solvent: dimethylsulfoxide-d6, resonance frequency: 470 MHz): δ -220.13 (tt, $^2J_{HF}$=47.2 Hz, $^3J_{HF}$=25.5 Hz).

Reference Example I-6

Synthesis of [$^{125}$I]-IMPY

[$^{125}$I]-IMPY was synthesized in accordance with the following steps for use in Comparative Examples for evaluation on binding to amyloid In accordance with the method described in a literature (Zhi-Ping Zhuang et al., J. Med. Chem., 2003, 46, p. 237-243), 6-tributylstannyl-2-[4'-(N,N-dimethylamino)phenyl]imidazo[1,2-a]pyridine was synthesized, and dissolved in methanol (concentration: 1 mg/mL). To 53 µL of the resulting solution, 75 µL of 1 mol/L hydrochloric acid, 20 µL of [$^{125}$I] sodium iodide of 13.5 MBq and 10 µL of 100 (w/v) hydrogen peroxide were added. After the mixed solution was left to stand at 50° C. for 10 minutes, the solution was subjected to HPLC under the same condition as described in Example I-2, to obtain [$^{125}$I]-IMPY fraction.

10 ml of water was added to the fraction. The resulting solution was passed through a reverse phase column (trade name: Sep-Pak (registered trademark) Light C18 Cartridges manufactured by Waters; the packed amount of the packing agent: 130 mg), so that the column adsorbs and collects the [$^{125}$I]-IMPY. The column was rinsed with 1 mL of water, and then 1 mL of ethanol was passed therethrough, to elute [$^{125}$I]-IMPY. The obtained radioactivity was 2.6 MBq at the end of synthesis. Further, the TLC analysis was conducted under the same conditions as described in Example I-2, and as a result, the radiochemical purity of the compound was 98.0%.

Reference Example I-7

Synthesis of [$^{123}$I]-IMPY

[$^{123}$I]-IMPY was prepared in accordance with the following steps for use in Comparative Examples for evaluations on log $P_{octanol}$ and accumulation in brain.

In accordance with the method described in a literature (Zhi-Ping Zhuang et al., J. Med. Chem., 2003, 46, p. 237-243), 6-tributylstannyl-2-[4'-(N,N-dimethylamino)phenyl]imidazo[1,2-a]pyridine was synthesized, and dissolved in methanol (concentration: 1 mg/mL). To 53 μL of the resulting solution, 100 μL of 1 mol/L hydrochloric acid, 20-50 μL of [$^{123}$I]sodium iodide of 190-240 MBq, 10 μL of 1 mmol/L sodium iodide and 10 μL of 10% (w/v) hydrogen peroxide were added. After the mixed solution was left to stand at 50° C. for 10 minutes, the solution was subjected to HPLC under the same condition as described in Example I-2, to obtain [$^{123}$I]-IMPY fraction.

10 ml of water was added to the fraction. The resulting solution was passed through a reverse phase column (trade name: Sep-Pak (registered trademark) Light C18 Cartridges manufactured by Waters; the packed amount of the packing agent: 130 mg), so that the column adsorbs and collects the [$^{123}$I]-IMPY. The column was rinsed with 1 mL of water, and then 1 mL of ethanol was passed therethrough, to elute [$^{123}$I]-IMPY. The obtained radioactivity was 47-56 MBq at the end of synthesis. Further, the TLC analysis was conducted under the same conditions as described in Example I-2, and as a result, the radiochemical purity of the compound was 98.0%.

Reference Example I-8

Synthesis of 2-(4'-hydroxyphenyl)-6-[$^{125}$I]iodoimidazo[1,2-a]pyridine

In order to prepare calculation formulas for the calculation of log $P_{HPLC}$, 2-(4'-hydroxyphenyl)-6[$^{125}$I]iodoimidazo[1,2-a]pyridine was synthesized in accordance with the following steps.

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-9, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 1-9, Step 2).

138 mg (corresponding to 0.476 mmol) of 6-bromo-2-(4'-hydroxyphenyl)imidazo[1,2-a]pyridine was dissolved in 20 mL of dioxane, and 2 mL of triethylamine was added thereto. Then, 360 μL (corresponding to 0.713 mmol) of bis(tributyltin) and 20 mg (a catalytic amount) of tetrakis-triphenylphosphine palladium were added thereto. After the reaction mixture was stirred at 90° C. for 22 hours, the solvent was distilled off under reduced pressure. The residue was purified by preparative TLC (elution solvent: hexane/ethyl acetate=1/4). Further, the resulting crude product was purified by recycle preparative HPLC(HPLC apparatus: LC-908 (under trade name: manufactured by Japan Analytical Industry Co., Ltd.); column: two JAIGEL 2H (under trade name; manufactured by Japan Analytical Industry Co., Ltd.) connected together; mobile phase: chloroform), to obtain 47 mg (corresponding to 94.9 μmol) of 6-tributylstannyl-2-(4'-hydroxyphenyl)imidazo[1,2-a]pyridine (FIG. 1-9, Step 3).

To 53 μL of a solution of 6-tributylstannyl-2-(4'-hydroxyphenyl)imidazo[1,2-a]pyridine in methanol (concentration: 1 mg/mL), 75 μL of 1 mol/L hydrochloric acid, 40 μL of [$^{125}$I]sodium iodide of 136 MBq and 10 μL of 10% (w/v) hydrogen peroxide were added. After the mixed solution was left to stand at 50° C. for 10 minutes, the solution was subjected to HPLC under the same condition as in Example I-2, to obtain 2-(4'-hydroxyphenyl)-6-[$^{125}$I]iodoimidazo[1,2-a]pyridine fraction (FIG. 1-9, Step 4).

10 ml of water was added to the fraction. The resulting solution was passed through a reversed phase column (trade name: Sep-Pak (registered trademark) Light C18 Cartridges manufactured by Waters: the packed amount of the packing agent: 130 mg) so that the column adsorbs and collects 2-(4'-hydroxyphenyl)-6-[$^{125}$I]iodoimidazo[1,2-a]pyridine. The column was rinsed with 1 mL of water, and then 1 mL of ethanol was passed therethrough, to elute 2-(4'-hydroxyphenyl)-6-[$^{125}$I]iodoimidazo[1,2-a]pyridine. The obtained radioactivity was 37.5 MBq at the end of synthesis. Further, the TLC analysis was conducted under the same conditions as in Example I-2, and as a result, the radiochemical purity of the compound was 96.5%.

Reference Example I-9

Synthesis of 2-(4'-hydroxyphenyl)-6-iodoimidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1-10, Step 1).

441 mg (corresponding to 2.0 mmol) of 2-bromo-4'-hydroxyacetophenone and 449 mg (corresponding to 2.0 mmol) of 2-amino-5-iodopyridine were dissolved in 15 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 526 mg (corresponding to 1.56 mmol) of 2-(4'-hydroxyphenyl)-6-iodoimidazo[1,2-a]pyridine (FIG. 1-10, Step 2).

The NMR measurement results of the resulting 2-(4'-hydroxyphenyl)-6-iodoimidazo[1,2-a]pyridine (internal standard: dimethylsulfoxide) are shown below.

NMR apparatus employed: JNM-ECP-500 (manufactured by Japan Electron Optics Laboratory Co., Ltd. (JEOL))

$^1$H-NMR (solvent: dimethylsulfoxide-d6, resonance frequency: 500 MHz): δ 8.86-8.84 (m, 1H), 8.14 (s, 1H), 7.78-7.74 (m, 2H), 7.40-7.35 (m, 2H), 6.86-6.82 (m, 2H).

$^{13}$C-NMR (solvent: dimethylsulfoxide-d6, resonance frequency: 125 MHz): δ 158.08, 145.87, 143.87, 132.48, 131.72, 127.67, 124.99, 118.14, 116.14, 108.02, 75.85.

Examples I-7 and Comparative Examples I-1

Measurement of Binding to Amyloid

Affinity of the present compounds with amyloid was examined by the following in vitro binding tests.

(1) $A\beta_{1-40}$ (Peptide Institute, INC.) was dissolved in phosphate buffer (pH 7.4) and shaken at 37° C. for 72 hours, to obtain a 1 mg/mL suspension (hereinafter referred to as amyloid suspension in these Examples) of aggregated (hereinafter referred to as amyloid in this Example).

(2) According to the method described in a literature (Naiki, H., et al., Laboratory Investigation 74, p. 374-383 (1996)), the amyloid suspension was subjected to qualitative experiment based on fluorescence spectrophotometric method using Thioflavin T (manufactured by Fluka) to confirm that the aggregated Aβ obtained in (1) was amyloid (measurement conditions: excitation wavelength of 446 nm, and emission wavelength of 490 nm).

(3) A solution in ethanol of the compound I-6 synthesized by a method described above in Example I-2 (radioactive concentration: 37 MBq/mL) was prepared, and diluted with a 0.1% bovine serum albumin-containing phosphate buffer (pH 7.4) to prepare a solution corresponding to 2 nmol/L as a total amount of 2-[4'-(3"-fluoropropoxy)phenyl]-6-iodoimidazo[1,2-a]pyridine.

(4) To each well of a 96-well microplate, 50 μL of a solution (400 μM at a final concentration) prepared above in (3) and 50 μL of a solution (amyloid concentration may be adjusted in accordance with amyloid concentration in a sample solution) where amyloid suspension was dissolved in a 0.1% bovine serum albumin-containing phosphate buffer (pH 7.4), were added, and then 150 μL of the same buffer was added to prepare a solution of amyloid at final concentrations of 2.5, 12.5, 25, 62.5, 125, 250, 625, and 1000 nmol/L.

(5) The microplate was shaken at a given rate (400 rpm) at 22° C. for 3 hours. Then, a mixed solution of each well was filtered through a glass fiber filter (trade name: Mulutiscreen™-FC, manufactured by Millipore), to separate the Compound I-6 attached to amyloid from the free Compound I-6.

(6) The glass fiber filter used for filtration of the mixed solution was washed with a 0.1% bovine serum albumin-containing phosphate buffer (0.5 mL×5), and then radioactivity of the glass fiber filter was measured with an autowell gamma system (manufactured by Aloka, Type: ARC-301B).

(7) A relation between the amount of the Compound I-6 binding to amyloid and the amount of added amyloid was evaluated from the measurement results of (6). Unspecific binding was determined using a sample to which the Compound I-2 (non-RI labeled compound) was added to become 100 nM (at a final concentration) above in (4) (Example I-7).

(8) Using [$^{125}$I]-IMPY synthesized in the above Reference Example I-6, the same procedure as the above (2) to (6) were carried out to obtain control data (Comparative Example I-1).

A relation between the concentration of amyloid in the sample solution and the radioactive count on the glass fiber filter measured above in (6) is shown in FIG. 1-11. The radioactivity on the glass fiber was increased proportionally to the concentration (addition amount) of amyloid (Example I-7). On the conditions of the present experiment, amyloid and the compound attached to amyloid are retained in the glass fiber. Therefore, the radioactive count on the glass fiber is a value reflecting the amount of the compound attached to amyloid, and the slope of the graph which plotted the radioactive count relative to the concentration of amyloid is a value which can be an index representing the intensity of binding to amyloid. Since the value of the radioactive count of Compound I-6 on the glass fiber was increased with increase of the concentration of amyloid, it has been suggested that Compound I-6 is a compound having a property of binding to amyloid. The slope of the line for Compound I-6 was greater than the slope for [$^{125}$I]-IMPY in the same plot, and thus it has been suggested that the affinity of Compound I-6 with amyloid is stronger than [$^{125}$I]-IMPY which is known to exhibit a strong affinity with amyloid.

The above-mentioned results have implied that Compound I-6 is highly capable of binding to amyloid.

Examples I-8 to I-12, Comparative Examples I-2 to I-6

Measurement of Affinity with Amyloid

Affinity of the present compounds with amyloid was examined by the following in vitro binding tests.

(1) $A\beta_{1-40}$ (Peptide Institute, INC.) was dissolved in phosphate buffer (pH 7.4) and shaken at 37° C. for 62-72 hours, to obtain a 1 mg/mL suspension of aggregated Aβ (hereinafter referred to as amyloid suspension in this Example).

(2) According to the method described in a literature (Naiki, H., et al., Laboratory Investigation 74, p. 374-383 (1996)), the amyloid suspension was subjected to qualitative experiment based on fluorescence spectrophotometric method using Thioflavin T (manufactured by Fluka) to confirm that the aggregated Aβ obtained in (1) was amyloid (measurement conditions: excitation wavelength of 446 nm, and emission wavelength of 490 nm).

(3) According to the method described in a literature (Wang, Y., et al., J. Labeled Compounds Radiopharmaceut. 44, 5239 (2001)), [$^{125}$I]2(3'-iodo-4'-aminophenyl)benzothiazole (hereinafter referred to as [$^{125}$I]3'-I-BTA-0) was prepared from a labeling precursor 2-(4'-aminophenyl)benzothiazole, and dissolved in ethanol. As Congo Red, Thioflavin T and 6-methyl-2-[4'-(N,N-dimethylamino)phenyl]benzothiazole (hereinafter referred to as 6-Me-BTA-2), commercially available reagents were weighed and used as they were.

(4) 2-(3'-Iodo-4'-aminophenyl)benzothiazole (hereinafter referred to as 3'-I-BTA-0) and IMPY were synthesized according to the methods described in a literature (Wang. Y., et al., J. Labelled Compounds Radiopharmaceut. 44, 5239 (2001)) and a literature (Zhuang, Z. P., et al., J. Med. Chem. 46, 237 (2003)) respectively.

(5) Samples in which [$^{125}$I]3'-I-BTA-0, each compound for evaluation and amyloid were dissolved in a 0.1% bovine serum albumin-containing phosphate buffer (pH 7.4) at final concentrations shown in Table 1-2 were prepared. The resulting samples were filled in each well (about 0.3 mL in volume) of a 96-well microplate.

TABLE 1-2

Final concentrations of each compound in sample solutions

| Experiment | Compound for evaluation | Concentration of compound for evaluation | [$^{125}$I]3'-I-BTA-0 concentration | Amyloid |
|---|---|---|---|---|
| Comparative Example I-2 | 3'-I-BTA-0 | Each concentration of 0, 0.001, 0.01, 0.1, 1, 10, 100, and 1000 nmol/L | 400 pmol/L | 1 μmol/L |
| Comparative Example I-3 | Congo Red | | | |
| Comparative Example I-4 | Thioflavin T | | | |
| Comparative Example I-5 | 6-Me-BTA-2 | | | |
| Comparative Example I-6 | IMPY | | | |
| Example I-8 | Compound I-1 | | | |
| Example I-9 | Compound I-2 | | | |
| Example I-10 | Compound I-3 | | | |
| Example I-11 | Compound I-4 | | | |
| Example I-12 | Compound I-5 | | | |

(6) The microplate filled with the sample solutions was shaken at a given rate (400 rpm) at 22° C. for 3 hours. Then, each sample solution was filtered through a glass fiber filter (trade name: Mulutiscreen™-FC, manufactured by Millipore), to separate the [$^{125}$I]3'-I-BTA-0 attached to amyloid from the free [$^{125}$I]3'-I-BTA-0.

(7) The glass fiber filter used for the filtration of each sample solution was washed with a 0.1% bovine serum albumin-containing phosphate buffer (pH 7.4) (0.5 mL×5), and radioactivity of the glass fiber filter was measured with an autowell gamma system (manufactured by Aloka, Type: ARC-301B). The radioactivity was used as the radioactivity level of each sample solution for calculating an inhibition ratio (hereinafter, A denotes the radioactivity level in a sample with zero (0) concentration of each compound for evaluation, and B denotes the radioactivity level in a sample with 0.001 nmol/L or higher concentration of each compound for evaluation).

(8) Separately, a solution of containing 15 μmol/L of 6-Me-BTA-2, 400 pmol/L of [$^{125}$I]3'-I-BTA-0 and 1 μmol/L of Aβ$_{1-40}$ were prepared and subjected to the same procedures as described above in (6) and (7) to measure a radioactivity level. The measured radioactivity level was defined as the background radioactivity level, and used in the calculation of the inhibition ratio (hereinafter referred to as BG).

(9) Using the radioactivity levels measured above in (7) and (8), the inhibition ratio was determined by the following formula (1-1).

$$\frac{B - BG}{A - BG} \times 100 \ (\%) \tag{1-1}$$

A graph in which values converted by probit transformation from the obtained inhibition ratios were plotted relative to logarithms of concentrations of compounds for evaluation was prepared to obtain an approximate straight line by the least square method. Using the line, the concentration of each compound for evaluation was determined, at which the radioactivity level is half of the level of the sample free from each compound for evaluation, and was defined as a 50% inhibition concentration of each compound (hereinafter referred to as IC$_{50\%}$ value). Using the value as an indicator, affinity of each compound for evaluation with amyloid (aggregated Aβ$_{1-40}$) was evaluated.

IC$_{50\%}$ value of each compound for evaluation is shown in Table 1-3. Compounds I-1 to I-5 all showed IC$_{50\%}$ values of less than 100 and had higher affinity with amyloid (aggregated Aβ$_{1-40}$ than Congo Red and Thioflavin T. The results show that Compounds I-1 to I-5 have good affinity with amyloid (aggregated Aβ$_{1-40}$). In particular, Compounds I-1 to I-4 had higher affinity with amyloid (aggregated Aβ$_{1-40}$ than 3'-1-BTA-0 and 6-Me-BTA-2 and had the affinity comparable to IMPY.

TABLE 1-3

IC$_{50\%}$ values of the present compounds

| Experiment | Compound for evaluation | IC$_{50\%}$ values (nmol/L) |
|---|---|---|
| Comparative Example I-2 | 3'-I-BTA-0 | 10.1 |
| Comparative Example I-3 | Congo Red | >1000 |
| Comparative Example I-4 | Thioflavin T | >1000 |
| Comparative Example I-5 | 6-Me-BTA-2 | 25.4 |
| Comparative Example I-6 | IMPY | 0.8 |
| Example I-8 | Compound I-1 | 1.4 |
| Example I-9 | Compound I-2 | 0.9 |
| Example I-10 | Compound I-3 | 1.8 |
| Example I-11 | Compound I-4 | 0.9 |
| Example I-12 | Compound I-5 | 55.4 |

Example I-13 to I-14, Comparative Example I-7

Measurement of Partition Coefficient Based on the Octanol Extraction Method

Partition coefficients based on the octanol extraction method (hereinafter referred to as log $P_{octanol}$ were measured, which are generally known as an indicator of permeability of compounds through the blood-brain barrier (hereinafter referred to as BBB).

To 2 mL of octanol, 10 μL of a solution containing Compound I-7 (Example I-13) and Compound I-8 (Example I-14) and 2 mL of 10 mmol/L phosphate buffer (pH 7.4) were added, and stirred for 30 seconds. After the mixture was centrifuged with a low-speed centrifuge (2000 rpm×60 min.), the octanol layer and the water layer were sampled each in an amount of 1 mL, and subjected to measurement of radioactivity count with an autowell gamma system (manufactured by Aloka, Type: ARC-301B). Using the obtained radioactivity count, log $P_{octanol}$ was calculated in accordance with the equation (1-2).

$$\log P_{octanol} = \log_{10}\left(\frac{\text{Radioactivity count of octanol layer}}{\text{Radioactivity count of water layer}}\right) \quad (1\text{-}2)$$

The results are shown in Table 1-4. Both Compounds I-7 and I-8 showed log $P_{octanol}$ values between 1 and 3. It is known that compounds permeable to BBB show a log $P_{octanol}$ value between 1 and 3 (Douglas D. Dischino at al., J. Nucl. Med., (1983), 24, p. 1030-1038). Thus, it is implied that both compounds have a BBB permeability comparable to IMPY.

TABLE 1-4 log $P_{octanol}$ value of the present compound

| Experiment | Compound | log $P_{octanol}$ value |
|---|---|---|
| Comparative Example I-7 | [$^{123}$I]-IMPY | 2.1 |
| Example I-13 | Compound I-7 | 2.1 |
| Example I-14 | Compound I-8 | 2.0 |

Example I-15 to I-19, Comparative Example I-8

Measurements of Partition Coefficient Based on HPLC

The partition coefficient by HPLC (hereinafter referred to as log $P_{HPLC}$) was measured by the following method. It is known that the log $P_{HPLC}$ shows the same numerical value at a pH of 7.2 to 7.4 as the log $P_{octanol}$ value which is generally known as an indicator of permeability of compounds to BBB (Franco Lombardo et al., J. Med. Chem., (2000), 43, p. 2922-2927).

First, compounds for evaluation shown in Table 1-5 were dissolved at a concentration of 1 mg/mL in methanol containing 10% dimethylsulfoxide to prepare sample solutions. One μL of the sample solution was subjected to HPLC analysis under the following conditions to determine the elution time ($t_0$) of the solvent and the elution time ($t_R$) of each compound.

TABLE 1-5

Compounds for evaluation in experiments

| Experiment | Compound for evaluation |
|---|---|
| Comparative Example I-8 | IMPY |
| Example I-15 | Compound I-1 |
| Example I-16 | Compound I-2 |
| Example I-17 | Compound I-3 |
| Example I-18 | Compound I-4 |
| Example I-19 | Compound I-5 |

HPLC conditions:
Column: Prodigy ODS (3) (product name; manufactured by phenomenex; size: 4.6×250 mm)
Mobile phase: a mixed solution of 50 mM triethylamine phosphate (pH 7.2)/acetonitrile=40/60
Flow rate: 0.7 mL/min.
Detector: ultraviolet visible absorptiometer (detection wavelength: 282 nm)

Using the obtained $t_0$ and $t_R$, the retention factor (hereinafter referred to as K'$_{HPLC}$ value) of each compound for evaluation was determined according to the following calculation formula (1-3).

$$K'_{HPLC} = (t_R - t_0)/t_0 \quad (1\text{-}3)$$

Separately, 10 μL each of a solution of 2-(4'-hydroxyphenyl)-6-[$^{125}$I]iodoimidazo[1,2-a]pyridine (37 MBq/mL in radioactivity concentration) synthesized above in Reference 1-8 and a solution of Compound I-6 (37 MBq/mL in radioactivity concentration) was added to 2 mL of octanol prepared separately, and 2 mL of 10 mmol/L phosphate buffer (pH 7.4) was further added to the respective solutions. After the individual solutions were stirred for 30 seconds, the solutions were centrifuged at 2,000 rpm for 60 minutes. 1 mL each of the octanol phase and the water phase was fractionated, and the radioactivity was measured by an autowell gamma system (manufactured by Aloka Co., Ltd.: Type ARC-301B). Based on the obtained radioactivity, log $P_{octanol}$ values were calculated according to the above equation (1-2).

Further, a solution of Compound I-2 and 2-(4'-hydroxyphenyl)-6-iodoimidazo[1,2-a]pyridine prepared above in Reference I-9 were each subjected to HPLC analysis in the same manner as described above to determine K'$_{HPLC}$ values in respective compounds.

A graph was prepared, in which the log $P_{octanol}$ values of Compound I-6 and 2-(4'-hydroxyphenyl)-6-[$^{125}$I]iodoimidazo[1,2-a]pyridine are respectively plotted relative to the $\log_{10}$K'$_{HPLC}$ values of Compound I-2 and 2-(4'-hydroxyphenyl)-6-iodoimidazo[1,2-a]pyridine, so that the slope and the intercept on the axis Y of the straight line were determined. Using these values, the following formula (1-4) was determined, provided that the log $P_{octanol}$ value is equal to the log $P_{HPLC}$ value at a pH of 7.2 to 7.4.

$$\log P_{HPLC} = 0.96(\log_{10} K'_{HPLC}) + 1.59 \quad (1\text{-}4)$$

Using K'$_{HPLC}$ obtained for each compound for evaluation, the log $P_{HPLC}$ value of each compound for evaluation was determined according to the above calculation formula (1-4).

The results are shown in Table 1-6. As shown in the Table, the log $P_{HPLC}$ values of Compounds I-1 through I-5 were all between 1 and 3. As mentioned above, it is known that compounds permeable to BBB have a log $P_{octanol}$ value between 1 and 3 (Douglas D. Dischino et al., J. Nucl. Med., (1983), 24, p. 1030-1038). Further, as mentioned above, it is known that the log $P_{HPLC}$ shows the same value at a pH of 7.2 to 7.4 as the log $P_{octanol}$ (Franco Lombardo et al., J. Med. Chem., (2000), 43, p. 2922-2927). The above-mentioned results imply that Compounds I-1 to I-5 have a BBB-permeable property.

TABLE 1-6 log$P_{HPLC}$ value of the present compound

| Experiment | Compound | log$P_{HPLC}$ value |
| --- | --- | --- |
| Comparative Example I-8 | IMPY | 2.1 |
| Example I-15 | Compound I-1 | 2.0 |
| Example I-16 | Compound I-2 | 2.1 |
| Example I-17 | Compound I-3 | 1.9 |
| Example I-18 | Compound I-4 | 1.9 |
| Example I-19 | Compound I-5 | 1.8 |

Example I-20 to I-21, Comparative Example I-9

Measurement of Transferability into Brain and Clearance

Using Compound I-7 (Example I-20) and Compound I-8 (Example I-21), a time course change of radioactive accumulation in brain of male Wistar rats (7-week old) was measured.

0.05 mL (20-30 MBq/mL in radioactive concentration) of a solution of Compound I-7 (Example I-20) in a 10 mg/mL ascorbic acid-containing physiological saline solution, a solution of Compound I-8 (Example I-21) in a 10 mg/mL ascorbic acid-containing physiological saline solution and a solution of [$^{123}$I]-IMPY (Comparative Example I-9) prepared above in Reference Example I-7 in a 10 mg/mL ascorbic acid-containing physiological saline solution were each injected under thiopental anesthesia into the tail vein of the rats. The rats were sacrificed by bleeding from abdominal artery, and brains were removed and subjected to measurement of radioactivity (hereinafter referred to as A in this Example) with an autowell gamma system (Type: ARC-301B manufactured by Aloka Co., Ltd.) and further subjected to measurement of mass of brains 2, 5, 30 and 60 minutes after injection. Also, radioactivity (hereinafter referred to as B in this Example) of 0.05 mL of a 1000-fold diluted solution of the injected solution was measured in the same manner as above. Using these measurement results, radioactive distribution per unit weight of brain (% ID/g) at the respective time points was calculated in accordance with the following formula (I-5).

Three animals were used for Experiment I-20 and Comparative Experiment I-9, and two animals were used for Experiment I-21 at the respective time points.

$$\% \ ID/g = \frac{A}{B \times 1000 \times \text{brain weight}} \times 100 \quad (1\text{-}5)$$

The results are shown in Table 1-7. As shown in Table 1-7, Compounds I-7 and I-8 showed an accumulation higher than [$^{123}$I]-IMPY at the time point of two minutes after the injection, and then showed a tendency to rapidly clear away in 60 minutes. These results suggest that Compounds I-7 and I-8 possess excellent transferability to brain and rapid clearance from brain comparable to [$^{123}$I]-IMPY.

TABLE 1-7

Radioactive distribution in brain of the present compound after intravenous injection (rats)

| | | Radioactive distribution per unit weight (% ID/g) | | | |
| --- | --- | --- | --- | --- | --- |
| | Compound | After 2 min. | After 5 min. | After 30 min. | After 60 min. |
| Example I-20 | Compound I-7 | 1.10 | 0.75 | 0.12 | 0.05 |
| Example I-21 | Compound I-8 | 1.20 | 0.75 | 0.18 | 0.12 |
| Comparative Example I-9 | $^{123}$I-IMPY | 1.02 | 0.99 | 0.20 | 0.08 |

Example I-22

Confirmation of Imaging of Amyloid in Brain

The following experiment was carried out in order to examine whether amyloid in brain can be imaged by the compound of the present invention.

(1) Aβ$_{1-40}$ (manufactured by Peptide Institute, INC.) was dissolved in phosphate buffer (pH 7.4) and shaken at 37° C. for 72 hours, to obtain 1 mg/mL of a suspension of aggregated Aβ (hereinafter referred to as amyloid suspension in this Example).

(2) 25 μL (corresponding to 25 μg) of the amyloid suspension was injected into an amygdaloid nucleus on one side of a male Wistar rat (7-week old). As a control, 25 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) Compound I-7 was dissolved in a 10 mg/mL ascorbic acid-containing physiological saline solution to obtain a sample solution (32 MBq/mL in radioactivity concentration). This solution was injected into the rat through the tail vein (dosage: 0.5 mL, dosed radioactivity: 16 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 1-12b).

FIG. 1-12 shows images by autoradiogram and Thioflavin T staining of the brain slice of the rat to which amyloid was injected intracerebrally. As shown in this figure, a marked accumulation of radioactivity was observed in the amygdaloid nucleus on the side to which the amyloid suspension was injected. From the result of Thioflavin T staining in the site where radioactivity is accumulated, it was confirmed that amyloid was present in the accumulation site. On the other hand, no significant accumulation of radioactivity was observed in the amygdaloid nucleus on the side to which the physiological saline solution was injected, compared with the other sites.

These results suggest that Compound I-7 possesses a property of accumulating on intracerebral amyloid and a capability of imaging intracerebral amyloid.

Example I-23 to I-26

Reverse Mutation Test

In order to examine mutagenicity of Compound I-1, I-2, I-4 and I-5, reverse mutation test using *Salmonella typhimurium* TA98 and TA100 (hereinafter referred to as Ames test) was conducted.

The test was conducted without addition of S9mix and with addition of S9mix. Dimethylsulfoxide was used as a negative control. A positive control was 2-(2-furyl)-3-(5-nitro-2-furyl) acrylamide in case S9mix was not added, and 2-aminoanthracene in case S9mix was added.

The amount of each sample to be added to the test plate was 7 dosages (geometric ratio 4) with the maximum dose being 1250 µg/plate for Compounds I-1 and I-5, and 7 dosages (geometric ratio 3) with the maximum dose being 5000 µg/plate for Compounds I-2 and I-4. After a sample to be examined and a strain (TA98 or TA100), or a sample to be examined, S9mix and the strain were mixed together, the mixture was multilayered using soft agar on a medium of a test plate, and then incubated at 37° C. for 48 hours. Judgment was made by counting the number of reverse mutation colonies on the plate after the incubation, and when the number of reverse mutation colonies was not less than two times the number in negative control and showed concentration-dependent increase, mutagenicity was determined to be positive.

The results are shown in Table 1-8. The numbers of reverse mutation colonies of the respective strains in the group treated with Compounds I-1, I-2, I-4 and I-5 were less than two times the number in the group treated with the negative control, regardless of addition of S9mix and the addition amount of a sample to be examined. From the aforementioned results, it is judged that Compounds I-1, I-2, I-4 and I-5 are negative in the Ames test and have no mutagenicity.

TABLE 1-8

Results of Ames test

| | | Mutagenicity | | | |
|---|---|---|---|---|---|
| | | Without addition of S9mix | | With addition of S9mix | |
| | Compound | TA98 | TA100 | TA98 | TA100 |
| Example I-23 | Compound I-1 | Negative | Negative | Negative | Negative |
| Example I-24 | Compound I-2 | Negative | Negative | Negative | Negative |
| Example I-25 | Compound I-4 | Negative | Negative | Negative | Negative |
| Example I-26 | Compound I-5 | Negative | Negative | Negative | Negative |

Example I-27

Synthesis of 6-tributylstannyl-2-[4'-(2''-fluoroethoxy)phenyl]imidazo[1,2-a]pyridine 88 mg (corresponding to 0.260 mmol) of 6-bromo-2-[4'-(2''-fluoroethoxy)phenyl]imidazo[1,2-a]pyridine obtained in Reference Example I-3 was dissolved in 10.0 mL of dioxane, and 2.0 mL of triethylamine was added thereto. Then, 0.20 mL (corresponding to 0.39 mmol) of bis(tributyltin) and 20.1 mg (a catalytic amount) of tetrakis-triphenylphosphine palladium were added thereto. After the reaction mixture was stirred at 90° C. for 9 hours, the solvent was distilled off under reduced pressure. The residue was purified by flash silica gel column chromatography (elution solvent: hexane/ethyl acetate=4/1) to obtain 71.6 mg (corresponding to 0.131 mmol) of 6-tributylstannyl-2-[4'-(2''-fluoroethoxy)phenyl] imidazo[1,2-a]pyridine (FIG. 1-13, Step 1).

The NMR measurement results of the obtained 6-tributylstannyl-2-[4'-(2''-fluoroethoxy)phenyl]imidazo[1,2-a]pyridine (internal standard: tetramethylsilane) are shown below.

NMR apparatus employed: JNM-ECP-500 (manufactured by Japan Electron Optics laboratory Co., Ltd. (JEOL))

$^{1}$H-NMR (solvent: chloroform-dl; resonance frequency: 500 MHz): δ 7.97 (s, 1H), 7.90 (d, J=8.7 Hz, 2H), 7.58 (d, J=8.7 Hz, 1H), 7.14 (d, J=8.7 Hz, 1H), 6.99 (d, J=8.7 Hz, 2H), 4.77, (dt, J=47.2, 4.1 Hz, 2H), 3.99 (dt, J=28.0, 4.1 Hz, 2H), 1.59-1.53 (m, 6H), 1.39-1.32 (m, 6H), 1.13-1.10 (m, 6H), 0.92 (t, J=7.3 Hz, 9H).

$^{13}$C-NMR (solvent: chloroform-dl, resonance frequency: 500 MHz): δ 158.3, 145.6, 144.9, 131.2, 130.0, 127.4, 121.9, 116.9, 114.9, 106.4, 82.6, 81.3, 67.2, 29.0, 27.3, 13.6, 9.8.

Example I-28

Synthesis of 2-[4'-(2''-fluoroethoxy)phenyl]-6-[$^{123}$I] iodoimidazo[1,2-a]pyridine To 35 µL of a solution of 6-tributylstannyl-2-[4'-(2''-fluoroethoxy)phenyl]imidazo[1,2-a]pyridine in methanol (concentration: 1 mg/mL), 100 µL of 1 mol/L hydrochloric acid, [$^{123}$I]sodium iodide of 614 MBq (100 µL in volume), 10 µL of 1 mol/L sodium iodide solution and 20 µL of 10% (w/v) hydrogen peroxide were added. After the mixed solution was heated at 50° C. for 10 minutes, the solution was subjected to HPLC under the same conditions as in Example I-2, to obtain 2-[4'-(2''-fluoroethoxy)phenyl]-6-[$^{123}$I]iodoimidazo[1,2-a] pyridine fraction.

10 ml of water was added to the fraction. The resulting solution was passed through a reversed phase column (trade name: Sep-Pak (registered trademark) Light C8 Cartridges manufactured by Waters: the packed amount of the packing agent: 130 mg) so that the column adsorbs and collects 2-[4'-(2''-fluoroethoxy)phenyl]-6-[$^{123}$I] The column was rinsed with 1 mL of water, and then 1 mL of ethanol was passed therethrough to elute 2-[4'-(2''-fluoroethoxy)phenyl]-6-[$^{123}$I] iodoimidazo[1,2-a]pyridine. The amount of radioactivity of the obtained compound was 64 MBq at the end of synthesis. Further, the TLC analysis was conducted under the following conditions, and as a result, the radiochemical purity of the compound was 97.0%.

TLC analysis conditions:
TLC plate: Silica Gel 60 F$_{254}$ (trade name; manufactured by Merck & Co., Inc.)
Mobile phase: Chloroform/methanol/triethylamine=100/1/2
Detector: Rita Star (trade name; manufactured by raytest)

Example I-29, Comparative Example I-10

Measurement of Partition Coefficient Based on the Octanol Extraction Method

A diethyl ether solution of Compound I-9 prepared in Example I-28 (Example I-29) and a diethyl ether solution of [$^{123}$I]-IMPY (Comparative Example I-10) were each diluted with a 10 mg/mL ascorbic acid-containing physiological saline solution, and adjusted radioactive concentration to be 20-30 MBq/mL. To 2 mL of octanol, 10 μL each of the prepared sample solutions was added, and 2 mL of a 10 mmol/L phosphate buffer (pH 7.4) was further added, followed by stirring for 30 seconds. After the mixture was centrifuged with a low-speed centrifuge (2000 rpm×60 min.), the octanol layer and the water layer were sampled each in an amount of 1 mL, and subjected to measurement of radioactivity count with an autowell gamma system (Type: ARC-301B, manufactured by Aloka). Using the obtained radioactivity count, log $P_{octanol}$ was calculated in accordance with the equation (1-6).

$$\log P_{octanol} = \log_{10}\left(\frac{\text{Radioactivity count of octanol layer}}{\text{Radioactivity count of water layer}}\right) \quad (1\text{-}6)$$

The results are shown in Table 1-9. Compound I-9 also showed a log $P_{octanol}$ value between 1 and 3. It is known that compounds permeable to BBB show a log $P_{octanol}$ value between 1 and 3 (Douglas D. Dischino et al., J. Nucl. Med., (1983), 24, p. 1030-1038). Thus, it is implied that Compound I-9 has a BBB-permeability comparable to IMPY.

TABLE I-9 log $P_{octanol}$ value of the present compound

| Experiment | Compound | log$P_{octanol}$ value |
|---|---|---|
| Comparative Example I-10 | [$^{123}$I]-IMPY | 2.1 |
| Example I-29 | Compound I-9 | 2.1 |

Example I-30, Comparative Example I-11

Measurement of Transferability into Brain and Clearance (2)

Using Compound I-9, a time course change of radioactive accumulation in brain of male Wistar rats (7-week old) was measured.

A solution of Compound I-9 (Example I-30) and a solution of [$^{123}$I]-IMPY (Comparative Example I-11) prepared above in Reference Example each in a 10 mg/mL ascorbic acid-containing physiological saline solution (20-31 MBq/mL in radioactive concentration) were prepared. 0.05 mL each of these solutions was injected under thiopental anesthesia into the tail vein of respective Wistar rats (7-week old). The rats were sacrificed by bleeding from abdominal artery, and brains were removed and subjected to measurement of mass of brains and further subjected to measurement of radioactivity (hereinafter referred to as A in this Example) with a single channel analyzer (detector type: SP-20 manufactured by OHYO KOKEN KOGYO Co., Ltd.) 2, 5, 30 and 60 minutes after the injection. Also, radioactivity (hereinafter referred to as B in this Example) of the rest of the whole body was measured in the same manner as above. Using these measurement results, radioactive distribution per unit weight of brain (% ID/g) at the respective time points were calculated in accordance with the following formula (1-7).

Three animals were used for experiment at the respective time points.

$$\% \; ID/g = \frac{A}{B \times \text{brain weight}} \times 100 \quad (1\text{-}7)$$

The results are shown in Table 1-10. As shown in Table 1-10, Compound I-9 showed a significant radioactive accumulation like [$^{123}$I]-IMPY at the time point of two minutes after the injection, and then showed a tendency to rapidly clear away in 60 minutes. These results suggest that Compound I-9 possesses excellent transferability to brain and rapid clearance from brain like [$^{123}$I]-IMPY.

TABLE 1-10

Radioactive distribution in brain of the present compound after intravenous injection (rats)

| | | Radioactive distribution per unit weight (% ID/g) | | | |
|---|---|---|---|---|---|
| Compound | | After 2 min. | After 5 min. | After 30 min. | After 60 min. |
| Example I-30 | Compound I-9 | 0.72 | 0.49 | 0.07 | 0.02 |
| Comparative Example I-11 | $^{123}$I-IMPY | 1.19 | 0.97 | 0.23 | 0.09 |

Example I-31

Confirmation of Imaging of Amyloid in Brain (1) Aβ$_{1-42}$ (Wako) was dissolved in phosphate buffer (pH 7.4) and shaken at 37° C. for 72 hours, to obtain a 1 mg/mL suspension of aggregated Aβ (hereinafter referred to as amyloid suspension in this Example).

(2) 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) Compound I-9 was dissolved in a 10 mg/mL ascorbic acid-containing physiological saline solution to obtain a sample solution (21 MBq/mL in radioactivity concentration in a sample solution, Example I-31). This solution was injected under thiopental anesthesia into the rat through the tail vein (dosage: 0.5 mL, dosed radioactivity: 11-15 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 1-14).

FIG. 1-14 shows images by autoradiogram and Thioflavin T staining of the brain slice of the rat to which amyloid was injected intracerebrally. As shown in this figure, a marked accumulation of radioactivity in the specimen to which Compound I-9 was injected was also observed in the amygdaloid nucleus on the side to which the amyloid suspension was injected. On the other hand, no significant accumulation of radioactivity was observed in the amygdaloid nucleus on the side to which the physiological saline solution was injected, compared with the other sites. On the autoradiogram, little accumulation of radioactivity was observed at sites other than the sites to which amyloid was injected. From the result of Thioflavin T staining, it was confirmed that amyloid was present in the site where radioactivity is accumulated (FIG. 1-14). These results imply that Compound I-9 possesses a property of accumulating on intracerebral amyloid and a capability of imaging intracerebral amyloid.

Example I-32

Chromosome Aberration Test

In order to examine whether Compound I-4 can induce chromosome aberration, the chromosome aberration test was conducted using Chinese Hamster fibroblast cell line (CHL/IU cell) in a culture system with or without addition of S9 by short-term treatment process and in a 24-hour culture system by continuous treatment process. The addition amount of a sample to be tested was set to 1.2, 0.6, 0.3, and 0.15 mg/mL for all the respective culture systems.

When appearance frequency of cells with chromosome aberration apparently increased as compared to negative control group and dose dependency was observed, or when the appearance frequency apparently increased at a single dose and reproducibility was observed, positive determination was given, and otherwise negative determination was given.

As the results of the test, the appearance frequency of cells having structural aberration or numerical aberration (diploid) in all the culture systems treated with Compound I-4 was comparable to that of the negative control group. On the other hand, the positive control group for the respective culture systems showed a marked increase of the appearance frequency of cells having structural aberration. From the above results, the capability of inducing chromosome aberration of Compound I-4 was judged to be negative under the test conditions.

Example I-33

Micronucleus Test

In order to study mutagenicity (in vivo) of Compound I-4, induction of micronucleated polychromatic erythrocyte (hereinafter referred to as MNPCE) was examined using bone marrow cells of Crlj:CD1(ICR) male mouse.

0 mg/kg (negative control group), 250, 500, 1000 and 2000 mg/kg (test sample group) were set as doses for the test. Mice were sacrificed 24 and 48 hours after single oral administration, and bone marrow smear was prepared and observed. Further, a single dose of MMC at 2 mg/kg was abdominally administrated in positive control group, mice were sacrificed 24 hours after the administration, and then bone marrow smear was prepared and observed.

When appearance frequency of MNPCE in each administration group showed a dose-dependent increase or a statistically significant increase as compared to negative control group, positive determination was given, and otherwise negative determination was given. As statistical analysis, significance tests were conducted by Wilcoxon rank sum test for the appearance frequency of MNPCE and the ratio of polychromatic erythrocyte (hereinafter referred to as PCE) to the total red blood cell (hereinafter referred to as RBC) in each administration group concerning the test sample and positive control groups relative to the negative control group and concerning these groups relative to each other where the significance level was set to less than 5% and less than 1%, respectively.

From the results of the test, no statistically significant difference was observed on the appearance frequency of MNPCE and the ratio of PCE to RBC for the test sample group as compared to the negative control group. On the other hand, a significant increase was observed on the appearance frequency of MNPCE for the positive control group as compared to the negative control group. Based on these results, mutagencity (in vivo) of the test sample was judged to be negative because no induction of micronucleus in mouse bone marrow cells was observed under the above test conditions using Compound I-4.

Example II

In the following Examples, the names of the individual compounds used in the experiment are defined as shown in Table 2-1.

TABLE 2-1

| Compound name | Common name |
|---|---|
| Compound II-1 | 2-[4'-(2''-hydroxyethoxy)phenyl]-6-[$^{123}$I]iodoimidazo[1,2-a]pyridine |
| Compound II-2 | 2-(4'-ethoxyphenyl)-6-[$^{123}$I]iodoimidazo[1,2-a]pyridine |
| Compound II-3 | 2-[4'-(2''-hydroxyethoxy)phenyl]-6-iodoimidazo[1,2-a]pyridine |
| Compound II-4 | 2-[3'-(2''-hydroxyethoxy)phenyl]-6-[$^{123}$I]iodoimidazo[1,2-a]pyridine |
| Compound II-5 | 2-[3'-(2''-hydroxyethoxy)phenyl]-6-iodoimidazo[1,2-a]pyridine |
| Compound II-6 | 2-[4'-(3''-hydroxypropoxy)phenyl]-6-[$^{123}$I]iodoimidazo[1,2-a]pyridine |
| Compound II-7 | 2-[4'-(3''-hydroxypropoxy)phenyl]-6-iodoimidazo[1,2-a]pyridine |

Example II-1

Synthesis of 2-[4'-(2''-hydroxyethoxy)phenyl]-6-iodoimidazo[1,2-a]pyridine (Non-radioactive Iodinated Form)

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 2-1, Step 1).

441 mg (corresponding to 2.0 mmol) of 2-bromo-4'-hydroxyacetophenone and 449 mg (corresponding to 2.0 mmol) of 2-amino-5-iodopyridine were dissolved in 15 mL of acetonitrile. The resulting solution was refluxed in an oil bath at 110° C. for 5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 526 mg (corresponding to 1.56 mmol) of 2-(4'-hydroxyphenyl)-6-iodoimidazo[1,2-a]pyridine (FIG. 2-1, Step 2).

Separately, 2.50 g (corresponding to 20.0 mmol) of 2-bromoethanol and 2.72 g (corresponding to 40.0 mmol) of imidazole were dissolved in 10 mL of dimethylformamide (DMF), and cooled to 0° C. Then, 5.50 g (corresponding to 20.0 mmol) of t-butyldiphenylchlorosilane (TBDPSC1) was added thereto. After the reaction mixture was stirred at room temperature for 18 hours, a saturated sodium chloride solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=10/1) to obtain 7.04 g (corresponding to 19.4 mmol) of 1-bromo-2-(t-butyldiphenylsiloxy)ethane (FIG. 2-1, Step 3).

200 mg (corresponding to 0.595 mmol) of 2-(4'-hydroxyphenyl)-6-iodoimidazo[1,2-a]pyridine was dissolved in 3.0 mL of dimethylformamide, and 247 mg (corresponding to 1.79 mmol) of potassium carbonate was added thereto. Then, 259 mg (corresponding to 0.714 mmol) of 1-bromo-2-(t-butyldiphenylsiloxy)ethane was added thereto. After the reaction mixture was stirred at 90° C. for 2 hours, a saturated sodium chloride solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=2/1) to obtain 368 mg (corresponding to 0.595 mmol) of 2-[4'-(2"-t-butyldiphenylsiloxyethoxy)phenyl]-6-iodoimidazo[1,2-a]pyridine (FIG. 2-1, Step 4).

368 mg (corresponding to 0.595 mmol) of 2-[4'-(2"-t-butyldiphenylsiloxyethoxy)phenyl]-6-iodoimidazo[1,2-a]pyridine was dissolved in 1.0 mL of tetrahydrofuran (THF), and 0.70 mL of a 1.0 mol/L tetrahydrofuran solution of tetrabutylammoniumfluoride (TBAF) was added thereto. After the reaction mixture was stirred at room temperature for 2 hours, ammonium chloride solution was added, followed by addition of 5.0 mL of water and 2.0 mL of acetonitrile. Then, precipitates were filtered. The filtered precipitates were washed with water and acetonitrile in this order, to obtain 226 mg (corresponding to 0.595 mmol) of 2-[4'-(2"-hydroxyethoxy)phenyl]-6-iodoimidazo[1,2-a]pyridine (FIG. 2-1, Step 5).

The NMR measurement results of the resulting 2-[4'-(2"-hydroxyethoxy)phenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: dimethylsulfoxide-d6; resonance frequency: 500 MHz): δ 8.95 (s, 1H), 8.27 (s, 1H), 7.87 (d, J=8.7 Hz, 2H), 7.54-7.46 (m, 2H), 7.04 (d, J=8.7 Hz, 2H), 4.04 (t, J=4.6 Hz, 2H), 3.73 (t, J=4.6 Hz, 2H).

$^{13}$C-NMR (solvent: dimethylsulfoxide-d6, resonance frequency: 500 MHz): δ 158.9, 143.0, 142.4, 133.5, 131.5, 127.1, 124.4, 116.7, 114.8, 108.1, 76.7, 69.5, 59.4.

Example II-2

Synthesis of 6-tributylstannyl-2-[4'-(2"-hydroxyethoxy)phenyl]imidazo[1,2-a]pyridine 100 mg (corresponding to 0.263 mmol) of 2-[4'-(2"-hydroxyethoxy)phenyl]-6-iodoimidazo[1,2-a]pyridine obtained in Example II-1 was dissolved in 4.0 mL of dioxane, and 2.0 mL of triethylamine was added thereto. Then, 0.20 mL (corresponding to 0.39 mmol) of bis(tributyltin) and 20.1 mg (a catalytic amount) of tetrakis-triphenylphosphine palladium were added thereto. After the reaction mixture was stirred at 90° C. for 21 hours, the solvent was distilled off under reduced pressure. The residue was purified by flash silica gel column chromatography (elution solvent: hexane/ethyl acetate=1/2), to obtain 75.3 mg (corresponding to 0.139 mmol) of 6-tributylstannyl-2-[4'-(2"-hydroxyethoxy)phenyl]imidazo[1,2-a]pyridine (FIG. 2-2, Step 1).

The NMR measurement results of the resulting 6-tributylstannyl-2-[4'-(2"-hydroxyethoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl; resonance frequency: 500 MHz): δ 7.98 (s, 1H), 7.89 (d, J=8.7 Hz, 1H), 7.75 (s, 1H), 7.56 (d, J=8.7 Hz, 1H), 7.15 (d, J=8.7 Hz, 1H), 6.98 (d, J=8.7 Hz, 1H), 4.13 (t, J=4.6 Hz, 2H), 3.99 (t, J=4.6 Hz, 2H), 2.63 (s, 3H), 1.64-1.51 (m, 6H), 1.36 (sextet, J=7.3 Hz, 6H), 1.19-1.06 (m, 6H), 0.92 (t, J=7.3 Hz, 9H).

$^{13}$C-NMR (solvent: chloroform-dl, resonance frequency: 500 MHz): δ 158.6, 145.7, 145.0, 131.2, 130.0, 127.4, 127.2, 121.9, 116.9, 114.8, 106.4, 69.3, 61.4, 29.0, 27.3, 13.7, 9.8.

Example II-3

Synthesis of 2-[4'-(2"-hydroxyethoxy)phenyl]-6-[$^{123}$I]iodoimidazo[1,2-a]pyridine To 60 μL of a mixed solution of 6-tributylstannyl-2-[4'-(2"-hydroxyethoxy)phenyl]imidazo[1,2-a]pyridine (concentration: 1 mg/mL) in methanol/dimethylsulfoxide (mixing ratio: 9/1), 150 μL of 1 mol/L hydrochloric acid, 15 μL of 1 mmol/L sodium iodide, 250 μL of [$^{123}$I]sodium iodide of 274 MBq and 15 μL of 10% (w/v) hydrogen peroxide were added. After the mixed solution was left to stand at 50° C. for 10 minutes, it was subjected to HPLC under the following conditions, to obtain 2-[4'-(2"-hydroxyethoxy)phenyl]-6-[$^{123}$I]iodoimidazo[1,2-a]pyridine fraction.

HPLC conditions:
Column: Phenomenex Luna C18 (trade name; manufactured by Phenomenex Co.; size: 4.6×150 mm)
Mobile phase: 0.1% trifluoroacetic acid/acetonitrile=20/80 to 0/100 (17 minutes)
Flow rate: 1.0 mL/min.
Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[4'-(2"-hydroxyethoxy)phenyl]-6-[$^{123}$I]iodoimidazo[1,2-a]pyridine. The column was rinsed with 1 mL of water, and then 1 mL of diethyl ether was passed therethrough to elute 2-[4'-(2"-hydroxyethoxy)phenyl]-6-[$^{123}$I]iodoimidazo[1,2-a]pyridine. The amount of radioactivity of the obtained compound was 22 MBq at the end of synthesis. Further, the TLC analysis was conducted under the following conditions, and as a result, the radiochemical purity of the compound was 97%.

TLC analysis conditions:

TLC plate: Silica Gel 60 $F_{254}$ (trade name; manufactured by Merck & Co., Inc.)

Mobile phase: Chloroform/methanol/triethylamine=100/1/2

Detector: Rita Star (trade name; manufactured by raytest)

Example II-4

Synthesis of 2-(4'-ethoxyphenyl)-6-iodoimidazo[1,2-a]pyridine (Non-radioactive Iodinated Form)

30 mL of ethyl acetate was added to 2.72 g (corresponding to 12.2 mmol) of cupric bromide to obtain a suspension, to which 1.00 g (corresponding to 6.09 mmol) of 4'-ethoxyacetophenone was added. Then, the mixture was refluxed. After 3 hours, the reaction mixture was cooled down to room temperature and filtered. Then, the resulting filtrate was concentrated under reduced pressure. The residue was dissolved in ethyl acetate and concentrated. The resulting crude product was purified by silica gel column chromatography (elution solvent: hexane/ethyl acetate=10/1), to obtain 1.20 g (corresponding to 4.94 mmol) of 2-bromo-4'-ethoxyacetophenone (FIG. 2-3, Step 1).

1.20 g (corresponding to 4.94 mmol) of 2-bromo-4'-ethoxyacetophenone and 1.09 g (corresponding to 4.95 mmol) of 2-amino-5-iodopyridine were dissolved in 20 mL of acetonitrile. The resulting solution was refluxed in an oil bath at 110° C. for 1.5 hours. After the completion of the reaction, the reaction solution was cooled down to room temperature, and precipitates were filtered. Then, the precipitates were washed with acetonitrile and dried under reduced pressure. The resulting crude crystals were suspended in a mixed solution of 10 mL of water and 5 mL of methanol. Then, about 20 mL of a saturated sodium hydrogencarbonate solution was added thereto, and the mixture was sonicated for 10 minutes using an ultrasonic washing machine. Precipitates were filtered and recovered from the resulting mixture, sufficiently washed with water, and dried under reduced pressure, to obtain 1.64 g (corresponding to 4.50 mmol) of 2-(4'-ethoxyphenyl)-6-iodoimidazo[1,2-a]pyridine (FIG. 2-3, Step 2).

The NMR measurement results of the resulting 2-(4'-ethoxyphenyl)-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: dimethylsulfoxide-d6; resonance frequency: 500 MHz): δ 9.06 (s, 1H), 8.38 (s, 1H), 7.86 (d, J=8.7 Hz, 2H), 7.77-7.57 (m, 2H), 7.06 (d, J=8.7 Hz, 2H), 4.10 (q, J=6.9 Hz, 2H), 1.36 (t, J=6.9 Hz, 3H).

$^{13}$C-NMR (solvent: dimethylsulfoxide-d6, resonance frequency: 500 MHz): δ 159.3, 141.1, 140.3, 135.9, 132.0, 127.3, 122.1, 115.3, 114.9, 108.5, 78.6, 63.2, 14.5.

Example II-5

Synthesis of 6-tributylstannyl-2-(4'-ethoxyphenyl)imidazo[1,2-a]pyridine 364 mg (corresponding to 1.00 mmol) of 2-(4'-ethoxyphenyl)-6-iodoimidazo[1,2-a]pyridine obtained in Example II-4 was dissolved in 4.0 mL of dioxane, and 2 mL of triethylamine was added thereto. Then, 0.76 mL (corresponding to 1.5 mmol) of bis(tributyltin) and 76.3 mg (a catalytic amount) of tetrakis-triphenylphosphine palladium were added thereto. After the reaction mixture was stirred at 90° C. for 23 hours, the solvent was distilled off under reduced pressure. The residue was purified by flash silica gel column chromatography (elution solvent: hexane/ethyl acetate=5/1), to obtain 331 mg (corresponding to 0.628 mmol) of 6-tributylstannyl-2-(4'-ethoxyphenyl)imidazo[1,2-a]pyridine (FIG. 2-4, Step 1).

The NMR measurement results of the resulting 6-tributylstannyl-2-(4'-ethoxyphenyl)imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl; resonance frequency: 500 MHz): δ 7.96 (s, 1H), 7.88 (d, J=8.7 Hz, 2H), 7.74 (s, 1H), 7.58 (d, J=8.7 Hz, 1H), 7.14 (d, J=8.7 Hz, 1H), 6.96 (d, J=8.7 Hz, 2H), 4.07 (q, J=6.9 Hz, 2H), 1.63-1.49 (m, 6H), 1.43 (t, J=6.9 Hz, 3H), 1.39-1.31 (m, 6H), 1.18-1.04 (m, 6H), 0.90 (t, J=7.3 Hz, 9H).

$^{13}$C-NMR (solvent: chloroform-dl, resonance frequency: 500 MHz): δ 159.0, 145.7, 145.2, 131.2, 130.1, 127.4, 126.7, 121.9, 117.0, 114.8, 106.4, 63.6, 29.1, 27.4, 15.0, 13.8, 9.9.

Example II-6

Synthesis of 2-(4'-ethoxyphenyl)-6-[$^{123}$I]iodoimidazo[1,2-a]pyridine

To 60 μL of a mixed solution of 6-tributylstannyl-2-(4'-ethoxyphenyl)imidazo[1,2-a]pyridine (concentration: 1 mg/mL) in methanol/dimethylsulfoxide (mixing ratio: 9/1), 90 μL of 2 mol/L hydrochloric acid, 15 μL of 1 mmol/L sodium iodide, 100 μL of [$^{123}$I]sodium iodide of 436 MBq and 15 μL of 10% (w/v) hydrogen peroxide were added. After the mixed solution was left to stand at 50° C. for 10 minutes, it was subjected to HPLC under the following conditions to obtain 2-(4'-ethoxyphenyl)-6-[$^{123}$I]iodoimidazo[1,2-a]pyridine fraction HPLC conditions:

Column: Phenomenex Luna C18 (trade name; manufactured by Phenomenex Co.; size: 4.6×150 mm)

Mobile phase: 0.1% trifluoroacetic acid/acetonitrile=20/80 to 0/100 (17 minutes)

Flow rate: 1.0 mL/min.

Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-(4'-ethoxyphenyl)-6-[$^{123}$I]iodoimidazo[1,2-a]pyridine. The column was rinsed with 1 mL of water, and then 1 mL of diethyl ether was passed therethrough to elute 2-(4'-ethoxyphenyl)-6-[$^{123}$I]iodoimidazo[1,2-a]pyridine. The amount of radioactivity of the obtained compound was 88 MBq at the end of synthesis. Further, the TLC analysis was conducted under the following conditions, and as a result, the radiochemical purity of the compound was 98%.

TLC analysis conditions:
TLC plate: Silica Gel 60 $F_{254}$ (trade name; manufactured by Merck & Co., Inc.)
Mobile phase: Chloroform/methanol/triethylamine=100/1/2
Detector: Rita Star (trade name; manufactured by raytest)

Reference Example II-1

Synthesis of [$^{123}$I]-IMPY

[$^{123}$I]-IMPY was synthesized in accordance with the following steps for use in Comparative Examples for evaluations on measurement of log $P_{octanol}$ and accumulations in brain.

In accordance with the method described in a literature (Zhi-Ping Zhuang et al., J. Med. Chem., 2003, 46, p. 237-243), 6-tributylstannyl-2-[4'-(N,N-dimethylamino)phenyl]imidazo[1,2-a]pyridine was synthesized, and dissolved in methanol (concentration: 1 mg/mL). To 53 µL of the resulting solution, 75 µL of 1 mol/L hydrochloric acid, 60-70 µL of [$^{123}$I]sodium iodide of 224-253 MBq, 10 µL of a 1 mmol/L sodium iodide solution and 15 µL of 10% (w/v) hydrogen peroxide were added. After the mixed solution was left to stand at 50° C. for 10 minutes, the solution was subjected to HPLC under the same conditions as in Example II-3, to obtain [$^{123}$I]-IMPY fraction.

10 ml of water was added to the fraction. The resulting solution was passed through a reversed phase column (trade name: Sep-Pak (registered trademark) Light C8 Cartridges manufactured by Waters; the packed amount of the packing agent: 145 mg), so that the column adsorbs and collects the [$^{123}$I]-IMPY. The column was rinsed with 1 mL of water, and then 1 mL of diethyl ether was passed therethrough, to elute [$^{123}$I]-IMPY. The obtained radioactivity was 41-57 MBq at the end of synthesis. Further, the TLC analysis was conducted under the same conditions as described in Example II-3, and as a result, the radiochemical purity of the compound was 93%.

Example II-7, Comparative Example II-1 to II-3

Measurement of Affinity with Amyloid

Affinity of the present compounds with amyloid was examined by the following in vitro binding tests.

(1) Aβ$_{1-42}$ (Wako) was dissolved in phosphate buffer (pH 7.4) and shaken at 37° C. for 72 hours, to obtain 1 mg/mL of a suspension (hereinafter referred to as amyloid suspension in this Example) of aggregated Aβ (hereinafter referred to as amyloid in this Example).

(2) According to the method described in a literature (Naiki, H., et al., Laboratory Investigation 74, p. 374-383 (1996)), the amyloid suspension was subjected to qualitative experiment based on fluorescence spectrophotometric method using Thioflavin T (manufactured by Fluka) to confirm that the aggregated Aβ obtained in (1) was amyloid (measurement conditions: excitation wavelength of 446 nm, and emission wavelength of 490 nm).

(3) According to the method described in a literature (Wang, Y., et al., J. Labeled Compounds Radiopharmaceut. 44, S239 (2001)), [$^{125}$I]2-(3'-iodo-4'-aminophenyl)benzothiazole (hereinafter referred to as [$^{125}$I]3'-I-BTA-0) was prepared from a labeling precursor 2-(4'-aminophenyl)benzothiazole, and dissolved in ethanol. As Congo Red, Thioflavin T and 6-methyl-2-[4'-(N,N-dimethylamino)phenyl]benzothiazole (hereinafter referred to as 6-Me-BTA-2), commercially available reagents were weighed and used as they were.

(4) IMPY was synthesized according to the method described in a literature (Zhuang, Z. P., et al., J. Med. Chem. 46, 237 (2003))

(5) Each compound for evaluation or ethanol solution thereof, an ethanol solution of [$^{125}$I]3'-I-BTA-0 prepared above in (3) and amyloid suspension prepared above in (1) were dissolved in 1% bovine serum albumin-containing phosphate buffer (pH 7.4), and samples at final concentrations of each compound for evaluation, [$^{125}$I]3'-I-BTA-0 and amyloid shown in Table 2-2 respectively was prepared.

TABLE 2-2

| | Final concentrations of each compound in sample solutions | | | |
|---|---|---|---|---|
| Experiment | Compound for evaluation | Concentration of compound for evaluation | [$^{125}$I]3'-I-BTA-0 concentration | Amyloid |
| Comparative Example II-1 | Congo Red | Each concentration of 0, 0.001, 0.01, 0.1, 1, 10, 100, 1000 nmol/L | 400 pmol/L | 1 µmol/L |
| Comparative Example II-2 | Thioflavin T | | | |
| Comparative Example II-3 | IMPY | | | |
| Example II-7 | Compound II-3 | | | |

(6) Each sample solution prepared above in (5) was filled in each well (about 0.3 mL in volume) of a 96-well microplate. The microplate filled with the sample solutions was shaken at a given rate (400 rpm) at 22° C. for 3 hours. Then, each sample solution was filtered through a glass fiber filter (trade name: Mulutiscreen™-FC, manufactured by Millipore), to separate the [$^{125}$I]3'-I-BTA-0 attached to amyloid from the free [$^{125}$I]3'-I-BTA-0.

(7) The glass fiber filter used for the filtration of each sample solution was washed with 1% bovine serum albumin-containing phosphate buffer (pH 7.4) (0.5 mL×5), and radioactivity of the glass fiber filter was measured with an autowell gamma system (manufactured by Aloka, Type: ARC-301B) (hereinafter, A denotes the radioactivity level in a sample with zero (0) concentration of each compound for evaluation, and B denotes the radioactivity level in a sample with 0.001 nmol/L or higher concentration of each compound for evaluation).

(8) Separately, a solution containing 15 µmol/L of 6-Me-BTA-2, 400 pmol/L of [$^{125}$I]3'-I-BTA-0 and 1 µmol/L of amyloid were prepared and subjected to the same procedures as described above in (7) and (8) to measure a radioactivity level. The measured radioactivity level was defined as the background radioactivity level, and used in the calculation of the inhibition ratio (hereinafter referred to as BG).

(9) Using the radioactivity levels measured above in (7) and (8), the inhibition ratio was determined by the following formula (2-1).

$$\frac{B - BG}{A - BG} \times 100 \ (\%) \qquad (2\text{-}1)$$

A graph in which values converted by probit transformation from the obtained inhibition ratios were plotted relative to logarithms of concentrations of compounds for evaluation was prepared to obtain an approximate straight line by the least square method. Using the line, a 50%, inhibition concentration of each compound for evaluation (hereinafter referred to as $IC_{50\%}$ value) was determined. Using the value as an indicator, affinity of each compound for evaluation with amyloid was evaluated.

$IC_{50\%}$ value of each compound for evaluation is shown in Table 2-3. Compounds II-3 showed $IC_{50\%}$ values of less than 100 and had higher affinity with amyloid than Congo Red and Thioflavin T which are generally known to have affinity with amyloid. The results show that Compounds II-3 has good affinity with amyloid like IMPY.

TABLE 2-3

$IC_{50\%}$ values of the present compounds

| Experiment | Compound for evaluation | $IC_{50\%}$ values (nmol/L) |
|---|---|---|
| Comparative Example II-1 | Congo Red | >1000 |
| Comparative Example II-2 | Thioflavin T | >1000 |
| Comparative Example II-3 | IMPY | 25.8 |
| Example II-7 | Compound II-3 | 66.9 |

Example II-8 to II-9, Comparative Example II-4

Measurement of Partition Coefficient Based on the Octanol Extraction Method

Partition coefficients based on the octanol extraction method (hereinafter referred to as log $P_{octanol}$) were measured, which are generally known as an indicator of permeability of compounds through the blood-brain barrier (hereinafter referred to as BBB).

A diethyl ether solution of Compound II-1 prepared in Example II-3 (Example II-8), a diethyl ether solution of Compound II-2 prepared in Example II-6 (Example II-9), and a diethyl ether solution of [$^{123}$I]-IMPY prepared in Reference Example II-1 (Comparative Example II-2) were each diluted with 10 mg/mL ascorbic acid-containing physiological saline solution, and adjusted to radioactive concentration of 20-30 MBq/mL. To 2 mL of octanol, 10 µL each of the prepared sample solutions was added, 2 mL of 10 mmol/L phosphate buffer (pH 7.4) was added, followed by stirring for 30 seconds. After the mixture was centrifuged with a low-speed centrifuge (2000 rpm×60 min.), the octanol layer and the water layer were sampled each in an amount of 1 mL, and subjected to measurement of radioactivity count with an autowell gamma system (Type: ARC-301B, manufactured by Aloka). Using the obtained radioactivity count, log $P_{octanol}$ was calculated in accordance with the equation (2-2).

$$\log P_{octanol} = \log_{10}\left(\frac{\text{Radioactivity count of octanol layer}}{\text{Radioactivity count of water layer}}\right) \quad (2\text{-}2)$$

The results are shown in Table 2-4. All compounds showed log $P_{octanol}$ value between 1 and 3. It is known that compounds permeable to BBB show a log $P_{octanol}$ value between 1 and 3 (Douglas D. Dischino et al., J. Nucl. Med., (1983), 24, p. 1030-1038). Thus, it is implied that both compounds have a BBB permeability like IMPY.

TABLE 2-4 log $P_{octanol}$ value of the present compound

| Experiment | Compound | log $P_{octanol}$ value |
|---|---|---|
| Comparative Example II-4 | [$^{123}$I]-IMPY | 1.9 |
| Example II-8 | Compound II-1 | 1.8 |
| Example II-9 | Compound II-2 | 2.1 |

Example II-10 to II-11, Comparative Example II-5

Measurement of Transferability into Brain and Clearance

Using Compound II-1 (Example II-10) and Compound II-2 (Example II-11), a time course change of radioactive accumulation in brain of male Wistar rats (7-week old) was measured.

A diethyl ether solution of Compound II-1 (Example II-10) prepared in Example II-3, a diethyl ether solution of Compound II-2 (Example II-11) prepared in Example II-6 and a diethyl ether solution of [$^{123}$I]-IMPY (Comparative Example II-5) prepared in Reference Example II-1 were each diluted with 10 mg/mL ascorbic acid-containing physiological saline solution to adjust radioactive concentration to 8-12 MBq/mL. 0.05 mL each of the prepared sample solutions was injected under thiopental anesthesia into the tail vein of the rats. The rats were sacrificed by bleeding from abdominal artery, and brains were removed and subjected to measurement of mass of brains and further subjected to measurement of radioactivity (hereinafter referred to as A in this Example) with a single channel analyzer (detector type SP-20 manufactured by OHYO KOKEN KOGYO Co., Ltd.) 2, 5, 30, and 60 minutes after the injection. Further, the radioactivity level of the rest of the whole body was measured in the same manner as above (hereinafter referred to as B in this Example). Using these measurement results, radioactive distribution per unit weight of brain (% ID/g) at the respective time points were calculated in accordance with the following formula (2-3).

Three animals were used for the experiment at the respective time points.

$$\% \ ID/g = \frac{A}{B \times \text{brain weight}} \times 100 \quad (2\text{-}3)$$

The results are shown in Table 2-5. As shown in Table 2-5, Compounds II-1 and II-2 showed a significant radioactive accumulation like [$^{123}$I]-IMPY at the time point of two minutes after the injection, and then showed a tendency to rapidly clear away in 60 minutes. These results suggest that both Compounds II-1 and II-2 possess excellent transferability to brain and rapid clearance from brain like [$^{123}$I]-IMPY.

TABLE 2-5

Radioactive distribution in brain of the
present compound after intravenous injection (rats)

| Compound | | Radioactive distribution per unit weight (% ID/g) | | | |
|---|---|---|---|---|---|
| | | After 2 min. | After 5 min. | After 30 min. | After 60 min. |
| Example II-10 | Compound II-1 | 0.90 | 0.52 | 0.06 | 0.01 |
| Example II-11 | Compound II-2 | 0.89 | 0.66 | 0.13 | 0.04 |
| Comparative Example II-5 | $^{123}$I-IMPY | 1.19 | 0.97 | 0.23 | 0.09 |

Comparative Example II-6

Ex Vivo Autoradiogram of $^{123}$I-IMPY Using Rats of Amyloid Injected Model (1) Aβ$_{1-40}$ (manufactured by Peptide Institute, INC.) was dissolved in phosphate buffer (pH 7.4) and shaken at 37° C. for 72 hours, to obtain 1 mg/mL of a suspension of aggregated Aβ (hereinafter referred to as amyloid suspension in this Example).

(2) 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) [$^{123}$I]-IMPY was dissolved in a 10 mg/mL ascorbic acid-containing physiological saline solution to obtain a sample solution (29 MBq/mL in radioactivity concentration in the sample solution). This solution was injected under thiopental anesthesia into the rat through the tail vein (dosage: 0.5 mL, dosed radioactivity: 14.5 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 2-5b).

FIG. 2-5 shows images by autoradiogram and Thioflavin T staining of the brain slice of the rat to which amyloid was injected intracerebrally. As shown in this figure, a marked accumulation of radioactivity was observed in the amygdaloid nucleus on the side to which the amyloid suspension was injected, but also non-specific accumulation was observed in white matter where amyloid was not injected.

Example II-12

Confirmation of Imaging of Amyloid in Brain

The following experiment was carried out in order to examine whether amyloid in brain can be imaged by the compound of the present invention.

(1) Aβ$_{1-42}$ (Wako) was dissolved in phosphate buffer (pH 7.4) and shaken at 37° C. for 72 hours, to obtain 1 mg/mL of a suspension of aggregated Aβ (hereinafter referred to as amyloid suspension in the Examples).

(2) 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) Compound II-1 was dissolved in a 10 mg/mL ascorbic acid-containing physiological saline solution to obtain a sample solution (22 MBq/mL in radioactivity concentration in the sample solution). This solution was injected under thiopental anesthesia into the rat through the tail vein (dosage: 0.5 mL, dosed radioactivity: 11-13 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 2-6b).

FIG. 2-6 shows images by autoradiogram and Thioflavin T staining of the brain slice of the rat to which amyloid was injected intracerebrally. As shown in this figure, a marked accumulation of radioactivity was observed in the amygdaloid nucleus on the side to which the amyloid suspension was injected. On the other hand, no significant accumulation of radioactivity was observed in the amygdaloid nucleus on the side to which the physiological saline solution was injected, compared with the other sites. On the autoradiogram, little accumulation of radioactivity was observed at sites other than the sites to which amyloid was injected. From the result of Thioflavin T staining, it was confirmed that amyloid was present in the site where radioactivity is accumulated (FIG. 2-6b).

Thus, Compound II-1 showed little radioactive accumulation at the sites other than amyloid injected sites, and showed little non-specific binding to the white matter observed in [$^{123}$I]-IMPY. These results suggest that Compound II-1 possesses an excellent capability of imaging amyloid in the total autoradiogram image. These results also suggest that Compound II-1 is a compound that possesses a high specificity to imaging of intracerebral amyloid.

Example II-13

Confirmation of Imaging of Amyloid in Brain

The same procedures as in Example II-12 were performed except using a 10 mg/mL solution of Compound II-2 in ascorbic acid (the radioactive concentration of the sample solution was 25 MBq/mL).

FIG. 2-7 shows images by autoradiogram and Thioflavin T staining of the brain slice of the rat to which amyloid was injected intracerebrally. As shown in this figure, a marked accumulation of radioactivity was observed in the amygdaloid nucleus on the side to which the amyloid suspension was injected. From the result of Thioflavin T staining in the site where radioactivity was accumulated, it was confirmed that amyloid was present in the accumulation site. On the other hand, no significant accumulation of radioactivity was observed in the amygdaloid nucleus on the side to which the physiological saline solution was injected, compared with the other sites.

Compound II-2 showed some radioactive accumulation in sites other than amyloid injected sites, but the accumulation was highly suppressed as compared to $^{123}$I-IMPY. As a result, the whole image was provided with a high capability of imaging amyloid.

These results suggest that Compound II-2 is a compound that possesses a high specificity to imaging of intracerebral amyloid.

Example II-14

Synthesis of 2-[3'-(2"-hydroxyethoxy)phenyl]-6-iodoimidazo[1,2-a]pyridine (Non-radioactive Iodinated Form)

50 mL of ethyl acetate was added to 8.60 g (corresponding to 46.0 mmol) of cupric bromide to obtain a suspension, to which a solution of 2.50 g (corresponding to 22.0 mmol) of 3'-hydroxyacetophenone in 50 ml of ethyl acetate was added. Then, the resulting mixture was refluxed. After 2 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: hexane/ethyl acetate=2/1) to obtain 4.42 g (corresponding to 20.6 mmol) of 2-bromo-3'-hydroxyacetophenone (FIG. 2-8, Step 1).

987 mg (corresponding to 4.55 mmol) of 2-bromo-3'-hydroxyacetophenone and 1.00 g (corresponding to 4.55 mmol) of 2-amino-5-iodopyridine were dissolved in 50 mL of acetonitrile. The resulting solution was refluxed in an oil bath at 110° C. for 2 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 1 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 927 mg (corresponding to 2.76 mmol) of 2-(3'-hydroxyphenyl)-6-iodoimidazo[1,2-a]pyridine (FIG. 2-8, Step 2).

Separately, 2.50 g (corresponding to 20.0 mmol) of 2-bromoethanol and 2.72 g (corresponding to 40.0 mmol) of imidazole were dissolved in 10 mL of dimethylformamide, and cooled to 0° C. Then, 5.50 g (corresponding to 20.0 mmol) of t-butyldiphenylchlorosilane was added thereto. After the reaction mixture was stirred at room temperature for 18 hours, a saturated sodium chloride solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=10/1) to obtain 7.04 g (corresponding to 19.4 mmol) of 1-bromo-2-(t-butyldiphenylsiloxy)ethane (FIG. 2-8, Step 3).

300 mg (corresponding to 0.893 mmol) of 2-(3'-hydroxyphenyl)-6-iodoimidazo[1,2-a]pyridine was dissolved in 5.0 mL of dimethylformamide, and 370 mg (corresponding to 2.68 mmol) of potassium carbonate was added thereto. Then, 357 mg (corresponding to 0.982 mmol) of 1-bromo-2-(t-butyldiphenylsiloxy)ethane was added thereto. After the reaction mixture was stirred at 90° C. for 2 hours, a saturated sodium chloride solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=3/1) to obtain 477 mg (corresponding to 0.771 mmol) of 2-[3'-(2"-t-butyldiphenylsiloxyethoxy)phenyl]-6-iodoimidazo[1,2-a]pyridine (FIG. 2-8, Step 4).

477 mg (corresponding to 0.771 mmol) of 2-[3'-(2"-t-butyldiphenylsiloxyethoxy)phenyl]-6-iodoimidazo[1,2-a]pyridine was dissolved in 0.98 mL of tetrahydrofuran, and 0.93 mL of a 1.0 mol/L tetrahydrofuran solution of tetrabutylammoniumfluoride was added thereto. After the reaction mixture was stirred at room temperature for 15 minutes, ammonium chloride solution was added followed by addition of 5.0 mL of water and 2.0 mL of acetonitrile to filter precipitates. The filtered precipitates were washed with water and acetonitrile in this order to obtain 120 mg (corresponding to 0.316 mmol) of 2-[3'-(2"-hydroxyethoxy)phenyl]-6-iodoimidazo[1,2-a]pyridine (FIG. 2-8, Step 5).

The NMR measurement results of the resulting 2-[3'-(2"-hydroxyethoxy)phenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: dimethylsulfoxide-d6; resonance frequency: 500 MHz): δ 8.91 (s, 1H), 8.35 (s, 1H), 7.52-7.51 (m, 2H), 7.45 (s, 2H), 7.35 (t, J=8.2 Hz, 1H), 6.93-6.90 (m, 1H), 4.06 (t, J=4.6 Hz, 2H), 3.75 (t, J=4.6 Hz, 2H).

Example II-15

Synthesis of 6-tributylstannyl-2-[3'-(2"-hydroxyethoxy)phenyl]imidazo[1,2-a]pyridine 70 mg (corresponding to 0.184 mmol) of 2-[3'-(2"-hydroxyethoxy)phenyl]-6-iodoimidazo[1,2-a]pyridine obtained in Example II-14 was dissolved in 4.0 mL of dioxane, and 2.0 mL of triethylamine was added thereto. Then, 0.20 mL (corresponding to 0.39 mmol) of bis(tributyltin) and 14.0 mg (a catalytic amount) of tetrakis-triphenylphosphine palladium were added thereto. After the reaction mixture was stirred at 90° C. for 20 hours, the solvent was distilled off under reduced pressure. The residue was purified by flash silica gel column chromatography (elution solvent: hexane/ethyl acetate=2/1) to obtain 73.0 mg (corresponding to 0.134 mmol) of 6-tributylstannyl-2-[3'-(2"-hydroxyethoxy)phenyl]imidazo[1,2-a]pyridine (FIG. 2-9, Step 1).

The NMR measurement results of the resulting 6-tributylstannyl-2-[3'-(2"-hydroxyethoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl; resonance frequency: 500 MHz): δ 7.99 (d, J=0.9 Hz, 1H), 7.82 (s, 1H), 7.64-7.50 (m, 3H), 7.34-7.31 (m, 1H), 7.18-7.17 (m, 1H), 6.90-6.87 (m, 1H), 4.20 (t, J=4.3 Hz, 2H), 3.98 (t, J=4.3 Hz, 2H), 1.69-1.48 (m, 6H), 1.39-1.32 (m, 6H), 1.19-1.05 (m, 6H), 0.91 (t, J=7.4 Hz, 9H).

Example II-16

Synthesis of 2-[3'-(2"-hydroxyethoxy)phenyl]-6-[$^{123}$I]iodoimidazo[1,2-a]pyridine To 60 µL of a mixed solution of 6-tributylstannyl-2-[3'-(2"-hydroxyethoxy)phenyl]imidazo[1,2-a]pyridine (concentration: 1 mg/mL) in methanol/dimethylsulfoxide (in a ratio of 9/1), 150 µL of 1 mol/L hydrochloric acid, 15 µL of 1 mmol/L sodium iodide, 250 µL of [$^{123}$I]sodium iodide of 274 MBq and 15 µL of 10% (w/v) hydrogen peroxide were added. After the mixed solution was left to stand at 50° C. for 10 minutes, it was subjected to HPLC under the following conditions to obtain 2-[3'-(2"-hydroxyethoxy)phenyl]-6-[$^{123}$I]iodoimidazo[1,2-a]pyridine fraction.

HPLC conditions:
Column: Phenomenex Luna C18 (trade name; manufactured by Phenomenex Co.; size: 4.6×150 mm)
Mobile phase: 0.1% trifluoroacetic acid/acetonitrile=20/80 to 0/100 (17 minutes)
Flow rate: 1.0 mL/min.
Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[3'-(2"-hydroxyethoxy)phenyl]-6-[$^{123}$I]iodoimidazo[1,2-a]pyridine. The column was rinsed with 1 mL of water, and then 1 mL of diethyl ether was passed therethrough to elute 2-[3'-(2"-hydroxyethoxy)phenyl]-6-[$^{123}$I]iodoimidazo[1,2-a]pyridine. The amount of radioactivity of the obtained compound was 112.9 MBq at the end of synthesis. Further, the TLC analysis was conducted under the following conditions, and as a result, the radiochemical purity of the compound was 97%.

TLC analysis conditions:
TLC plate: Silica Gel 60 F$_{254}$ (trade name; manufactured by Merck & Co., Inc.)
Mobile phase: Chloroform/methanol/triethylamine=100/1/2
Detector: Rita Star (trade name; manufactured by raytest)

Example II-17

Synthesis of 2-[4'-(3"-hydroxypropoxy)phenyl]-6-iodoimidazo[1,2-a]pyridine (Non-radioactive Iodinated Form)

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 2-10, Step 1).

987 mg (corresponding to 4.55 mmol) of 2-bromo-4'-hydroxyacetophenone and 1.00 g (corresponding to 4.55 mmol) of 2-amino-5-iodopyridine were dissolved in 50 mL of acetonitrile. The resulting solution was refluxed in an oil bath at 110° C. for 2 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 1 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 927 mg (corresponding to 2.76 mmol) of 2-(4'-hydroxyphenyl)-6-iodoimidazo[1,2-a]pyridine (FIG. 2-10, Step 2).

Separately, 7.0 g (corresponding to 50.4 mmol) of 2-bromopropanol and 6.86 g (corresponding to 101 mmol) of imidazole were dissolved in 50 mL of dimethylformamide, and cooled to 0° C. Then, 7.59 g (corresponding to 50.4 mmol) of t-butyldimethylchlorosilane was added thereto. After the reaction mixture was stirred at room temperature for 24 hours, it was supplemented with a saturated sodium chloride solution, and extracted three times with diethyl ether. The combined diethyl ether layers were dried over anhydrous magnesium sulfate, and concentrated under reduced pressure. The resulting crude product was purified by vacuum distillation (100° C., 70 mmHg), to obtain 7.23 g (corresponding to 30.2 mmol) of 1-bromo-3-(t-butyldimethylsiloxy)propane (FIG. 2-10, Step 3).

2.00 g (corresponding to 5.95 mmol) of 2-(4'-hydroxyphenyl)-6-iodoimidazo[1,2-a]pyridine was dissolved in 30.0 mL of dimethylformamide, and 2.47 g (corresponding to 17.9 mmol) of potassium carbonate was added. Then, 1.51 g (corresponding to 5.95 mmol) of 1-bromo-3-(t-butyldimethylsiloxy)propane was added thereto. After the reaction mixture was stirred at room temperature for 8 days, it was supplemented with saturated sodium chloride solution, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=1/1) to obtain 1.52 g (corresponding to 2.99 mmol) of 2-[4'-(3"-t-butyldimethylsiloxypropoxy)phenyl]-6-iodoimidazo[1,2-a]pyridine (FIG. 2-10, Step 4).

1.52 g (corresponding to 2.99 mmol) of 2-[4'-(3"-t-butyldimethylsiloxypropoxy)phenyl]-6-iodoimidazo[1,2-a]pyridine was dissolved in 5.0 mL of tetrahydrofuran, and 2.99 mL of a 1.0 mol/L tetrahydrofuran solution of tetrabutylammoniumfluoride was added thereto. After the reaction mixture was stirred at room temperature for 30 minutes, ammonium chloride solution was added followed by the addition of 10 mL of water and 5.0 mL of acetonitrile to filter precipitates. The filtered precipitates were washed with water and acetonitrile in this order, to obtain 1.03 g (corresponding to 2.61 mmol) of 2-[4'-(3"-hydroxypropoxy)phenyl]-6-iodoimidazo[1,2-a]pyridine (FIG. 2-10, Step 5).

The NMR measurement results of the resulting 2-[4'-(3"-hydroxypropoxy)phenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

¹H-NMR (solvent: dimethylformamide-d6; resonance frequency: 500 MHz): δ 8.96 (s, 1H), 8.33 (s, 1H), 7.98 (d, J=8.7 Hz, 2H), 7.46 (s, 2H), 7.06 (d, J=8.7 Hz, 2H), 4.63 (t, J=5.0 Hz, 1H), 4.17 (t, J=6.0 Hz, 2H), 3.72 (dt, J=5.0, 6.0 Hz, 2H), 1.98 (tt, J=6.0, 6.0 Hz, 2H).

Example II-18

Synthesis of 6-tributylstannyl-2-[4'-(3"-hydroxypropoxy)phenyl]imidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was refluxed. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 2-11, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was refluxed in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a]pyridine (FIG. 2-11, Step 2).

1.45 g (corresponding to 5.0 mmol) of 6-bromo-2-(4'-hydroxyphenyl)imidazo[1,2-a]pyridine that was sufficiently dried to remove moisture was dissolved in 50 mL of N,N-dimethylformamide, and 2.07 g (corresponding to 15.0 mmol) of potassium carbonate was added thereto. The mixture was supplemented with 680 μL (corresponding to 7.5 mmol) of 3-bromo-1-propanol, and then the solution was stirred at room temperature for 17 hours. After the completion of the reaction, the reaction solution was poured into water and extracted three times with chloroform. The combined chloroform layer was washed with a saturated sodium chloride solution, dried over anhydrous sodium sulfate, filtered and concentrated. The resulting crude product was recrystallized from methanol to obtain 1.28 g (corresponding to 3.67 mmol) of 6-bromo-2-[4'-(3"-hydroxypropoxy)phenyl]imidazo[1,2-a]pyridine (FIG. 2-11, Step 3).

100 mg (corresponding to 0.288 mmol) of 6-bromo-2-[4'-(3"-hydroxypropoxy)phenyl]imidazo[1,2-a]pyridine was dissolved in 4.0 mL of dioxane, and 2.0 mL of triethylamine was added thereto. Then, 0.22 mL (corresponding to 0.43 mmol) of bis(tributyltin) and 22.0 mg (a catalytic amount) of tetrakis-triphenylphosphine palladium were added thereto.

After the reaction mixture was stirred at 90° C. for 24 hours, the solvent was distilled off under reduced pressure, and the residue was purified by flash silica gel column chromatography (elution solvent: hexane/ethyl acetate=3/1) to obtain 68.0 mg (corresponding to 0.122 mmol) of 6-tributylstannyl-2-[4'-(3"-hydroxypropoxy)phenyl]imidazo[1,2-a]pyridine (FIG. 2-11, Step 4).

The NMR measurement results of the resulting 6-tributylstannyl-2-[4'-(3"-hydroxypropoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

¹H-NMR (solvent: chloroform-di; resonance frequency: 500 MHz): δ 7.97 (s, 1H), 7.88 (d, J=8.3 Hz, 2H), 7.74 (s, 1H), 7.58 (d, J=8.3 Hz, 1H), 7.14 (d, J=8.7 Hz, 1H), 6.98 (d, J=8.7 Hz, 2H), 4.18 (t, J=6.0 Hz, 2H), 3.89 (t, J=6.0 Hz, 2H), 2.08 (tt, J=6.0, 6.0 Hz, 2H), 1.59-1.49 (m, 6H), 1.39-1.31 (m, 6H), 1.18-1.05 (m, 6H), 0.90 (t, J=7.3 Hz, 9H).

Example II-19

Synthesis of 2-[4'-(3"-hydroxypropoxy)phenyl]-6-[$^{123}$I]iodoimidazo[1,2-a]pyridine To 100 μL of a mixed solution of 6-tributylstannyl-2-[4'-(3"-hydroxypropoxy)phenyl]imidazo[1,2-a]pyridine (concentration: 1 mg/mL) in methanol/dimethylsulfoxide (in a ratio of 9/1), 80 μL of 2 mol/L hydrochloric acid, 15 μL of 1 mmol/L sodium iodide, 120 μL of [$^{123}$I]sodium iodide of 414 MBq and 20 μL of 10% (w/v) hydrogen peroxide were added. After the mixed solution was left to stand at 50° C. for 10 minutes, the solution was subjected to HPLC under the following conditions, to obtain 2-[3'-(4"-hydroxypropoxy)phenyl]-6-[$^{123}$I]iodoimidazo[1,2-a]pyridine fraction.

HPLC conditions:
Column: Phenomenex Luna C18 (trade name; manufactured by Phenomenex Co.; size: 4.6×150 mm)
Mobile phase: 0.1% trifluoroacetic acid/acetonitrile=20/80 to 0/100 (17 minutes)
Flow rate: 1.0 mL/min.
Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[4'-(3"-hydroxypropoxy)phenyl]-6-[$^{123}$I]iodoimidazo[1,2-a]pyridine. The column was rinsed with 1 mL of water, and then 1 mL of diethyl ether was passed therethrough to elute 2-[4'-(3"-hydroxypropoxy)phenyl]-6-[$^{123}$I]iodoimidazo[1,2-a]pyridine. The amount of radioactivity of the obtained compound was 219 MBq at the end of synthesis. Further, the TLC analysis was conducted under the following conditions, and as a result, the radiochemical purity of the compound was 97%.

TLC analysis conditions:
TLC plate: Silica Gel 60 $F_{254}$ (trade name; manufactured by Merck & Co., Inc.)
Mobile phase: Chloroform/methanol/triethylamine=100/1/2
Detector: Rita Star (trade name; manufactured by raytest)

Example II-20 to II-21, Comparative Example II-7

Measurement of Partition Coefficient Based on the Octanol Extraction Method

A diethyl ether solution (Example II-20) of Compound II-4 prepared in Example II-16, a diethyl ether solution (Example II-21) of Compound II-6 prepared in Example II-19, and a diethyl ether solution (Comparative Example II-7) of [$^{123}$I]-IMPY were each diluted with a 10 mg/mL ascorbic acid-containing physiological saline solution to adjust the radioactive concentration to 20-30 MBq/mL. To 2 mL of octanol, 10 μL each of the prepared sample solution was added, and 2 mL of 10 mmol/L phosphate buffer (pH 7.4) was further added, followed by stirring for 30 seconds. After the mixture was centrifuged with a low-speed centrifuge (2000 rpm×60 min.), the octanol layer and the water layer were sampled each in an amount of 1 mL, and subjected to measurement of radioactivity count with an autowell gamma system (Type: ARC-301B, manufactured by Aloka). Using the obtained radioactivity count, log P$_{octanol}$ was calculated in accordance with the equation (2-4).

$$\log P_{octanol} = \log_{10}\left(\frac{\text{Radioactivity count of octanol layer}}{\text{Radioactivity count of water layer}}\right) \quad (2\text{-}4)$$

The results are shown in Table 2-6. All compounds showed log P$_{octanol}$ value between 1 and 3. It is known that compounds permeable to BBB show a log P$_{octanol}$ value between 1 and 3 (Douglas D. Dischino et al., J. Nucl. Med., (1983), 24, p. 1030-1038). Thus, it is implied that both compounds have a BBB permeability comparable to IMPY.

TABLE 2-6 logP$_{octanol}$ value of the present compound

| Experiment | Compound | logP$_{octanol}$ value |
|---|---|---|
| Comparative Example II-7 | [$^{123}$I]-IMPY | 2.1 |
| Example II-20 | Compound II-4 | 2.5 |
| Example II-21 | Compound II-6 | 2.1 |

Example II-22 to II-23, Comparative Example II-8

Measurement of Transferability into Brain and Clearance

Using Compound II-4 and Compound II-6, a time course change of radioactive accumulation in brain of male Wistar rats (7-week old) was measured.

Compound II-4 (Example II-22), Compound II-6 (Example II-23) and a solution of [$^{123}$I]-IMPY (Comparative Example II-8) prepared above in Reference Example II-1 were each diluted with a 10 mg/mL ascorbic acid-containing physiological saline solution to prepare solutions (20-31 MBq/mL in radioactive concentration). 0.05 mL each of the prepared sample solutions was injected under thiopental anesthesia into the tail vein of the respective Wistar rat (7-week old). The rats were sacrificed by bleeding from abdominal artery, and brains were removed and subjected to measurement of mass of brains and further subjected to measurement of radioactivity (hereinafter referred to as A in this Example) with a single channel analyzer (detector type SP-20 manufactured by OHYO KOKEN KOGYO Co., Ltd.) 2, 5, 30, and 60 minutes after the injection. Further, the radioactivity level of the rest of the whole body was measured in the same manner as above (hereinafter referred to as B in this Example). Using these measurement results, radioactive distribution per unit weight of brain (% ID/g) at the respective time points were calculated in accordance with the following formula (2-5).

Three animals were used for the experiment at the respective time points.

$$\% \; ID/g = \frac{A}{B \times \text{brain weight}} \times 100 \quad (2\text{-}5)$$

The results are shown in Table 2-7. As shown in Table 2-7, Compounds II-4 and II-6 showed a significant accumulation like [$^{123}$I]-IMPY at the time point of two minutes after the injection, and then showed a tendency to rapidly clear away in 60 minutes. These results suggest that Compounds II-4 and II-6 possess high transferability to brain and rapid clearance from brain like [$^{123}$I]-IMPY.

TABLE 2-7

Radioactive distribution in brain of the present compound after intravenous injection (rats)

| | | Radioactive distribution per unit weight (% ID/g) | | | |
|---|---|---|---|---|---|
| Compound | | After 2 min. | After 5 min. | After 30 min. | After 60 min. |
| Example II-22 | Compound II-4 | 0.56 | 0.28 | 0.04 | 0.01 |
| Example II-23 | Compound II-6 | 0.81 | 0.56 | 0.07 | 0.02 |
| Comparative Example II-8 | $^{123}$I-IMPY | 1.19 | 0.97 | 0.23 | 0.09 |

Example II-24 to II-25

Confirmation of Imaging of Amyloid in Brain (1) Aβ$_{1-42}$ (Wako) was dissolved in phosphate buffer (pH 7.4) and shaken at 37° C. for 72 hours, to obtain 1 mg/mL of a suspension of aggregated Aβ (hereinafter referred to as amyloid suspension in the Examples).

(2) 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) A sample solution (30 MBq/mL in radioactivity concentration, Example II-24) in which Compound II-4 was dissolved in a 10 mg/mL ascorbic acid-containing physiological saline solution and a sample solution (30 MBq/mL in radioactivity concentration, Example II-25) in which Compound II-6 was dissolved in a 10 mg/mL ascorbic acid-containing physiological saline solution were prepared. This solution was injected under thiopental anesthesia into the rat through the tail vein (dosage: 0.5 mL, dosed radioactivity: 11-15 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 2-12 and FIG. 2-13).

FIG. 2-12 and FIG. 2-13 show images by autoradiogram and Thioflavin T staining of the brain slice of the rat to which amyloid was injected intracerebrally. As shown in these figures, a marked accumulation of radioactivity was observed in the amygdaloid nucleus on the side to which the amyloid suspension was injected, in both cases where Compounds II-4 and II-6 were administered. On the other hand, no significant accumulation of radioactivity was observed in the amygdaloid nucleus on the side to which the physiological saline solution was injected, compared with the other sites. On the autoradiogram, little accumulation of radioactivity was observed at sites other than the site to which amyloid was injected. From the result of Thioflavin T staining, it was confirmed that amyloid was present in the site where radioactivity was accumulated (FIG. 2-12 and FIG. 2-13). These results suggest that Compounds II-4 and II-6 possess a property of accumulating on intracerebral amyloid and a capability of imaging intracerebral amyloid.

Industrial Applicability

The compounds of the present invention can be utilized in the field of diagnostics.

BRIEF DESCRIPTION OF THE DRAWINGS

FIG. 1-2 is a scheme of synthesis of 6-bromo-2-[4'-(3''-p-toluenesulfonyloxypropoxy)phenyl]imidazo[1,2-a]pyridine.

FIG. 1-3 is a scheme of synthesis of 6-bromo-2-[4'-(2''-p-toluenesulfonyloxyethoxy)phenyl]imidazo[1,2-a]pyridine.

FIG. 1-4 is a scheme of synthesis of 6-bromo-2-[4'-(3''-fluoropropoxy)phenyl]imidazo[1,2-a]pyridine.

FIG. 1-5 is a scheme of synthesis of 2-[4'-(3''-fluoropropoxy)phenyl]-6-iodoimidazo[1,2-a]pyridine.

FIG. 1-6 is a scheme of synthesis of 6-bromo-2-[4'-(2''-fluoroethoxy)phenyl]imidazo[1,2-a]pyridine.

FIG. 1-7 is a scheme of synthesis of 2-[4'-(2''-fluoroethoxy)phenyl]-6-iodoimidazo[1,2-a]pyridine.

FIG. 1-8 is a scheme of synthesis of 2-[4'-(3''-fluoropropoxy)phenyl]-6-iodoimidazo[1,2-a]pyrimidine.

FIG. 1-9 is a scheme of synthesis of [$^{125}$I]-2-(4'-hydroxyphenyl)-6-iodoimidazo[1,2-a]pyridine.

FIG. 1-10 is a scheme of synthesis of 2-(4'-hydroxyphenyl)-6-iodoimidazo[1,2-a]pyridine.

FIG. 1-11 is a relationship between amyloid concentration and radioactive concentration in sample solutions.

FIG. 1-12(a) is an autoradiogram of the brain slice after the injection of Compound I-7, and FIG. 1-12(b) is a fluorescent microscopic image of the Thioflavin T stained sample (a magnification of the site to which the amyloid suspension was injected).

FIG. 1-13 is a scheme of synthesis of 6-tributylstannyl-2-[4'-(2''-fluoroethoxy)phenyl]imidazo[1,2-a]pyridine.

FIG. 1-14(a) is an autoradiogram of the brain slice after the injection of Compound I-9, and FIG. 1-14(b) is a fluorescent microscopic image of the Thioflavin T stained sample (a magnification of the site to which the amyloid suspension was injected).

FIG. 2-1 is a scheme of synthesis of 2-[4'-(2-hydroxyethoxy)phenyl]-6-iodoimidazo[1,2-a]pyridine (non-radioactive iodinated form).

FIG. 2-2 is a scheme of synthesis of 6-tributylstannyl-2-[4'-(2''-hydroxyethoxy)phenyl]imidazo[1,2-a]pyridine.

FIG. 2-3 is a scheme of synthesis of 2-(4'-ethoxyphenyl)-6-iodoimidazo[1,2-a]pyridine (non-radioactive iodinated form).

FIG. 2-4 is a scheme of synthesis of 6-tributylstannyl-2-(4'-ethoxyphenyl)imidazo[1,2-a]pyridine.

FIG. 2-5(a) is an autoradiogram of the brain slice after the injection of $^{123}$I-IMPY, and FIG. 2-5(b) is a fluorescent microscopic image of the Thioflavin T stained sample (a magnification of the site to which the amyloid suspension was injected).

FIG. 2-6(a) is an autoradiogram of the brain slice after the injection of 2-[4'-(2''-hydroxyethoxy)phenyl]-6-[$^{123}$I]iodoimidazo[1,2-a]pyridine, and FIG. 2-6(b) is a fluorescent microscopic image of the Thioflavin T stained sample (a magnification of the site to which the amyloid suspension was injected).

FIG. 2-7(a) is an autoradiogram of the brain slice after the injection of 2-(4'-ethoxyphenyl)-6-[$^{123}$I]iodoimidazo[1,2-a]pyridine, and FIG. 2-7(b) a fluorescent microscopic image of the Thioflavin T stained sample (a magnification of the site to which the amyloid suspension was injected).

FIG. 2-8 is a scheme of synthesis of 2-[3'-(2''-hydroxyethoxy)phenyl]-6-iodoimidazo[1,2-a]pyridine (non-radioactive iodinated form).

FIG. 2-9 is a scheme of synthesis of 6-tributylstannyl-2-[3'-(2''-hydroxyethoxy)phenyl]imidazo[1,2-a]pyridine.

FIG. 2-10 is a scheme of synthesis of 2-[4'-(3''-hydroxypropoxy)phenyl]-6-iodoimidazo[1,2-a]pyridine (non-radioactive iodinated form).

FIG. 2-11 is a scheme of synthesis of 6-tributylstannyl-2-[4'-(3''-hydroxypropoxy)phenyl]imidazo[1,2-a]pyridine.

FIG. 2-12(a) is an autoradiogram of the brain slice after the injection of Compound II-4, and FIG. 2-12(b) is a fluorescent microscopic image of the Thioflavin T stained sample (a magnification of the site to which the amyloid suspension was injected).

FIG. 2-13(a) is an autoradiogram of the brain slice after the injection of Compound II-6, and FIG. 2-13(b) is a fluorescent microscopic image of the Thioflavin T stained sample (a magnification of the site to which the amyloid suspension was injected).

Figure 1:
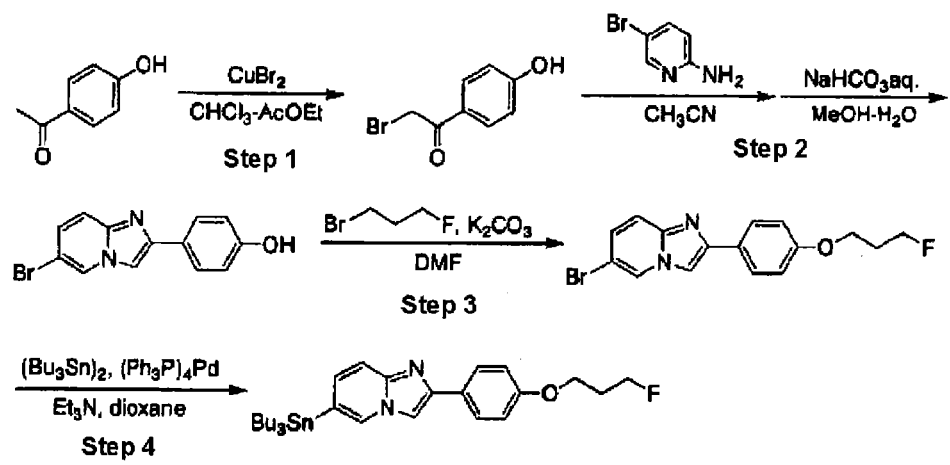
FIG. 1-1 is a scheme of synthesis of 6-tributylstannyl-2-[4'-(3''-fluoropropoxy)phenyl]imidazo[1,2-a]pyridine.
Figures 1, 2:
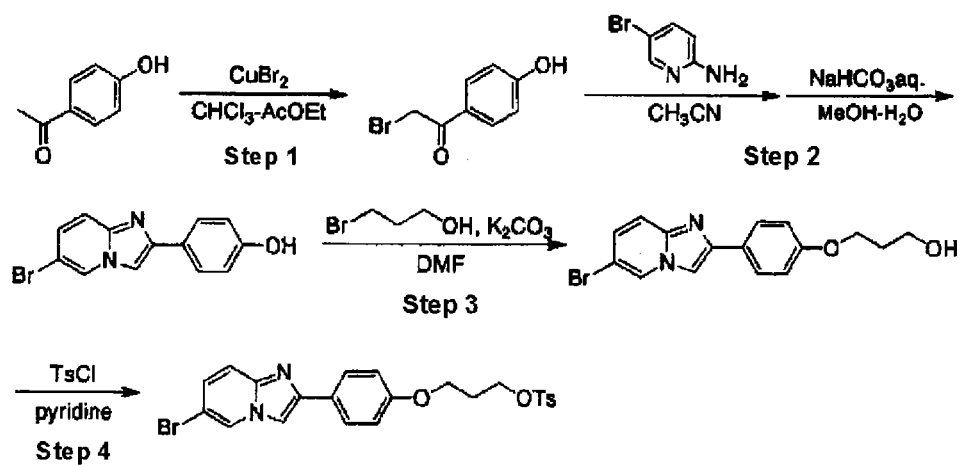
Figures 1, 2, 3:
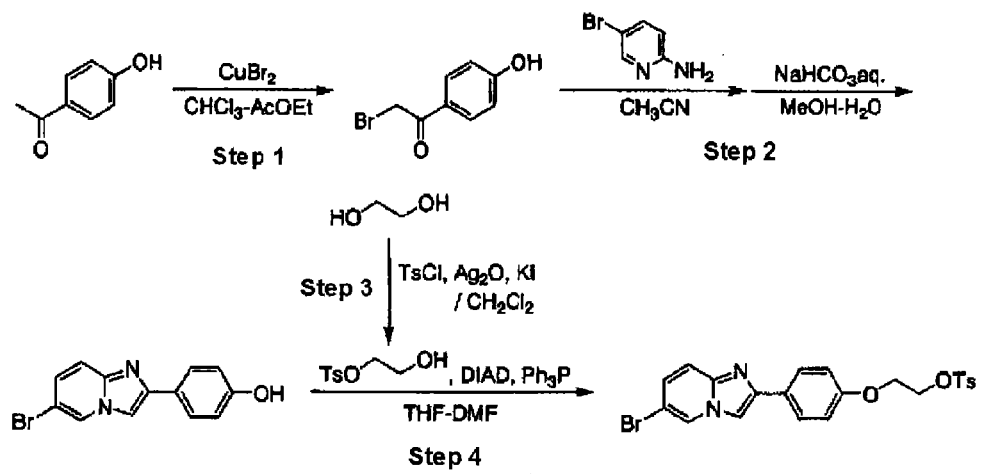
Figures 1, 2, 3, 4:
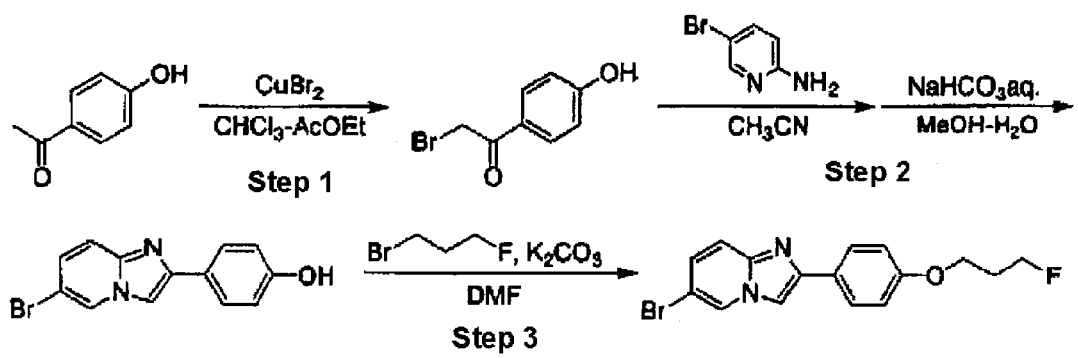
Figures 1, 2, 3, 4, 5:
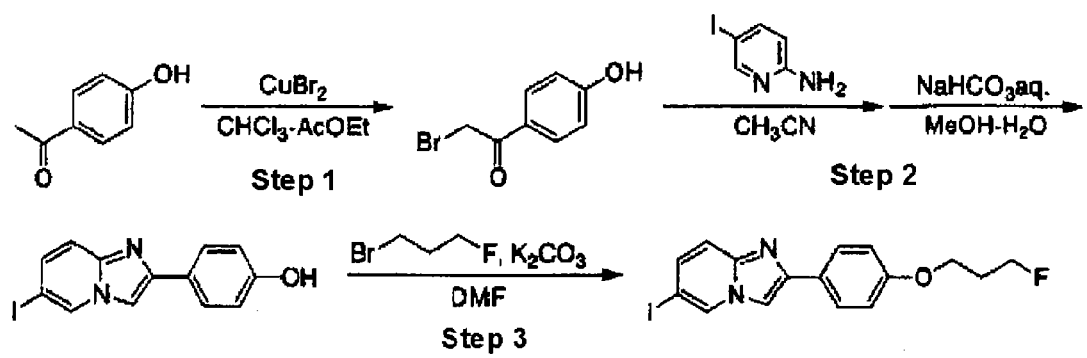
Figures 1, 2, 3, 4, 5, 6:
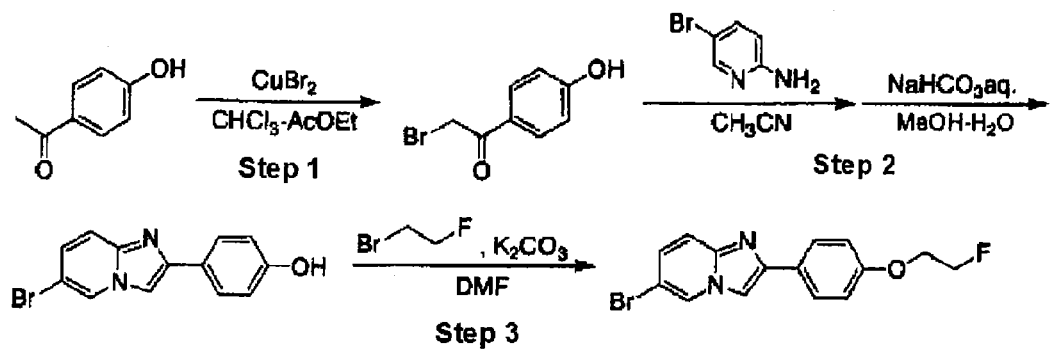
Figures 1, 2, 3, 4, 5, 6, 7:
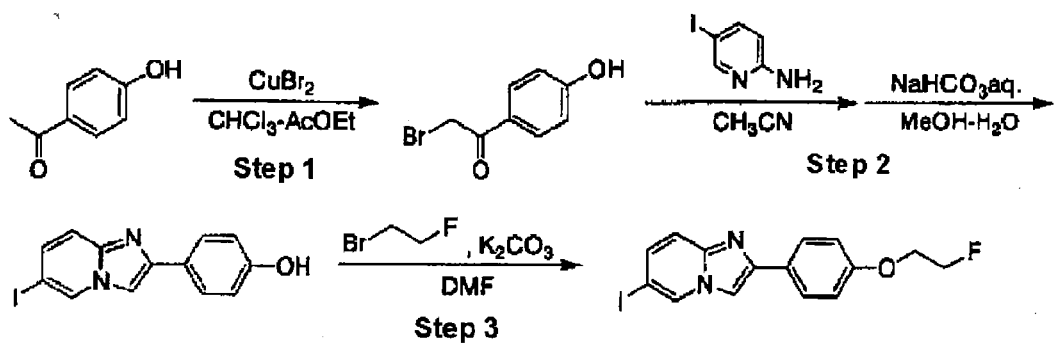
Figures 1, 2, 3, 4, 5, 6, 7, 8:
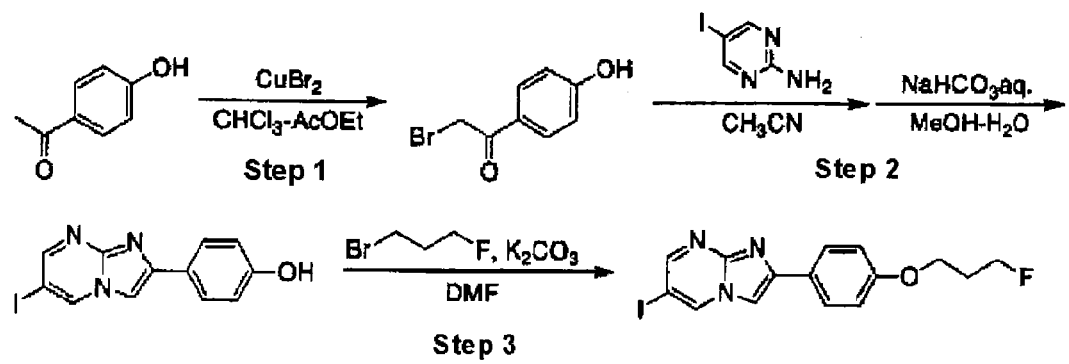
Figures 1, 2, 3, 4, 5, 6, 7, 8, 9:
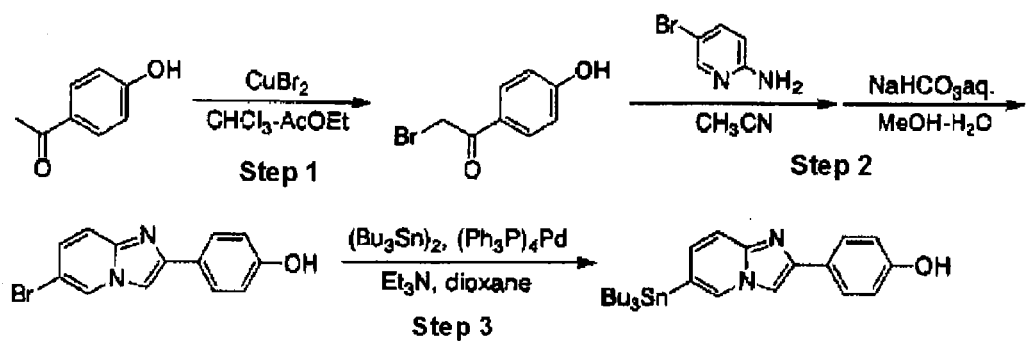
Figures 1, 2, 3, 4, 5, 6, 7, 8, 9, 10:
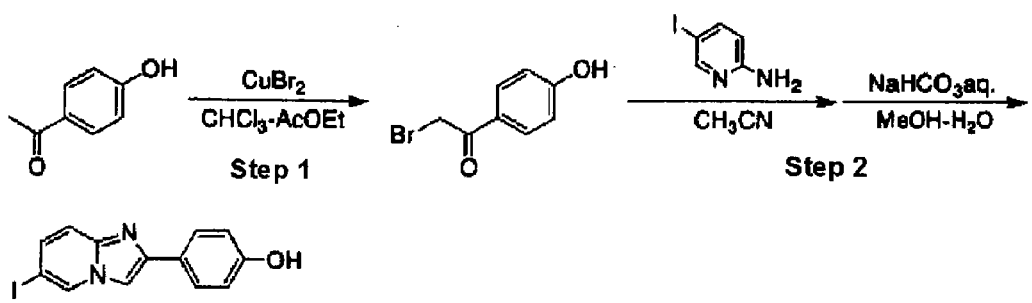
Figures 1, 2, 3, 4, 5, 6, 7, 8, 9, 10, 11:
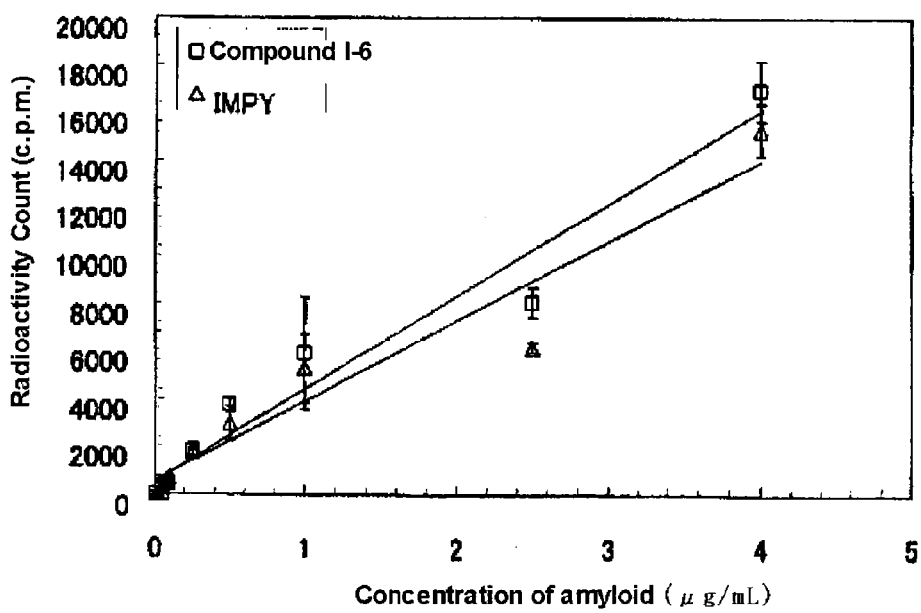
Figures 1, 2, 3, 4, 5, 6, 7, 8, 9, 10, 11, 12:
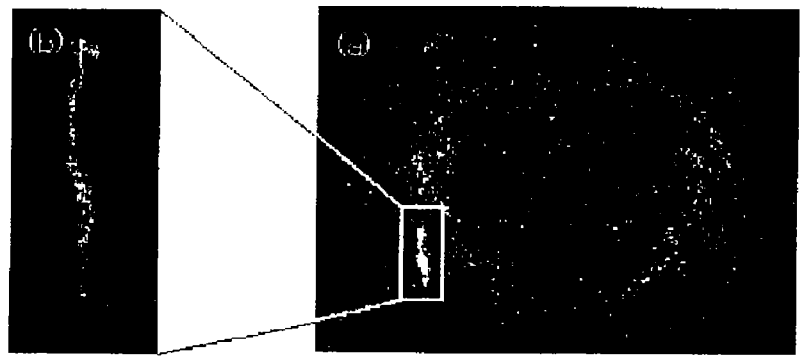
Figures 1, 2, 3, 4, 5, 6, 7, 8, 9, 10, 11, 12, 13:
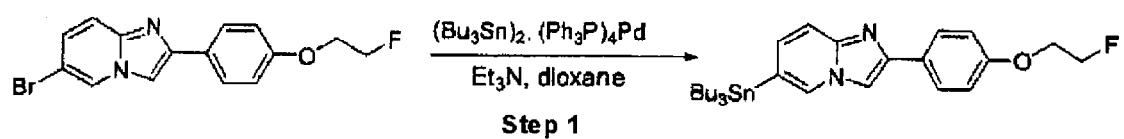
Figures 1, 2, 3, 4, 5, 6, 7, 8, 9, 10, 11, 12, 13, 14:
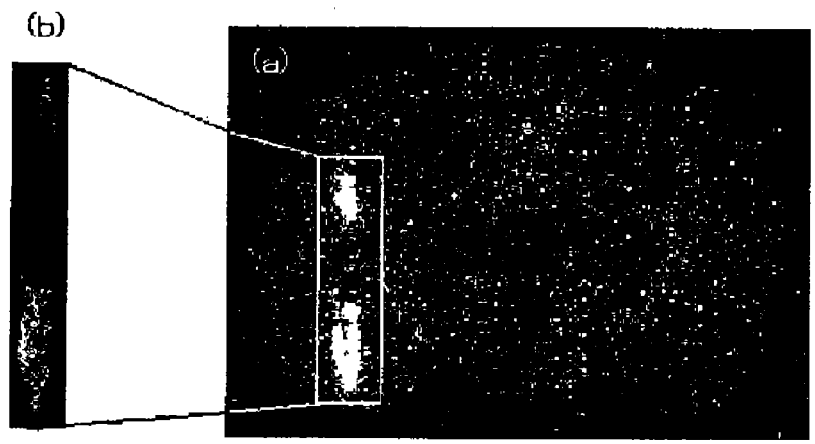
Figures 1, 2:
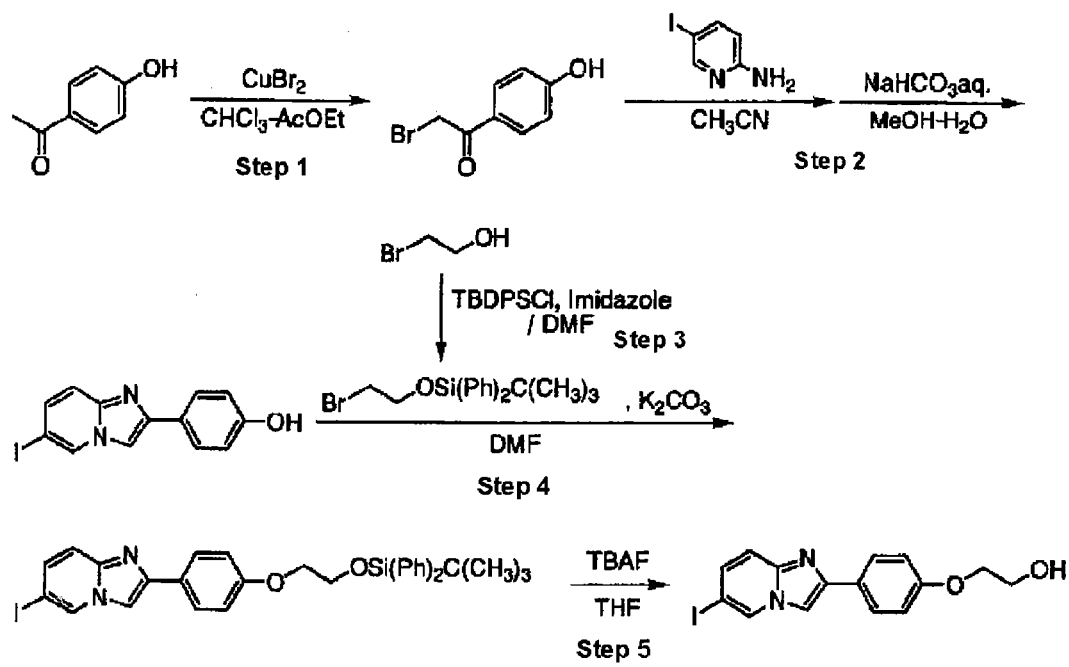
Figure 2:
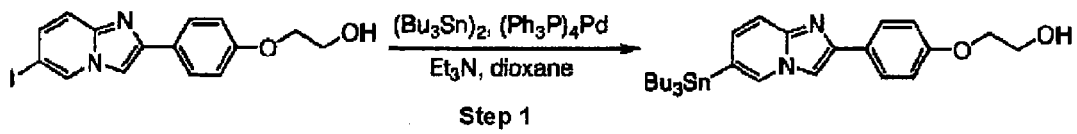
Figures 2, 3:
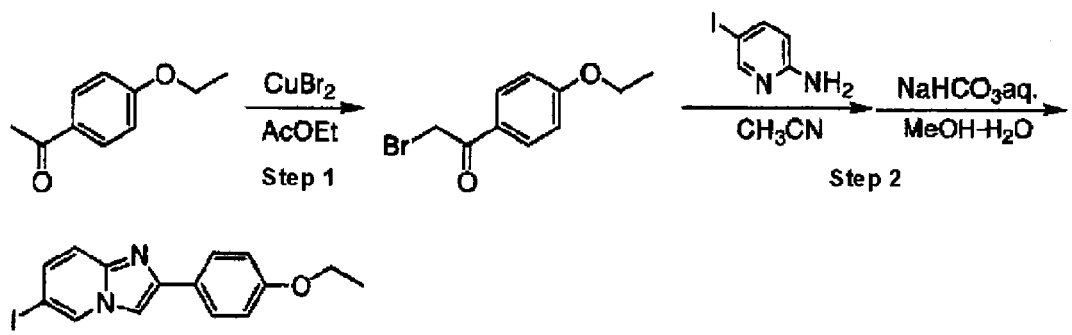
Figures 2, 3, 4:
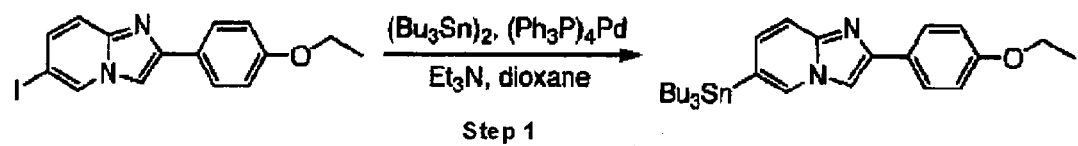
Figures 2, 3, 4, 5:
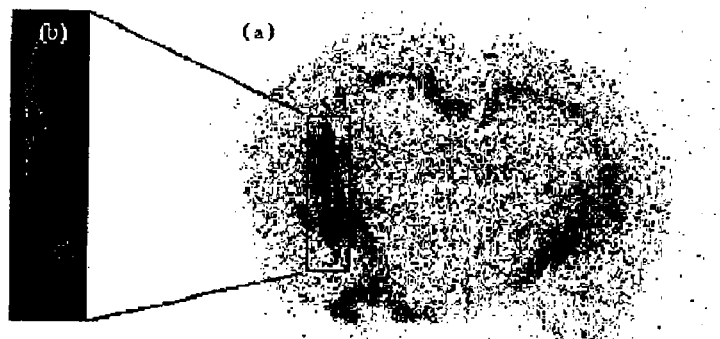
Figures 2, 3, 4, 5, 6:
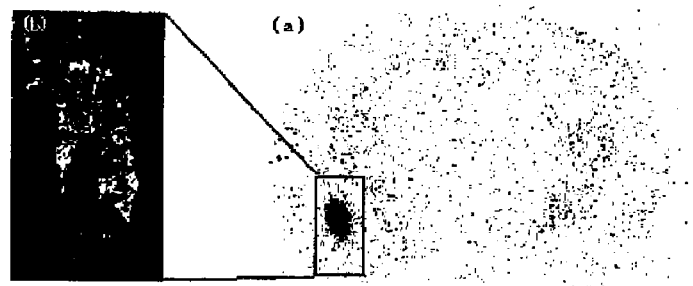
Figures 2, 3, 4, 5, 6, 7:
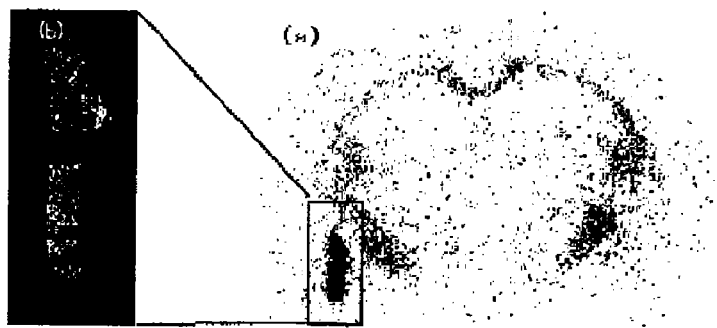
Figures 2, 3, 4, 5, 6, 7, 8:
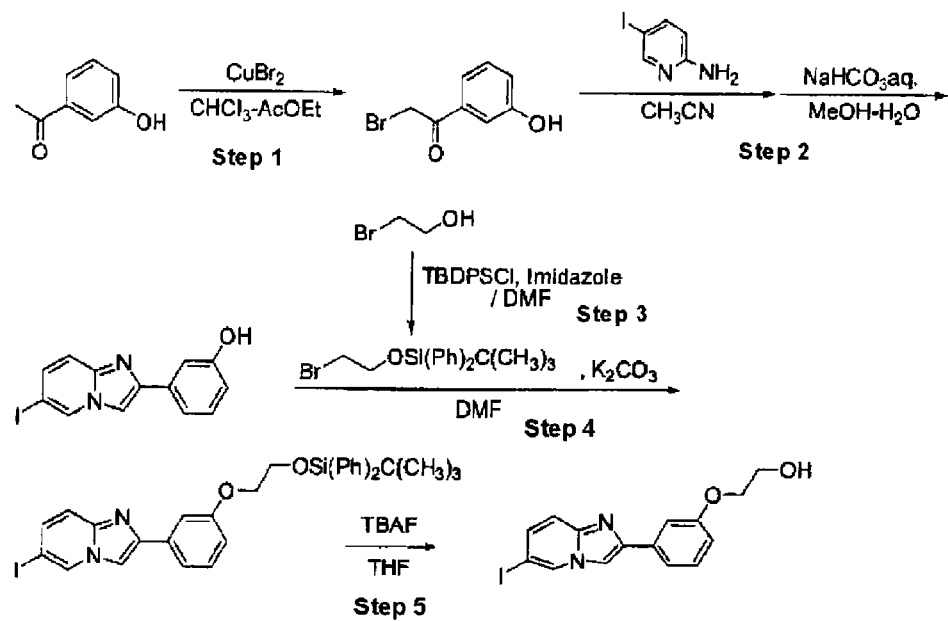
Figures 2, 3, 4, 5, 6, 7, 8, 9:
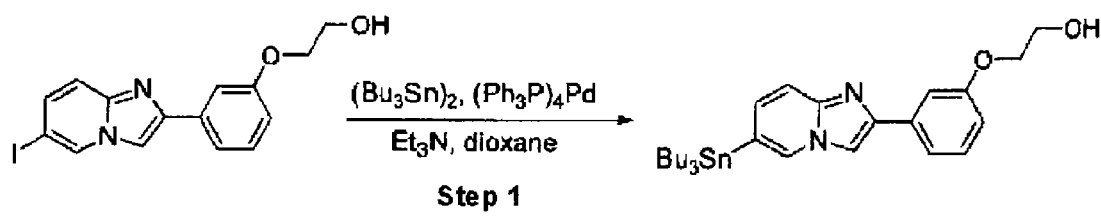
Figures 2, 3, 4, 5, 6, 7, 8, 9, 10:
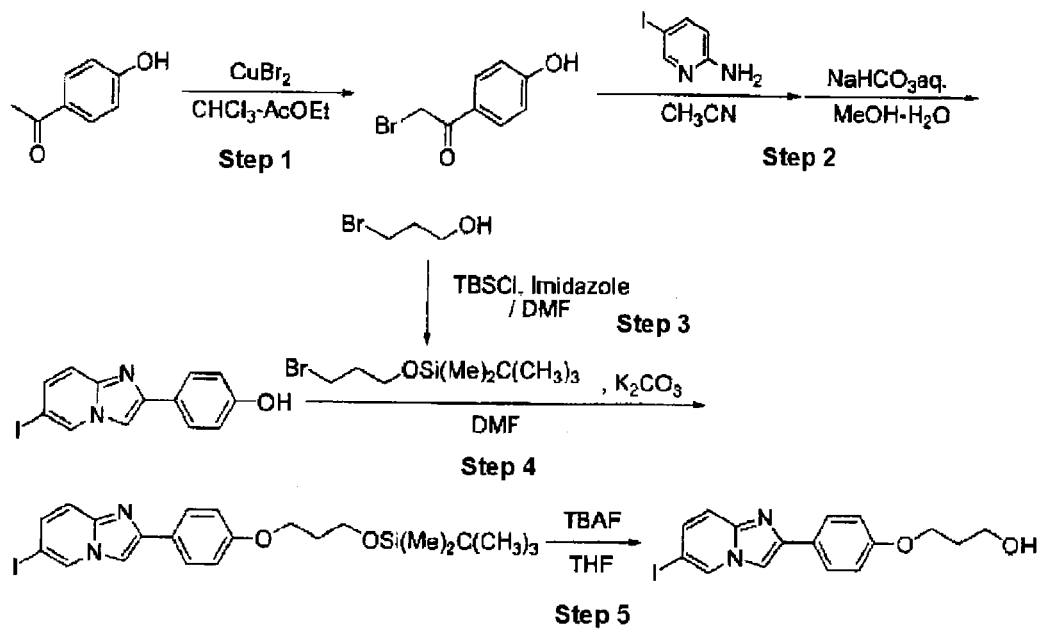
Figures 2, 3, 4, 5, 6, 7, 8, 9, 10, 11:
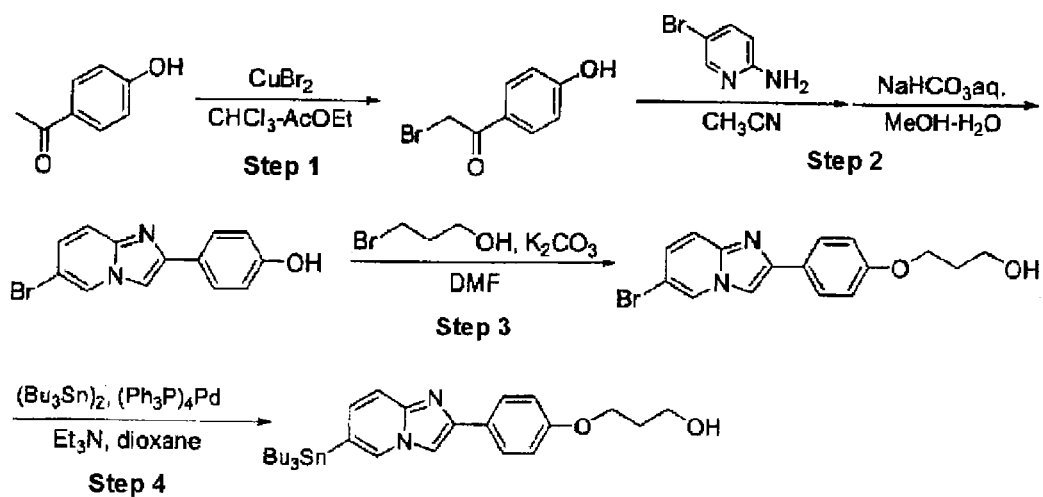
Figures 2, 3, 4, 5, 6, 7, 8, 9, 10, 11, 12:
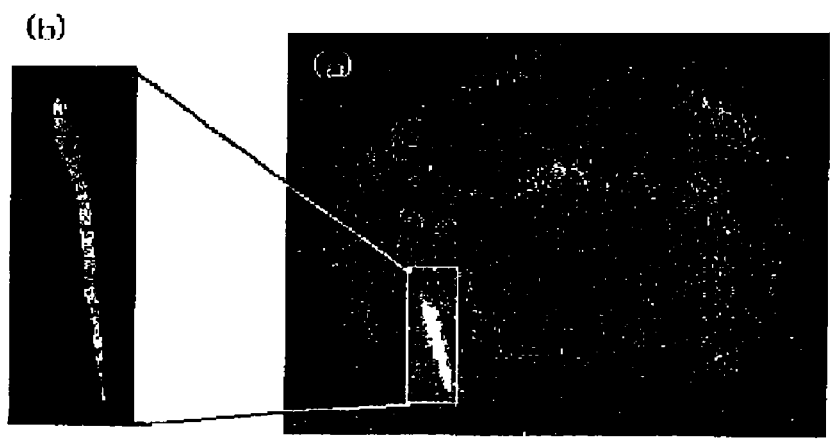
Figures 2, 3, 4, 5, 6, 7, 8, 9, 10, 11, 12, 13:
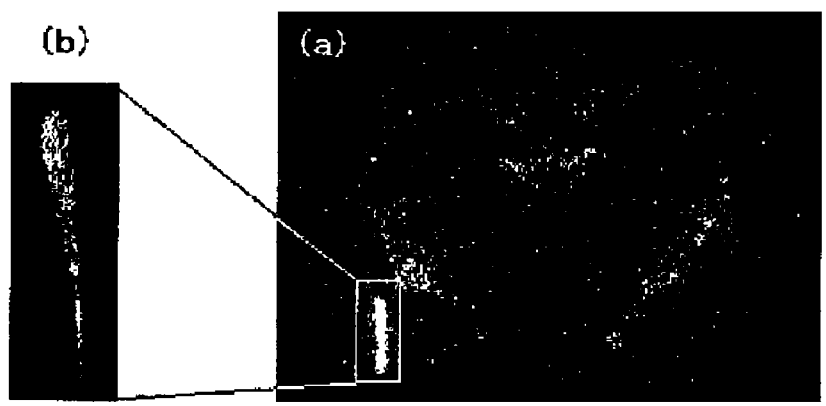

The invention claimed is:

1. A compound represented by the following formula (3), or a salt thereof:

$$(3)$$

wherein $A_9$, $A_{10}$, $A_{11}$ and $A_{12}$ represent a carbon, $R^5$ is a radioactive halogen substituent, $R^6$ is a group selected from the group consisting of a hydroxyl group, a methoxy group, a carboxyl group, an N-methylamino group, an and a cyano group, and P is an integer of 0 to 2, and provided that $R^5$ binds to a carbon represented by $A_9$, $A_{10}$, $A_{11}$ and $A_{12}$.

2. A compound or a salt thereof according to claim 1, wherein $R^5$ is selected from the $^{18}F$, $^{76}Br$, $^{123}I$, $^{124}I$, $^{125}I$ and $^{131}I$.

3. A compound represented by the following formula (4) or a salt thereof:

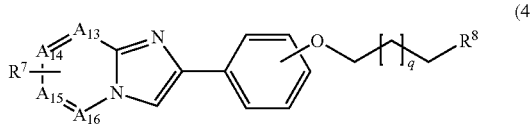

(4)

wherein $A_{13}$, $A_{14}$, $A_{15}$ and $A_{16}$ represent a carbon, $R^7$ is a group selected from the group consisting of a non-radioactive halogen substituent, a nitro substituent, a trialkylammonium group having alkyl chains with 1 to 4 carbon atoms, a trialkylstannyl substituent having alkyl chains with 1 to 4 carbon atoms and a triphenylstannyl group, $R^8$ is a group selected from the group consisting of a hydroxyl group, a methoxy group, a carboxyl group, an N-methylamino group, and a cyano group, and q is an integer of 0 to 2, and provided that $R^7$ binds to a carbon represented by $A_{13}$, $A_{14}$, $A_{15}$ and $A_{16}$.

4. A diagnostic agent for Alzheimer's disease, which comprises a compound represented by the following formula (3), or a salt thereof:

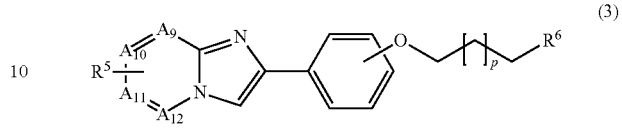

(3)

wherein $A_9$, $A_{10}$, $A_{11}$, and $A_{12}$ represent a carbon, $R^5$ is a radioactive halogen substituent, $R^6$ is a group selected from the group consisting of a hydroxy group, a methoxy group, a carboxyl group, an N-methylamino group, and a cyano group, and P is an integer of 0 to 2, and provided that $R^5$ binds to a carbon represented by $A_9$, $A_{10}$, $A_{11}$ and $A_{12}$.

5. The diagnostic agent for Alzheimer's disease, according to claim 4, wherein $R^5$ is selected from the group consisting of $^{18}F$, $^{76}Br$, $^{123}I$, $^{124}I$, $^{125}I$ and $^{131}I$.

\* \* \* \* \*